(12) United States Patent
Nishio et al.

(10) Patent No.: US 10,280,145 B2
(45) Date of Patent: May 7, 2019

(54) UREA DERIVATIVE AND USE THEREFOR

(71) Applicant: Toray Industries, Inc., Tokyo (JP)

(72) Inventors: Yukihiro Nishio, Kamakura (JP); Yuko Kubota, Kamakura (JP); Masashi Yamamoto, Kamakura (JP); Yutaka Nishimura, Kamakura (JP); Tomohide Masuda, Kamakura (JP); Hideyuki Tsutsui, Otsu (JP); Keiichi Okimura, Kamakura (JP); Syuji Udagawa, Kamakura (JP); Mie Kaino, Kamakura (JP); Hiroyuki Meguro, Kamakura (JP); Yumiko Sekiya, Otsu (JP)

(73) Assignee: Toray Industries, Inc. (JP)

( * ) Notice: Subject to any disclaimer, the term of this patent is extended or adjusted under 35 U.S.C. 154(b) by 0 days.

(21) Appl. No.: 15/753,567

(22) PCT Filed: Aug. 31, 2016

(86) PCT No.: PCT/JP2016/075500
§ 371 (c)(1),
(2) Date: Feb. 20, 2018

(87) PCT Pub. No.: WO2017/038873
PCT Pub. Date: Mar. 9, 2017

(65) Prior Publication Data
US 2018/0237398 A1 Aug. 23, 2018

(30) Foreign Application Priority Data
Aug. 31, 2015 (JP) ................. 2015-170015

(51) Int. Cl.
| | | |
|---|---|---|
| C07D 401/12 | (2006.01) |
| C07D 239/47 | (2006.01) |
| C07D 403/12 | (2006.01) |
| C07D 405/14 | (2006.01) |
| A61K 31/17 | (2006.01) |
| A61K 31/4406 | (2006.01) |
| A61K 31/4409 | (2006.01) |
| A61K 31/4427 | (2006.01) |
| A61K 31/4439 | (2006.01) |
| A61K 31/4545 | (2006.01) |
| A61K 31/50 | (2006.01) |
| A61K 31/506 | (2006.01) |

(Continued)

(52) U.S. Cl.
CPC ............ *C07D 239/47* (2013.01); *A61K 31/17* (2013.01); *A61K 31/4406* (2013.01); *A61K 31/4409* (2013.01); *A61K 31/4427* (2013.01); *A61K 31/4439* (2013.01); *A61K 31/4545* (2013.01); *A61K 31/50* (2013.01); *A61K 31/506* (2013.01); *A61K 31/513* (2013.01); *A61K 31/5377* (2013.01); *C07C 275/34* (2013.01); *C07D 213/30* (2013.01); *C07D 213/65* (2013.01); *C07D 213/74* (2013.01); *C07D 237/14* (2013.01); *C07D 239/34* (2013.01); *C07D 401/04* (2013.01); *C07D 401/12* (2013.01); *C07D 403/12* (2013.01); *C07D 405/12* (2013.01); *C07D 405/14* (2013.01)

(58) Field of Classification Search
CPC .. C07D 401/12; C07D 405/12; C07D 239/34; C07D 239/47; C07D 401/04; C07D 403/12; C07D 405/14; C07D 213/30; C07D 213/65; C07D 237/14
USPC .......... 544/238, 315, 321, 123; 546/290, 298
See application file for complete search history.

(56) References Cited

U.S. PATENT DOCUMENTS

2009/0137580 A1    5/2009   Imamura et al.

FOREIGN PATENT DOCUMENTS

| | | |
|---|---|---|
| CN | 102319242 A | 1/2012 |
| WO | 2011/040509 A1 | 4/2011 |

(Continued)

OTHER PUBLICATIONS

Wolfgang Vogel et al., "The Discoidin Domain Receptor Tyrosine Kinases Are Activated by Collagen," Molecular Cell, vol. 1, Dec. 1997, pp. 13-23.

(Continued)

*Primary Examiner* — Jeffrey H Murray
(74) *Attorney, Agent, or Firm* — DLA Piper LLP (US)

(57) ABSTRACT

A compound has inhibitory activity on Discoidin Domain Receptor 1. A urea derivative is represented by the formula (I) or a pharmaceutically acceptable salt thereof:

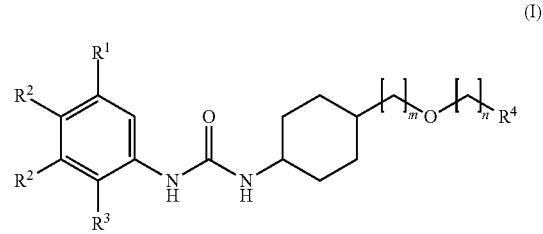

(I)

wherein, $R^1$ is trifluoromethyl, trifluoromethoxy, or pentafluorosulfanyl; each $R^2$ is independently a hydrogen atom or methyl which is optionally substituted by one hydroxyl or one saturated heterocyclyl having four to six ring-forming atoms; $R^3$ is a hydrogen atom, halogen atom, $C_1$-$C_3$ alkyl, saturated heterocyclyl having four to six ring-forming atoms and optionally having an oxo group, or $R^5O$—; and $R^4$ is phenyl, pyridyl, pyridazinyl, or pyrimidinyl, which phenyl, pyridyl, pyridazinyl, or pyrimidinyl is optionally substituted by one $R^6$.

8 Claims, No Drawings

(51) Int. Cl.
    *A61K 31/513*   (2006.01)
    *A61K 31/5377*   (2006.01)
    *C07D 213/74*   (2006.01)
    *C07C 275/34*   (2006.01)
    *C07D 401/04*   (2006.01)
    *C07D 237/14*   (2006.01)
    *C07D 239/34*   (2006.01)
    *C07D 405/12*   (2006.01)
    *C07D 213/30*   (2006.01)
    *C07D 213/65*   (2006.01)

(56) References Cited

FOREIGN PATENT DOCUMENTS

| WO | 2012/000304 A1 | 1/2012 |
|---|---|---|
| WO | 2013/161851 A1 | 10/2013 |
| WO | 2013/161853 A1 | 10/2013 |
| WO | 2014/032755 A2 | 3/2014 |
| WO | 2015/038778 A1 | 3/2015 |

OTHER PUBLICATIONS

Wolfgang Vogel, "Discoidin domain receptors: structural relations and functional implications," The FASEB Journal, vol. 13, No. 9001, 1999, pp. S77-S82.

Wolfgang F. Vogel et al., "Sensing extracellular matrix: An update on discoidin domain receptor function," Cellular Signalling, vol. 18, Issue 8, Aug. 2006, pp. 1108-1116 (Abstract only).

R. Yamanaka et al., "Identification of expressed genes characterizing long-term survival in malignant glioma patients," Oncogene, vol. 25, 2006, pp. 5994-6002.

C.E. Ford et al., "Expression and mutation analysis of the discoidin domain receptors 1 and 2 in non-small cell lung carcinoma," British Journal of Cancer, vol. 96, 2007, pp. 808-814.

Hyung-Gu Kim et al., "DDR1 Receptor Tyrosine Kinase Promotes Prosurvival Pathway through Notch1 Activation," The Journal of Biological Chemistry, vol. 286, No. 20, May 20, 2011, pp. 17672-17681.

Karmele Valencia et al., "Inhibition of Collagen Receptor Discoidin Domain receptor-1 (DDR1) Reduces Cell Survival, Homing, and Colonization in Lung Cancer Bone Metastasis," Clinical Cancer Research, vol. 18, Jan. 5, 2012, pp. 969-980.

R.R. Valiathan et al., "Discoidin domain receptor tyrosine kinases: new players in cancer progression," Cancer and Metastasis Reviews, vol. 31, Issue 1-2, Jun. 2012, pp. 295-321 (Abstract only).

L. Miao et al., "Discoidin domain receptor 1 is associated with poor prognosis of non-small cell lung cancer and promotes cell invasion via epithelial-to-mesenchymal transition," Medical Oncology, vol. 30, Article 626, Sep. 2013 (Abstract only).

Mingshan Gao et al., "Discovery and Optimization of 3-(2-(Pyrazolo[1,5-a]pyrimidin-6-yl)ethynyl) benzamides as Novel Selective and Orally Bioavailable Discoidin Domain Receptor 1 (DDR1) Inhibitors," Journal of Medicinal Chemistry, vol. 56, No. 8, Mar. 22, 2013, pp. 3381-3295 (Abstract only).

Hyung-Gu Kim et al., "Discovery of a Potent and Selective DDR1 Receptor Tyrosine Kinase Inhibitor," ACS Chemical Biology, vol. 8, 2013, pp. 2145-2150.

Ting Chen et al., "Explorations of Substituted Urea Functionality for the Discovery of New Activators of the Heme-Regulated Inhibitor Kinase," Journal of Medicinal Chemistry, vol. 56, No. 23, Nov. 21, 2013, pp. 9457-9470 (Abstract only).

K.T. Barker et al., "Expression patterns of the novel receptor-like tyrosine kinase, DDR, in human breast tumours," Oncogene, vol. 10, No. 3, Feb. 2, 1995, pp. 569-575 (Abstract only).

Extended European Search Report dated Dec. 17, 2018, of counterpart European Application No. 16841903.4.

UREA DERIVATIVE AND USE THEREFOR

TECHNICAL FIELD

This disclosure relates to a urea derivative and use thereof.

BACKGROUND

Discoidin Domain Receptor 1 (hereinafter referred to as DDR1) is a receptor-type tyrosine kinase activated by its ligand, insoluble collagen, and carries a discoidin domain which is capable of binding to collagen in its extracellular region, and a receptor-type tyrosine kinase domain in its intracellular region, respectively (Vogel et al., British Journal of Cancer, (2007) 96: 808-814 and Vogel et al., Cellular Signalling, (2006) 18: 1108-1116).

It has been reported that activation of DDR1 causes promotion of cell infiltration, cell migration, and cell survival (Vogel et al., FASEB Journal, (1999) 13: S77-S82, Valiathan et al., Cancer Metastasis Review, (2012) 31: 295-321 and Vogel et al., Molecular Cell, (1997) 1: 13-23). In the clinical setting, it has been reported that expression of DDR1 is increased in non-small cell lung cancer, glioma, and breast cancer, and the increased expression of DDR1 is correlated with poor prognosis and with cell infiltration in non-small cell lung cancer (Valencia et al., Clinical Cancer Research, (2012) 18: 969-980, Barker et al., Oncogene, (1995) 10: 569-575, Yamanaka et al., Oncogene, (2006) 25: 5994-6002 and Miao et al., Medical Oncology, (2013) 30: 626).

It has been reported that knocking-down of DDR1 by RNA interference results in suppressing bone metastasis of lung cancer cells (Valencia et al.) and decreasing the tumorigenicity of colorectal cancer (Hung-Gu et al., Journal of Biological Chemistry, (2011) 286: 17672-17681).

Examples of compounds that reportedly have inhibitory activity on DDR1 include 3-(2-(pyrazolo [1,5-a]pyrimidin-6-yl)ethinyl)benzamide derivatives (WO 2012/000304 and Ding et al., Journal of Medicinal Chemistry, (2013) 56: 3281-3295), 4-(((4-ethylpiperazinyl)methyl)-3-trifluoromethylbenzamide derivatives (Gray et al., ACS Chemical Biology, (2013) 8: 2145 2150), and 4-piperazinylmethyl-3-trifluoromethylbenzamide derivatives (WO 2013/161851 and WO 2013/161853).

On the other hand, among those compounds having a urea skeleton, for example, 2,3-dihydro-1H-inden-2-ylurea derivatives (WO 2011/040509) are reported to be compounds with inhibitory activity on p38MAPK.

However, no compound with inhibitory activity on DDR1 has been reported in the compounds having a urea skeleton.

Thus, it could be helpful to provide a compound with inhibitory activity on DDR1.

SUMMARY

We found that a novel urea derivative or a pharmaceutically acceptable salt thereof has inhibitory activity on DDR1 (hereinafter referred to as DDR1 inhibition activity).

We thus provide a urea derivative represented by Formula (I):

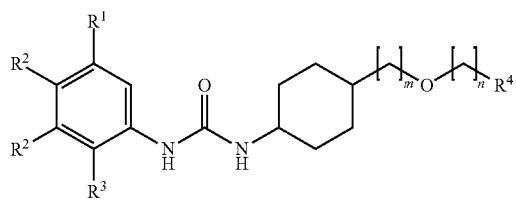

(I)

wherein, $R^1$ is trifluoromethyl, trifluoromethoxy, or pentafluorosulfanyl;

each $R^2$ is independently a hydrogen atom or methyl which is optionally substituted by one hydroxyl or one saturated heterocyclyl having four to six ring-forming atoms;

$R^3$ is a hydrogen atom, halogen atom, $C_1$-$C_3$ alkyl, saturated heterocyclyl having four to six ring-forming atoms and optionally having an oxo group, or $R^5O$—;

$R^4$ is phenyl, pyridyl, pyridazinyl, or pyrimidinyl, which phenyl, pyridyl, pyridazinyl, or pyrimidinyl is optionally substituted by one $R^6$;

m and n are independently 0 or 1;

$R^5$ is $C_1$-$C_3$ alkyl or saturated heterocyclyl having four to six ring-forming atoms (provided that if one of the ring-forming atoms of $R^5$ is a nitrogen atom, that is, a nitrogen atom is included in the ring-forming atoms of $R^5$, the above-described nitrogen atom is optionally substituted by acetyl);

$R^6$ is carbamoyl, phenyl, heteroaryl having five or six ring-forming atoms, saturated heterocyclyl having four to six ring-forming atoms, or $(R^7)R^8N$—; and each of $R^7$ and $R^8$ is independently a hydrogen atom, or $C_1$-$C_3$ alkyl which is optionally substituted by hydroxyl (excluding the cases where m and n are 0; and $R^4$ is phenyl or pyridyl, which phenyl or pyridyl is substituted by carbamoyl) or a pharmaceutically acceptable salt thereof.

In the urea derivative represented by Formula (I), preferably, each $R^2$ is independently a hydrogen atom or hydroxymethyl;

$R^3$ is a hydrogen atom, morpholinyl, 2-oxopiperazinyl, or $R^5O$—;

$R^4$ is pyridyl or pyrimidinyl, which pyridyl or pyrimidinyl is optionally substituted by one $R^6$;

$R^5$ is $C_1$-$C_3$ alkyl, 3-oxetanyl, or 3-azetidinyl, 3-pyrrolidinyl, or 4-piperidinyl, which 3-azetidinyl, 3-pyrrolidinyl, or 4-piperidinyl optionally has a nitrogen atom substituted by acetyl; and $R^6$ is carbamoyl, pyridyl, morpholinyl, or $(R^7)R^8N$—.

In this case, higher DDR1 inhibition activity can be expected.

Moreover, in the urea derivative represented by Formula (I), more preferably, $R^4$ is a group represented by one formula selected from Formulae (IIa) to (IIc), and m and n are 0:

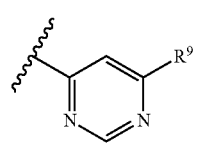

(IIa)

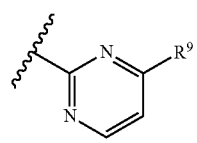

(IIb)

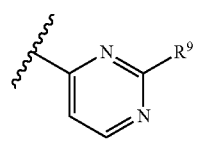

(IIc)

wherein R⁹ is carbamoyl, pyridyl, morpholinyl, or (R⁷)R⁸N—; and the wavy line represents the point to which Formula (I) is linked.

Moreover, more preferably, R⁴ is a group represented by Formula (IId) or (IIe), and one of m and n is 0 and the other is 1:

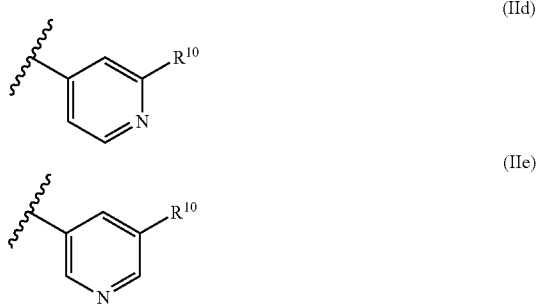

wherein R¹⁰ is a hydrogen atom or carbamoyl; and the wavy line represents the point to which Formula (I) is linked.

In these cases, still higher DDR1 inhibition activity can be expected.

Also, we provide an inhibitor of DDR1 comprising, as an active ingredient, the urea derivative represented by Formula (I) or a pharmaceutically acceptable salt thereof.

Urea derivatives and pharmaceutically acceptable salts thereof have high DDR1 inhibition activity and therefore can be utilized as DDR1 inhibitors.

DETAILED DESCRIPTION

A urea derivative is characteristically represented by Formula (I):

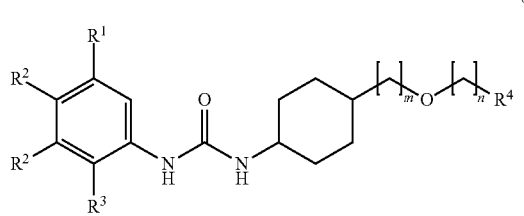

wherein R¹ is trifluoromethyl, trifluoromethoxy, or pentafluorosulfanyl;

each R² is independently a hydrogen atom or methyl which is optionally substituted by one hydroxyl or one saturated heterocyclyl having four to six ring-forming atoms;

R³ is a hydrogen atom, halogen atom, $C_1$-$C_3$ alkyl, saturated heterocyclyl having four to six ring-forming atoms and optionally having an oxo group, or R⁵O—;

R⁴ is phenyl, pyridyl, pyridazinyl, or pyrimidinyl, which phenyl, pyridyl, pyridazinyl, or pyrimidinyl is optionally substituted by one R⁶;

m and n are independently 0 or 1;

R⁵ is $C_1$-$C_3$ alkyl or saturated heterocyclyl having four to six ring-forming atoms (provided that if one of the ring-forming atoms of R⁵ is a nitrogen atom, that is, a nitrogen atom is included in the ring-forming atoms of R⁵, the above-described nitrogen atom is optionally substituted by acetyl);

R⁶ is carbamoyl, phenyl, heteroaryl having five or six ring-forming atoms, saturated heterocyclyl having four to six ring-forming atoms, or (R⁷)R⁸N—; and each of R⁷ and R⁸ is independently a hydrogen atom, or $C_1$-$C_3$ alkyl which is optionally substituted by hydroxyl (excluding the cases where m and n are 0; and R⁴ is phenyl or pyridyl, which phenyl or pyridyl is substituted by carbamoyl).

Unless otherwise specified, the following terms used herein are as defined below.

The term "halogen atom" means fluorine atom, chlorine atom, bromine atom, or iodine atom.

The term "$C_1$-$C_3$ alkyl" means methyl, ethyl, propyl, or isopropyl.

The term "saturated heterocyclyl having four to six ring-forming atoms" means a monocyclic saturated heterocyclyl group having a four- to six-membered ring comprising the same or different one or more atoms selected from the group consisting of oxygen, sulfur and nitrogen, and one to five carbon atoms, and the term includes, for example, azetidinyl, pyrrolidinyl, piperidinyl, oxetanyl, tetrahydrofuranyl, tetrahydropyranyl, piperazinyl, or morpholinyl group. In addition, examples of a saturated heterocyclyl having four to six ring-forming atoms in which a nitrogen atom is included in the ring-forming atoms include azetidinyl, pyrrolidinyl, piperidinyl, piperazinyl, or morpholinyl.

The term "saturated heterocyclyl having four to six ring-forming atoms and optionally having an oxo group" means the above-described saturated heterocyclyl having four to six ring-forming atoms in which the two hydrogen atoms of a methylene group are optionally replaced by an oxo group, and the term includes, for example, azetidinyl, pyrrolidinyl, piperidinyl, oxetanyl, tetrahydrofuranyl, tetrahydropyranyl, piperazinyl, morpholinyl, 2-oxoazetidinyl, 2-oxopyrrolidinyl, 2-oxopiperidinyl, 2-oxooxetanyl, 2-oxotetrahydrofuranyl, 2-oxotetrahydropyranyl, 2-oxopiperazinyl, or 3-oxomorpholinyl.

The term "heteroaryl having five or six ring-forming atoms" means a monocyclic aromatic heterocyclyl group having a 5- or 6-membered ring which comprises the same or different one or more atoms selected from the group consisting of oxygen, sulfur and nitrogen, and one to five carbon atoms, and the term includes, for example, pyrrolyl, imidazolyl, pyrazolyl, triazolyl, tetrazolyl, oxazolyl, isooxazolyl, oxadiazolyl, thiazolyl, thiadiazolyl, pyridyl, pyrimidinyl, pyrazinyl, pyridazinyl, or triazinyl.

Specific examples of preferable urea derivatives represented by Formula (I) are indicated in Table 1, but this disclosure is not limited thereto.

TABLE 1

Structural Formula

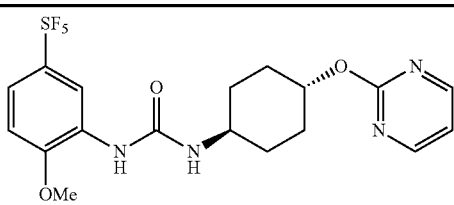

TABLE 1-continued
Structural Formula
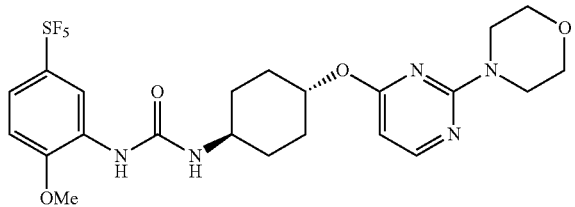
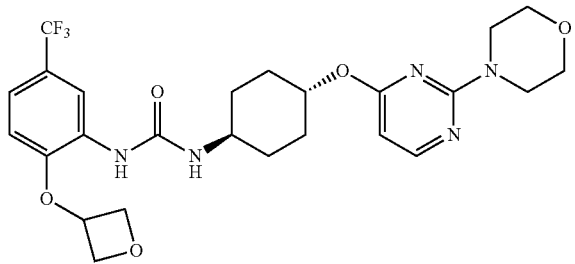 [SMILES: O=C(Nc1cc(C(F)(F)F)ccc1OC1COC1)N[C@H]1CC[C@H](Oc2ccnc(N3CCOCC3)n2)CC1]
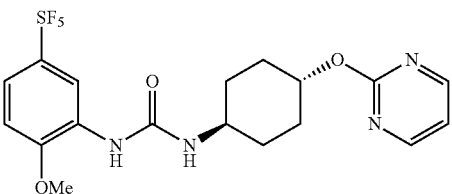
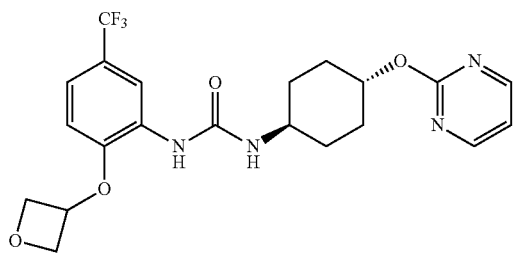 [SMILES: O=C(Nc1cc(C(F)(F)F)ccc1OC1COC1)N[C@H]1CC[C@H](Oc2ncccn2)CC1]
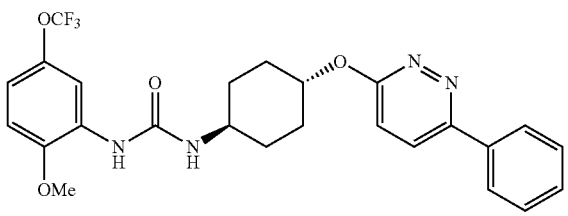 [SMILES: COc1ccc(OC(F)(F)F)cc1NC(=O)N[C@H]1CC[C@H](Oc2ccc(-c3ccccc3)nn2)CC1]
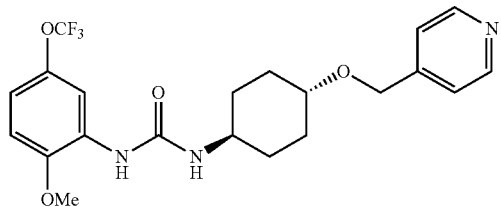
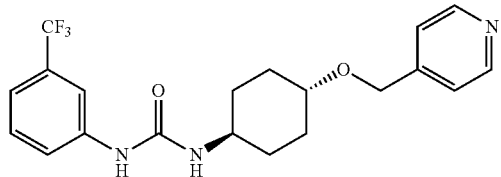 [SMILES: O=C(Nc1cccc(C(F)(F)F)c1)N[C@H]1CC[C@H](OCc2ccncc2)CC1]

TABLE 1-continued
Structural Formula
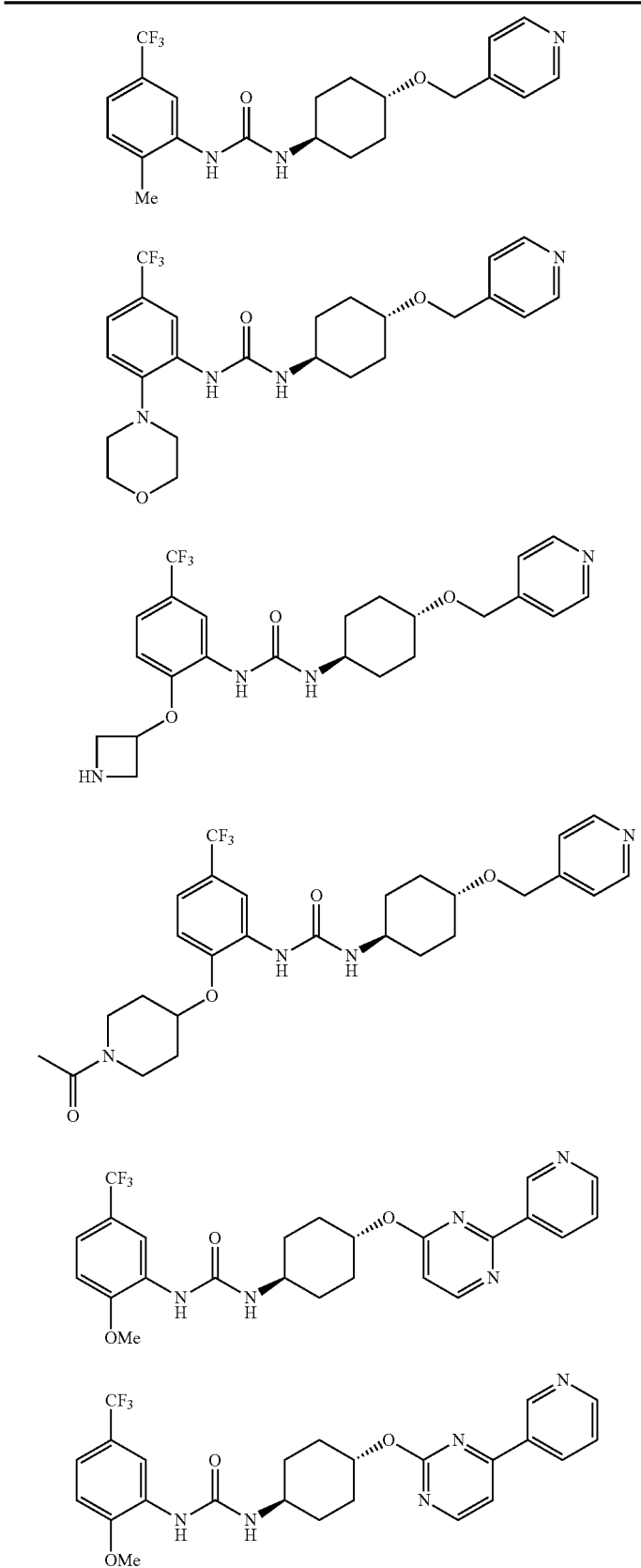

TABLE 1-continued

Structural Formula

TABLE 1-continued
Structural Formula
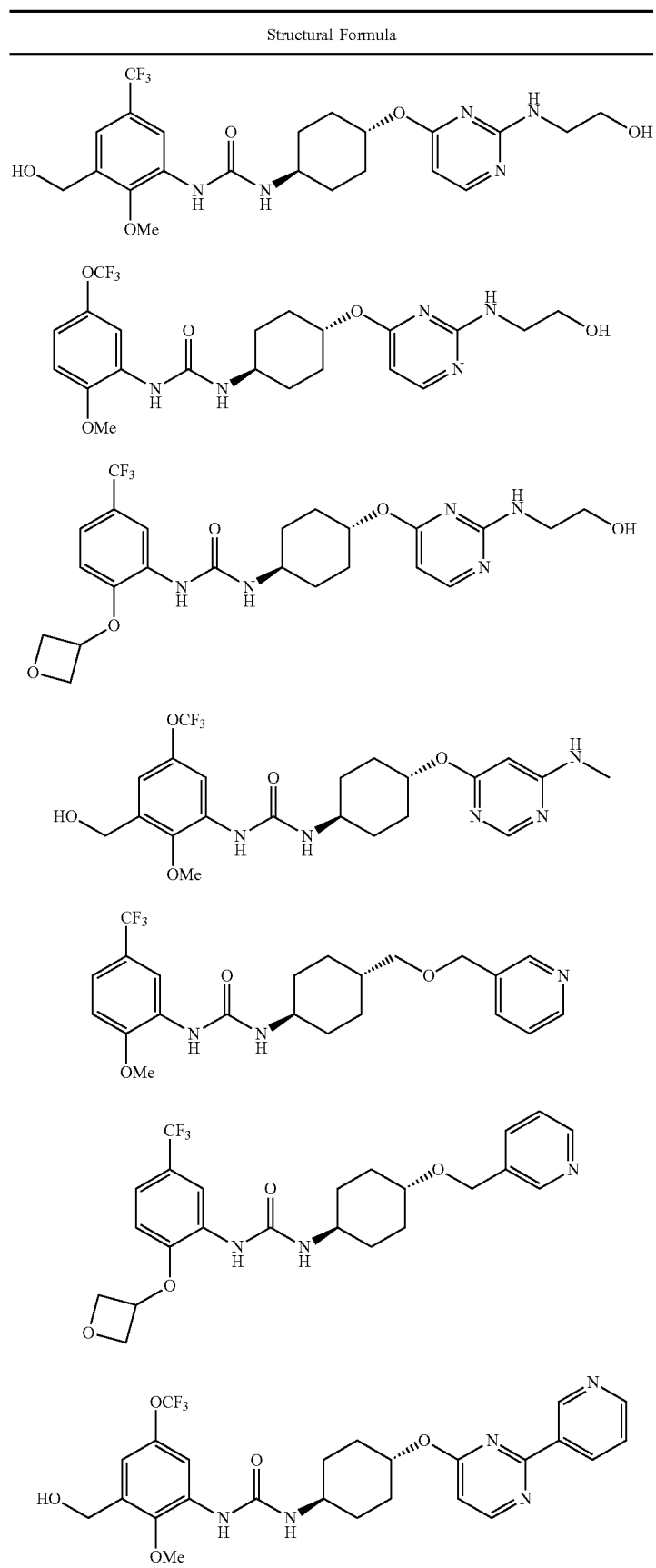

TABLE 1-continued

| Structural Formula |
| --- |

TABLE 1-continued
Structural Formula
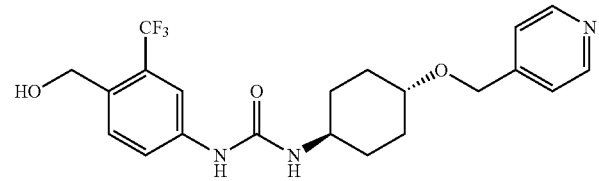 [SMILES: O=C(Nc1ccc(CO)c(C(F)(F)F)c1)N[C@H]1CC[C@H](OCc2ccncc2)CC1]
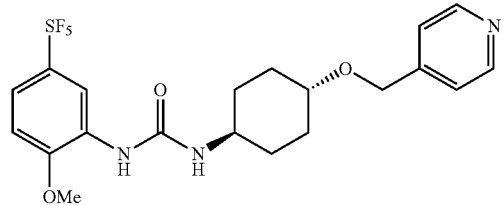
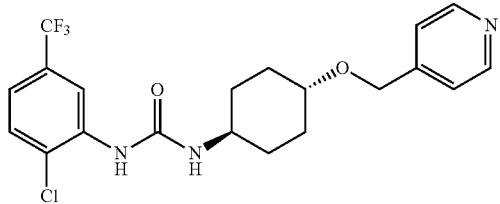 [SMILES: O=C(Nc1cc(C(F)(F)F)ccc1Cl)N[C@H]1CC[C@H](OCc2ccncc2)CC1]
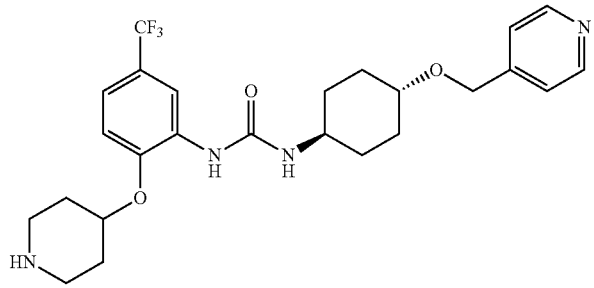 [SMILES: O=C(Nc1cc(C(F)(F)F)ccc1OC1CCNCC1)N[C@H]1CC[C@H](OCc2ccncc2)CC1]
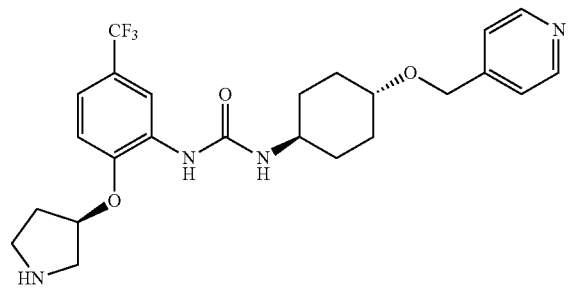 [SMILES: O=C(Nc1cc(C(F)(F)F)ccc1O[C@@H]1CCNC1)N[C@H]1CC[C@H](OCc2ccncc2)CC1]
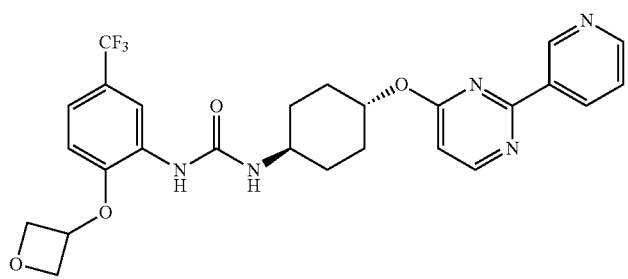 [SMILES: O=C(Nc1cc(C(F)(F)F)ccc1OC1COC1)N[C@H]1CC[C@H](Oc2ccnc(-c3cccnc3)n2)CC1]

TABLE 1-continued
Structural Formula
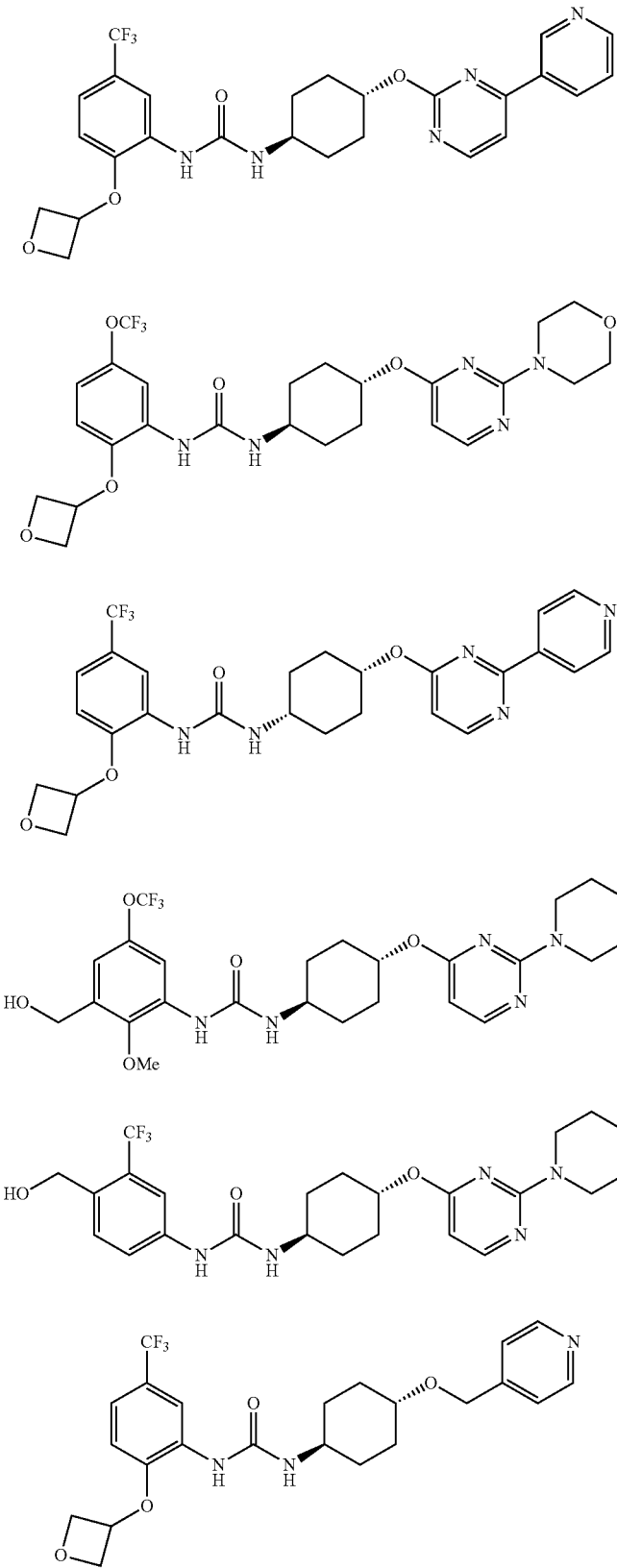

TABLE 1-continued
Structural Formula
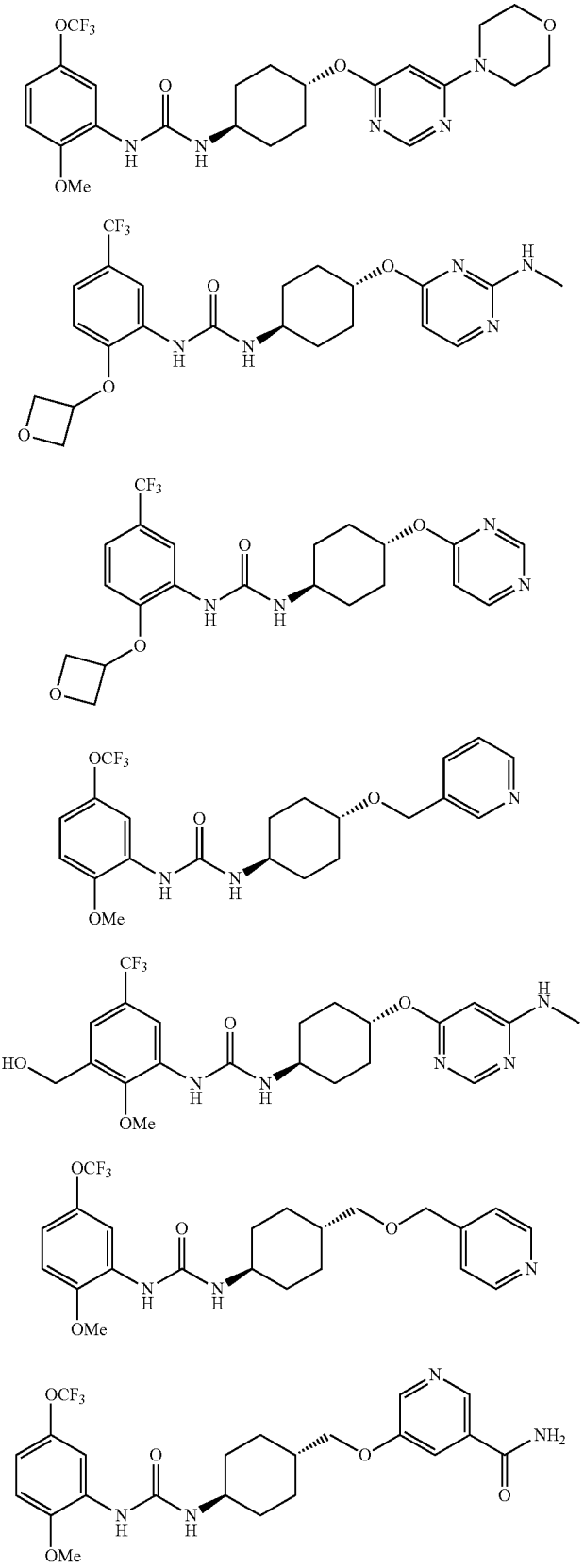

TABLE 1-continued

Structural Formula

TABLE 1-continued
Structural Formula
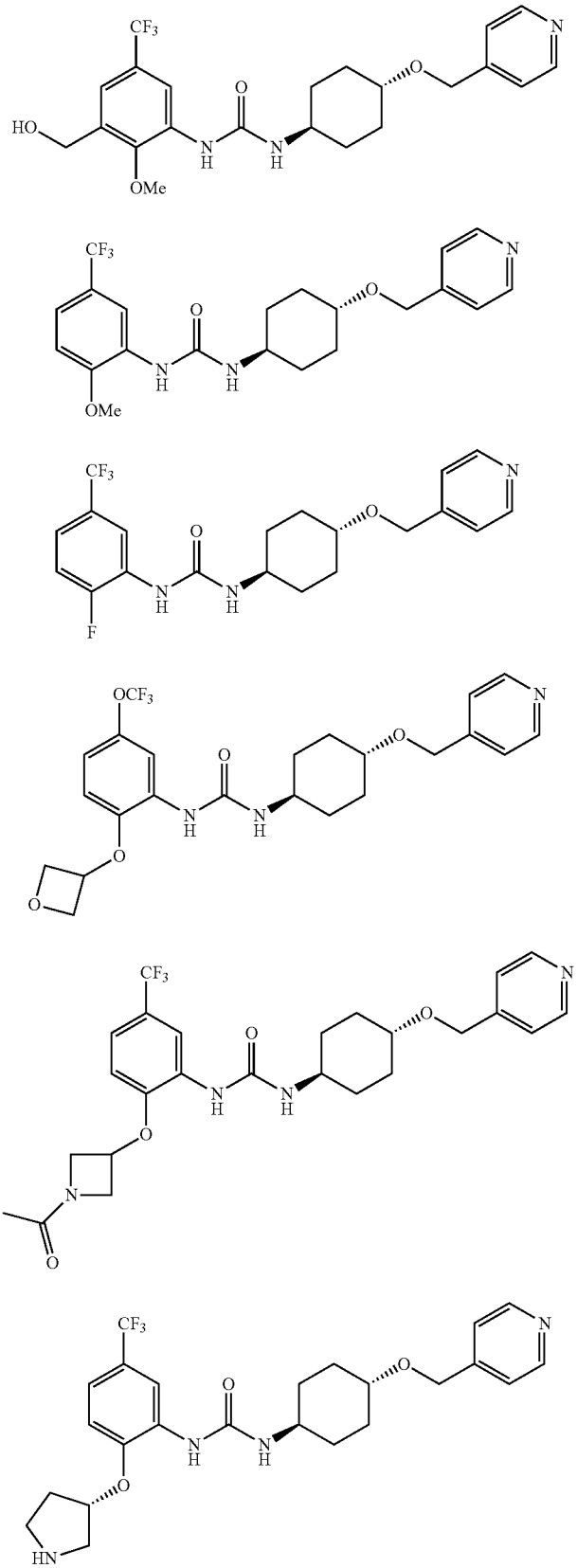

TABLE 1-continued
Structural Formula
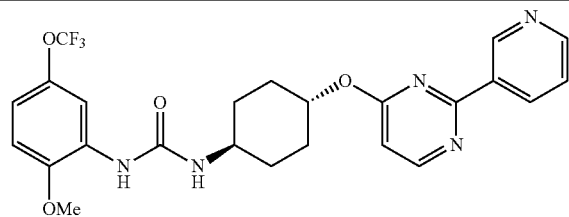
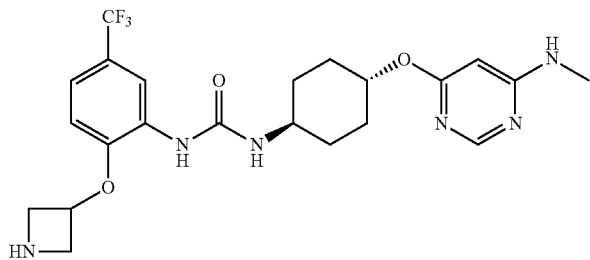 [SMILES: CNc1cc(O[C@H]2CC[C@H](NC(=O)Nc3cc(C(F)(F)F)ccc3OC3CNC3)CC2)ncn1]
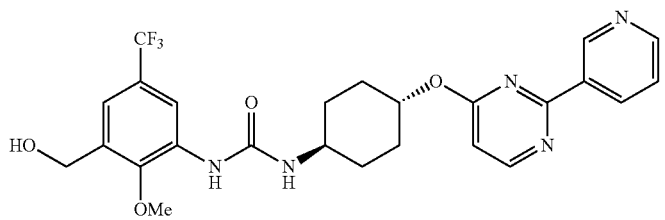 [SMILES: COc1c(CO)cc(C(F)(F)F)cc1NC(=O)N[C@H]1CC[C@H](Oc2ccnc(-c3cccnc3)n2)CC1]
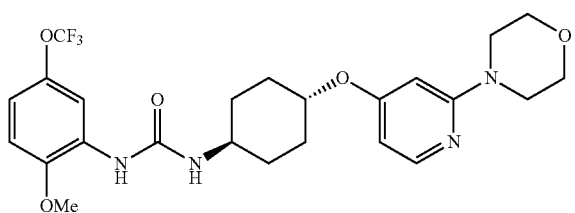 [SMILES: COc1ccc(OC(F)(F)F)cc1NC(=O)N[C@H]1CC[C@H](Oc2ccnc(N3CCOCC3)c2)CC1]
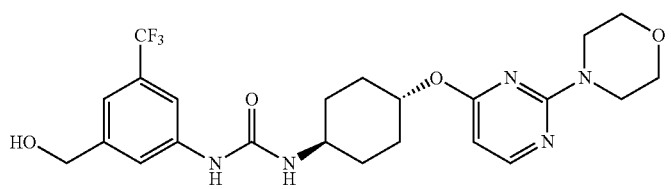 [SMILES: O=C(Nc1cc(CO)cc(C(F)(F)F)c1)N[C@H]1CC[C@H](Oc2ccnc(N3CCOCC3)n2)CC1]
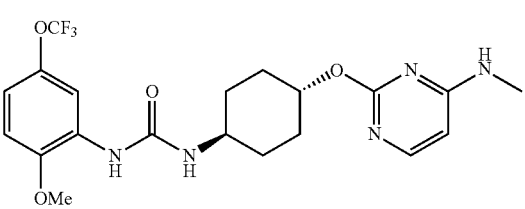
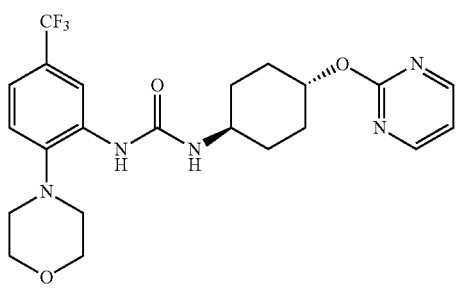 [SMILES: O=C(Nc1cc(C(F)(F)F)ccc1N1CCOCC1)N[C@H]1CC[C@H](Oc2ncccn2)CC1]

TABLE 1-continued
Structural Formula
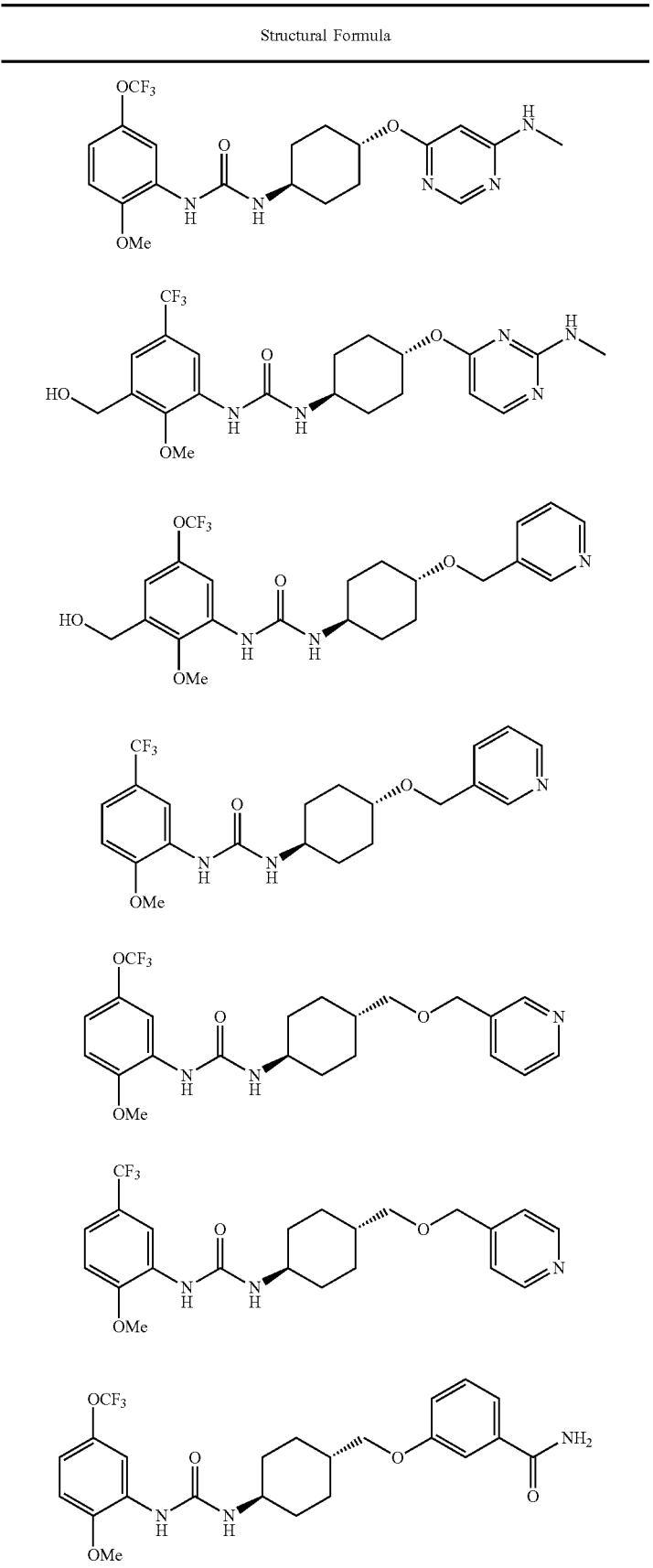

TABLE 1-continued

Structural Formula

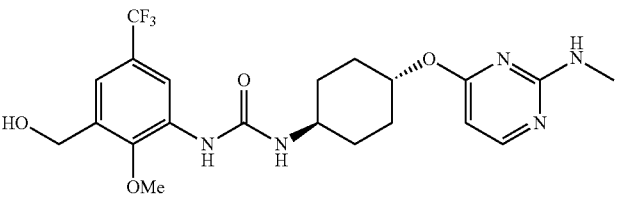

Optical isomers and diastereomers can exist for a urea derivative represented by Formula (I) (hereinafter referred to as urea derivative (I)), and the urea derivative includes racemic and diastereomeric mixtures as well as each single isomer.

We also provide a prodrug of the urea derivative (I) or a pharmaceutically acceptable salt thereof. The prodrug of the urea derivative (I) refers to a compound enzymatically or chemically converted in vivo to the urea derivative (I). The activity of a prodrug of the urea derivative (I) is attributable to the urea derivative (I) but the prodrug of the urea derivative (I) itself may have some activity.

Examples of a prodrug of the urea derivative (I) include compounds in which a hydroxyl group of the urea derivative (I) is substituted by alkyl, phosphate, or borate. These compounds can be synthesized from the urea derivative (I) according to known methods.

Moreover, the prodrug of the urea derivative (I) may be a prodrug converted to the urea derivative (I) under the conditions described in "Development of Pharmaceutical Product," Hirokawa Shoten Co., 1990, Vol. 7, pp. 163-198; and Progress in Medicine, 1985, Vol. 5, pp. 2157-2161.

The urea derivative (I) may be labeled with an isotope, and examples of the isotope used for labeling include $^2$H, $^3$H, $^{13}$C, $^{14}$C, $^{15}$N, $^{15}$O, $^{18}$O and/or $^{125}$I.

Examples of "pharmaceutically acceptable salts" of the urea derivative (I) include inorganic acid salts such as hydrochloride, sulfate, nitrate, hydrobromide, hydroiodide, or phosphate; or organic acid salts such as oxalate, malonate, citrate, fumarate, lactate, malate, succinate, tartrate, acetate, trifluoroacetate, maleate, gluconate, benzoate, ascorbate, glutarate, mandelate, phthalate, methanesulfonate, ethanesulfonate, benzenesulfonate, p-toluenesulfonate, camphorsulfonate, aspartate, glutamate, or cinnamate, and preferably include a hydrochloride, sulfate, hydrobromide, maleate, benzoate or methanesulfonate.

The urea derivative (I) or a pharmaceutically acceptable salt thereof may be an anhydrate or may have formed a solvate such as hydrate. The solvate herein is preferably a pharmaceutically acceptable solvate. The pharmaceutically acceptable solvate either may be or not may be a hydrate, but preferably it is a hydrate. Examples of the solvent constituent in the solvate include alcohol-based solvents such as methanol, ethanol, or n-propanol; N,N-dimethylformamide, dimethyl sulfoxide, or water.

Among the urea derivatives (I) and the compounds described in Reference Examples, those compounds with known configuration will be indicated as shown by Formula (IIIc) or (IIIb):

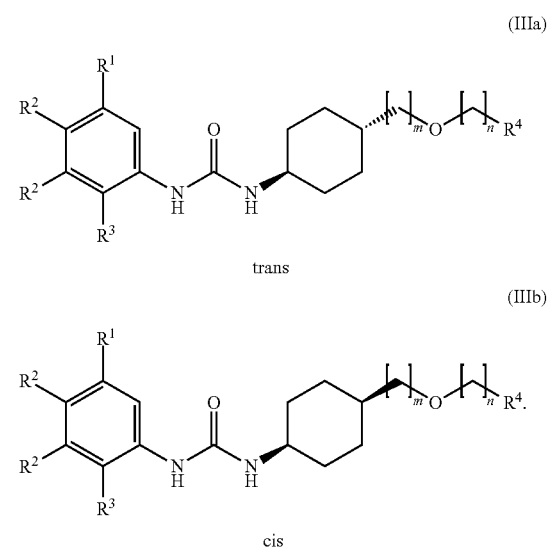

The configuration as shown by Formula (IIIa) is preferable for those of the urea derivatives (I) and the compounds described in Reference Examples.

The urea derivative (I) can be produced by an appropriate method based on its basic skeleton and features derived from the types of substituents. In addition, the starting materials and reagents used for the production of these compounds are generally commercially available or can be produced by known methods.

The urea derivative (I) as well as the intermediates and starting materials for use in the production of the derivative can be isolated and purified by known procedures. Examples of the known procedures for isolation and purification include solvent extraction, recrystallization, or chromatography.

If the urea derivative (I) includes optical isomers or stereoisomers, each isomer can be obtained as a single compound by known methods. Examples of the known methods include crystallization, enzymatic resolution, or chiral chromatography.

In the production method as described below, if any raw material compound has hydroxyl group, amino group, or carboxyl group, a protective group may be introduced to each of these groups in each reaction and a compound of interest can be obtained subsequent to the reaction by removing the protective group as necessary.

Examples of the protective group for hydroxyl group include trityl group, aralkyl group having 7 to 10 carbon atoms (for example, benzyl group), or substituted silyl group (for example, trimethylsilyl group, triethylsilyl group, or tert-butyldimethylsilyl group).

Examples of the protective group for amino group include alkylcarbonyl group having 2 to 6 carbon atoms (for example, acetyl group), benzoyl group, alkyloxycarbonyl group having 2 to 8 carbon atoms (for example, tert-butoxycarbonyl group or benzyloxycarbonyl group), aralkyl group having 7 to 10 carbon atoms (for example, benzyl group), or phthaloyl group.

Examples of the protective group for carboxyl group include alkyl group having 1 to 6 carbon atoms (for example, methyl group, ethyl group or tert-butyl group), or aralkyl group having 7 to 10 carbon atoms (for example, benzyl group).

Protective groups are removed in different ways depending on the type of the protective groups, but the deprotection may be performed according to a known method (for example, Greene, T. W., "Greene's Protective Groups in Organic Synthesis." Wiley-Interscience) or an equivalent method.

A urea derivative (I) can be obtained, for example, from an aniline derivative (IV) and a cyclohexanamine derivative (V) via urea coupling in the presence of a urea coupling agent and a base, as shown in Scheme 1:

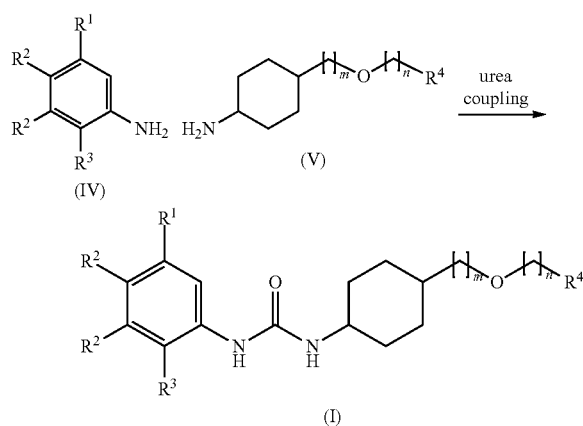

wherein each symbol is as defined above.

The aniline derivative (IV) for use in the urea coupling reaction can be produced by a known method or an equivalent method.

The cyclohexanamine derivative (V) for use in the urea coupling reaction is commercially available as a single isomer or a mixture of isomers as necessary. Moreover, it can also be produced by a known method or an equivalent method.

The amount of the cyclohexanamine derivative (V) for use in the urea coupling reaction is preferably 0.5 to 10 equivalents, more preferably 1 to 3 equivalents, to the aniline derivative (IV).

Examples of the urea coupling agent for use in the urea coupling reaction include chloroformate derivatives such as 2,2,2-trichloroethyl chloroformate, phenyl chloroformate, or p-nitrophenyl chloroformate; triphosgene, phosgene, N,N'-carbonyldiimidazole, or N,N'-disuccinimidyl carbonate, and preferably include chloroformate derivatives such as 2,2,2-trichloroethyl chloroformate, phenyl chloroformate, or p-nitrophenyl chloroformate; or triphosgene.

The amount of the urea coupling agent for use in the urea coupling reaction is preferably 0.1 to 100 equivalents, more preferably 0.3 to 30 equivalents, to the aniline derivative (IV).

Examples of the base for use in the urea coupling reaction include organic bases such as triethylamine or diisopropylethylamine; inorganic bases such as sodium hydrogen carbonate or potassium carbonate; metal hydride compounds such as sodium hydride, potassium hydride, or calcium hydride; alkyl lithium such as methyl lithium or butyl lithium; lithium amide such as lithium hexamethyldisilazide or lithium diisopropylamide; or a mixture thereof, and preferably include organic bases such as triethylamine or diisopropylethylamine.

The amount of the base for use in the urea coupling reaction is preferably 1 to 100 equivalents, more preferably 2 to 30 equivalents, to the aniline derivative (IV).

A reaction solvent for use in the urea coupling reaction is appropriately selected depending on the type of reagents to be used, but it is not particularly limited as long as the reaction is not inhibited. Examples of the reaction solvent include aprotic polar solvents such as N,N-dimethylformamide, N,N-dimethylacetamide, or dimethyl sulfoxide; ether-based solvents such as diethyl ether, tetrahydrofuran, dimethoxyethane, or 1,4-dioxane; ester-based solvents such as ethyl acetate or propyl acetate; chlorine-based solvents such as dichloromethane, chloroform, or 1,2-dichloroethane; nitrile-based solvents such as acetonitrile or propionitrile; or mixed solvents thereof, and preferably include chlorine-based solvents such as dichloromethane, chloroform, or 1,2-dichloroethane; or nitrile-based solvents such as acetonitrile or propionitrile.

The reaction temperature of the urea coupling reaction is preferably −40° C. to 200° C., more preferably −20° C. to 150° C.

The reaction time of the urea coupling reaction is appropriately selected depending on the conditions such as reaction temperature, and is preferably 30 minutes to 30 hours.

The concentration of the aniline derivative (IV) for use in the urea coupling reaction is preferably 1 mmol/L to 1 mol/L at the start of the reaction.

The aniline derivative (IV) can be obtained, for example, by reduction reaction of a nitrobenzene derivative (VI), as shown in Scheme 2:

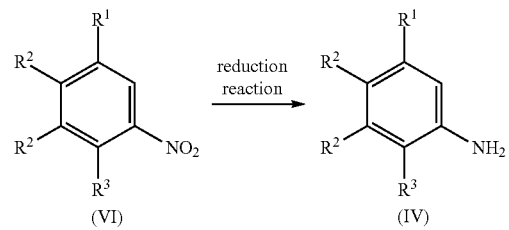

wherein each symbol is as defined above.

Examples of the reduction reaction include catalytic hydrogenation reaction under hydrogen atmosphere in the presence of a metal catalyst such as palladium, nickel, or platinum; hydride reduction reaction with a metal hydride reagent such as lithium aluminum hydride, borane-dimethylsulfide complex, or borane-tetrahydrofuran complex; or one-electron reduction reaction with a metal catalyst such as zinc, iron, or tin, in the presence of an acid, and preferably include catalytic hydrogenation reaction under hydrogen atmosphere in the presence of a metal catalyst such as palladium, nickel, or platinum; or one-electron reduction reaction with a metal catalyst such as zinc, iron, or tin, in the presence of an acid.

Examples of the metal catalyst for use in the catalytic hydrogenation reaction include palladium, nickel, platinum, or any of them on carbon support.

The amount of the metal catalyst for use in the catalytic hydrogenation reaction is preferably 0.001 to 5 equivalents, more preferably 0.01 to 1 equivalent, to the nitrobenzene derivative (VI).

A reaction solvent for use in the catalytic hydrogenation reaction is appropriately selected depending on the type of reagents to be used, but it is not particularly limited as long as the reaction is not inhibited. Examples of the reaction solvent include alcohol-based solvents such as methanol or ethanol; nitrile-based solvents such as acetonitrile or propionitrile; aprotic polar solvents such as N,N-dimethylformamide or N,N-dimethylacetamide; ether-based solvents such as diethyl ether, tetrahydrofuran, dimethoxyethane, or 1,4-dioxane; ester-based solvents such as ethyl acetate or propyl acetate; chlorine-based solvents such as dichloromethane, chloroform, or 1,2-dichloroethane; or mixed solvents thereof, and preferably include alcohol-based solvents such as methanol or ethanol.

The pressure of the hydrogen gas for use in the catalytic hydrogenation reaction is preferably 1 to 10 atmospheres, more preferably 1 to 3 atmospheres.

The reaction temperature of the catalytic hydrogenation reaction is preferably 0-200° C., more preferably 0-100° C.

The reaction time of the catalytic hydrogenation reaction is appropriately selected depending on the conditions such as reaction temperature, and is preferably from 1 to 72 hours.

Examples of the metal hydride reagent for use in the hydride reduction reaction include lithium aluminum hydride, borane-dimethylsulfide complex, or borane-tetrahydrofuran complex.

The amount of the metal hydride reagent for use in the hydride reduction reaction is preferably 0.1 to 20 equivalents, more preferably 0.1 to 10 equivalents, to the nitrobenzene derivative (VI).

A reaction solvent for use in the hydride reduction reaction is appropriately selected depending on the type of reagents to be used, but it is not particularly limited as long as the reaction is not inhibited. Examples of the reaction solvent include aromatic hydrocarbon-based solvents such as benzene, toluene, or xylene; ether-based solvents such as diethyl ether, tetrahydrofuran, dimethoxyethane, or 1,4-dioxane; or mixed solvents thereof, and preferably include ether-based solvents such as diethyl ether, tetrahydrofuran, dimethoxyethane, or 1,4-dioxane.

The reaction temperature of the hydride reduction reaction is preferably −78° C. to 150° C., more preferably −20° C. to 100° C.

The reaction time of the hydride reduction reaction is appropriately selected depending on the conditions such as reaction temperature, and is preferably 1 to 72 hours.

The concentration of the nitrobenzene derivative (VI) for use in the hydride reduction reaction is preferably 1 mmol/L to 1 mol/L at the start of the reaction.

Examples of the acid for use in the one-electron reduction reaction include acetic acid, hydrochloric acid, or ammonium chloride.

The amount of the acid for use in the one-electron reduction reaction is preferably 0.1 to 20 equivalents, more preferably 0.1 to 10 equivalents, to the nitrobenzene derivative (VI).

Examples of the metal catalyst for use in the one-electron reduction reaction include zinc, iron, tin, or a halide thereof.

The amount of the metal catalyst for use in the one-electron reduction reaction is preferably 0.1 to 100 equivalents, more preferably 1 to 50 equivalents, to the nitrobenzene derivative (VI).

A reaction solvent for use in the one-electron reduction reaction is appropriately selected depending on the type of reagents to be used, but it is not particularly limited as long as the reaction is not inhibited. Examples of the reaction solvent include acidic solvents such as hydrochloric acid or acetic acid; alcohol-based solvents such as methanol or ethanol; nitrile-based solvents such as acetonitrile or propionitrile; aprotic polar solvents such as N,N-dimethylformamide or N,N-dimethylacetamide; ether-based solvents such as diethyl ether, tetrahydrofuran, dimethoxyethane, or 1,4-dioxane; ester-based solvents such as ethyl acetate or propyl acetate; chlorine-based solvents such as dichloromethane, chloroform, or 1,2-dichloroethane; or mixed solvents thereof, and preferably include acidic solvents such as hydrochloric acid or acetic acid; or alcohol-based solvents such as methanol or ethanol.

The reaction temperature of the one-electron reduction reaction is preferably 0° C. to 200° C., more preferably 0° C. to 100° C.

The reaction time of the one-electron reduction reaction is appropriately selected depending on the conditions such as reaction temperature, and is preferably 1 to 72 hours.

The concentration of the nitrobenzene derivative (VI) for use in the reduction reaction is preferably 1 mmol/L to 1 mol/L at the start of the reaction.

The nitrobenzene derivative (VI) can be obtained, for example, by nucleophilic substitution reaction of a nitrobenzene derivative (VIA) with a nucleophile in the presence or absence of a base, as shown in Scheme 3:

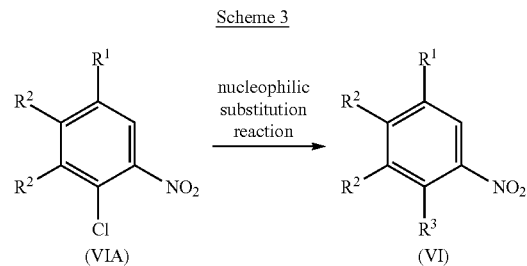

Scheme 3 wherein each symbol is as defined above.

The nucleophile for use in the nucleophilic substitution reaction is commercially available. Moreover, it can also be produced by a known method.

The amount of the nucleophile for use in the nucleophilic substitution reaction is preferably 0.2 to 10 equivalents, more preferably 0.5 to 3 equivalents, to the nitrobenzene derivative (VIA).

The nucleophilic substitution reaction may optionally be performed with a base. Examples of the base to be used include inorganic bases such as sodium hydride, sodium hydrogen carbonate, or potassium carbonate; organic bases such as triethylamine, diisopropylethylamine, or pyridine; or a mixture thereof.

The amount of the base for use in the nucleophilic substitution reaction is preferably 0.5 to 20 equivalents, more preferably 1 to 3 equivalents, to the nitrobenzene derivative (VIA).

A reaction solvent for use in the nucleophilic substitution reaction is appropriately selected depending on the type of reagents to be used, but it is not particularly limited as long as the reaction is not inhibited. Examples of the reaction solvent include alcohol-based solvents such as methanol or ethanol; nitrile-based solvents such as acetonitrile or propionitrile; aprotic polar solvents such as N,N-dimethylformamide, N,N-dimethylacetamide, or dimethyl sulfoxide; ether-based solvents such as diethyl ether, tetrahydrofuran, dimethoxyethane, or 1,4-dioxane; ester-based solvents such as ethyl acetate or propyl acetate; chlorine-based solvents such as dichloromethane, chloroform, or 1,2-dichloroethane; or mixed solvents thereof, and preferably include alcohol-based solvents such as methanol or ethanol; aprotic polar solvents such as N,N-dimethylformamide, N,N-dimethylacetamide, or dimethyl sulfoxide; or ether-based solvents such as diethyl ether, tetrahydrofuran, dimethoxyethane, or 1,4-dioxane.

The reaction temperature of the nucleophilic substitution reaction is preferably −20° C. to 200° C., more preferably 0-150° C.

The reaction time of the nucleophilic substitution reaction is appropriately selected depending on the conditions such as reaction temperature, and is preferably 1 to 60 hours.

The concentration of the nitrobenzene derivative (VIA) for use in the nucleophilic substitution reaction is preferably 1 mmol/L to 1 mol/L at the start of the reaction.

The cyclohexanamine derivative (V) can be obtained, for example, by deprotection of a cyclohexane derivative (VII), as shown in Scheme 4:

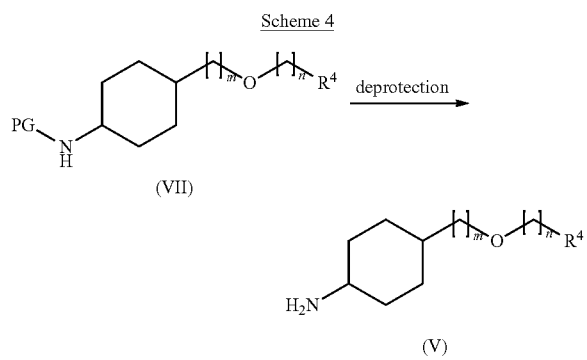

wherein PG is a protective group, and each of the other symbols is as defined above.

Protective groups are removed in different ways depending on the type of the protective groups, but the deprotection may be performed according to a known method (for example, Greene, T. W., "Greene's Protective Groups in Organic Synthesis," Wiley-Interscience) or an equivalent method.

Among cyclohexane derivatives (VII), a cyclohexane derivative (VIIA) in which m and n are 0 can be obtained, for example, by nucleophilic substitution reaction of an alcohol derivative (VIIIA) with a halogenated heteroaryl derivative (IX) in the presence or absence of a base, as shown in Scheme 5:

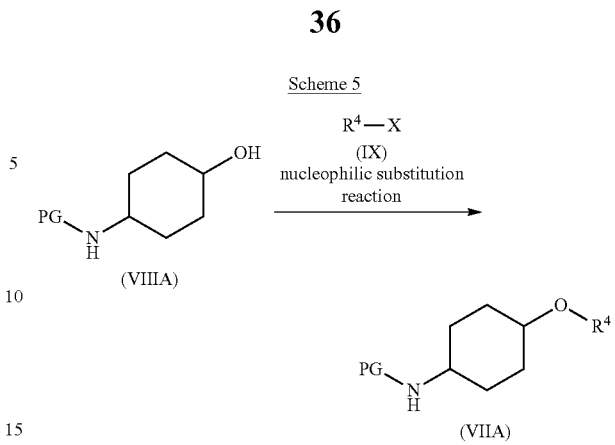

wherein X represents a halogen atom, and each of the other symbols is as defined above.

The alcohol derivative (VIIIA) for use in the nucleophilic substitution reaction is commercially available as a single isomer or a mixture of isomers as necessary. Moreover, it can also be produced by a known method or an equivalent method.

The halogenated heteroaryl derivative (IX) for use in the nucleophilic substitution is commercially available. Moreover, it can also be produced by a known method.

The amount of the halogenated heteroaryl derivative (IX) for use in the nucleophilic substitution reaction is preferably 0.2 to 10 equivalents, more preferably 0.5 to 3 equivalents, to the alcohol derivative (VIIIA).

The nucleophilic substitution reaction may optionally be performed with a base. Examples of the base to be used include inorganic bases such as sodium hydride, sodium hydrogen carbonate, or potassium carbonate; organic bases such as triethylamine, diisopropylethylamine, or pyridine; or a mixture thereof.

The amount of the base for use in the nucleophilic substitution reaction is preferably 0.5 to 20 equivalents, more preferably 1 to 3 equivalents, to the alcohol derivative (VIIIA).

A reaction solvent for use in the nucleophilic substitution is appropriately selected depending on the type of reagents to be used, but it is not particularly limited as long as the reaction is not inhibited. Examples of the reaction solvent include alcohol-based solvents such as methanol or ethanol; nitrile-based solvents such as acetonitrile or propionitrile; aprotic polar solvents such as N,N-dimethylformamide, N,N-dimethylacetamide, or dimethyl sulfoxide; ether-based solvents such as diethyl ether, tetrahydrofuran, dimethoxyethane, or 1,4-dioxane; ester-based solvents such as ethyl acetate or propyl acetate; chlorine-based solvents such as dichloromethane, chloroform, or 1,2-dichloroethane; or mixed solvents thereof, and preferably include alcohol-based solvents such as methanol or ethanol; aprotic polar solvents such as N,N-dimethylformamide, N,N-dimethylacetamide, or dimethyl sulfoxide; or ether-based solvents such as diethyl ether, tetrahydrofuran, dimethoxyethane, or 1,4-dioxane.

The reaction temperature of the nucleophilic substitution is preferably −20° C. to 200° C., more preferably 0-150° C.

The reaction time of the nucleophilic substitution is appropriately selected depending on the conditions such as reaction temperature, and is preferably 1 to 30 hours.

The concentration of the alcohol derivative (VIIIA) for use in the nucleophilic substitution is preferably 1 mmol/L to 1 mol/L at the start of the reaction.

Among cyclohexane derivatives (VII), a cyclohexane derivative (VIIB) in which m is 1 and n is 0 can be obtained, for example, by Mitsunobu reaction of an alcohol derivative (VIIIB) with an alcohol derivative (X) in the presence of an azo compound and an organic phosphorus compound, or by nucleophilic substitution reaction of the alcohol derivative (VIIIB) with a halogenated heteroaryl derivative (IX) in the presence or absence of a base, as shown in Scheme 6:

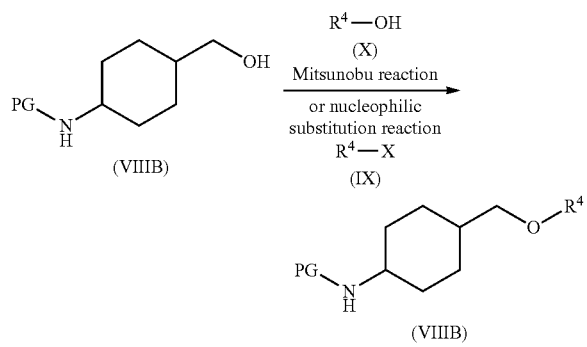

Scheme 6 wherein each symbol is as defined above.

The alcohol derivative (VIIIB) for use in the Mitsunobu reaction or nucleophilic substitution reaction is commercially available as a single isomer or a mixture of isomers as necessary. Moreover, it can also be produced by a known method or an equivalent method.

Examples of Mitsunobu reaction include a method in which an azo compound such as diethyl azodicarboxylate or diisopropyl azodicarboxylate and an organic phosphorus compound such as triphenylphosphine or tributylphosphine are used (see Chem. Rev. 2009, 109: 2551-2651).

The alcohol derivative (X), azo compound and organic phosphorus compound for use in the Mitsunobu reaction are commercially available. Moreover, they can also be produced by known methods.

The amount of the alcohol derivative (X) for use in the Mitsunobu reaction is preferably 0.5 to 20 equivalents, more preferably 1 to 5 equivalents, to the alcohol derivative (VIIIB).

Examples the azo compound for use in the Mitsunobu reaction include diethyl azodicarboxylate, diisopropyl azodicarboxylate, bis(2,2,2-trichloroethyl) azodicarboxylate, N,N,N',N'-tetramethylazodicarboxamide, bis(2-methoxyethyl) azodicarboxylate, or di(tert-butyl) azodicarboxylate.

The amount of the azo compound for use in the Mitsunobu reaction is preferably 0.5 to 20 equivalents, more preferably 1 to 5 equivalents, to the alcohol derivative (VIIIB).

Examples of the organic phosphorus compound for use in the Mitsunobu reaction include triphenylphosphine, tributylphosphine, or tricyclohexylphosphine.

The amount of the organic phosphorus compound for use in the Mitsunobu reaction is preferably 1 to 20 equivalents, more preferably 0.5 to 5 equivalents, to the alcohol derivative (VIIIB).

A reaction solvent for use in the Mitsunobu reaction is appropriately selected depending on the type of reagents to be used, but it is not particularly limited as long as the reaction is not inhibited. Examples of the reaction solvent include aromatic hydrocarbon-based solvents such as benzene, toluene, or xylene; nitrile-based solvents such as acetonitrile or propionitrile; aprotic polar solvents such as N,N-dimethylformamide, N,N-dimethylacetamide, or dimethyl sulfoxide; ether-based solvents such as diethyl ether, tetrahydrofuran, dimethoxyethane, or 1,4-dioxane; ester-based solvents such as ethyl acetate or propyl acetate; chlorine-based solvents such as dichloromethane, chloroform, or 1,2-dichloroethane; or mixed solvents thereof, and preferably include aromatic hydrocarbon-based solvents such as benzene, toluene, or xylene; or ether-based solvents such as diethyl ether or tetrahydrofuran.

The reaction temperature of the Mitsunobu reaction is preferably −20° C. to 200° C., more preferably 0° C. to 100° C.

The reaction time of the Mitsunobu reaction is appropriately selected depending on the conditions such as reaction temperature, and is preferably 1 to 30 hours.

The concentration of the alcohol derivative (VIIIB) for use in the Mitsunobu reaction is preferably 1 mmol/L to 1 mol/L at the start of the reaction.

The amount of the halogenated heteroaryl derivative (IX) for use in the nucleophilic substitution reaction is preferably 0.2 to 10 equivalents, more preferably 0.5 to 3 equivalents, to the alcohol derivative (VIIIB).

The nucleophilic substitution reaction may optionally be performed with a base. Examples of the base to be used include inorganic bases such as sodium hydride, sodium hydrogen carbonate, or potassium carbonate; organic bases such as triethylamine, diisopropylethylamine, or pyridine; or a mixture thereof.

The amount of the base for use in the nucleophilic substitution reaction is preferably 0.5 to 20 equivalents, more preferably 1 to 3 equivalents, to the alcohol derivative (VIIIB).

A reaction solvent for use in the nucleophilic substitution reaction is appropriately selected depending on the type of reagents to be used, but it is not particularly limited as long as the reaction is not inhibited. Examples of the reaction solvent include alcohol-based solvents such as methanol or ethanol; nitrile-based solvents such as acetonitrile or propionitrile; aprotic polar solvents such as N,N-dimethylformamide, N,N-dimethylacetamide, or dimethyl sulfoxide; ether-based solvents such as diethyl ether, tetrahydrofuran, dimethoxyethane, or 1,4-dioxane; ester-based solvents such as ethyl acetate or propyl acetate; chlorine-based solvents such as dichloromethane, chloroform, or 1,2-dichloroethane; or mixed solvents thereof, and preferably include alcohol-based solvents such as methanol or ethanol; aprotic polar solvents such as N,N-dimethylformamide, N,N-dimethylacetamide, or dimethyl sulfoxide; or ether-based solvents such as diethyl ether, tetrahydrofuran, dimethoxyethane, or 1,4-dioxane.

The reaction temperature of the nucleophilic substitution reaction is preferably −20° C. to 200° C., more preferably 0-150° C.

The reaction time of the nucleophilic substitution reaction is appropriately selected depending on the conditions such as reaction temperature, and is preferably 1 to 30 hours.

The concentration of the alcohol derivative (VIIIB) for use in the nucleophilic substitution reaction is preferably 1 mmol/L to 1 mol/L at the start of the reaction.

Among cyclohexane derivatives (VII), a cyclohexane (VIIC) in which n is 1 can be obtained, for example, by nucleophilic substitution reaction of the alcohol derivative (VIIIA) or (VIIIB) with a halogenated alkyl derivative (XI) in the presence or absence of a base, as shown in Scheme 7:

Scheme 7

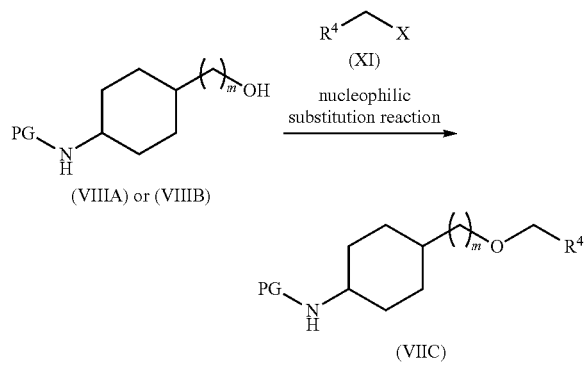

wherein each symbol is as defined above.

Each of the above-described alcohol derivatives (VIIIA) and (VIIIB) is commercially available as a single isomer or a mixture of isomers as necessary. Moreover, they can also be produced by known methods or equivalent methods.

The halogenated alkyl derivative (XI) for use in the nucleophilic substitution reaction is commercially available. Moreover, it can also be produced by a known method.

The amount of the halogenated alkyl derivative (XI) for use in the nucleophilic substitution reaction is preferably 0.2 to 10 equivalents, more preferably 0.5 to 3 equivalents, to the alcohol derivative (VIIIA) or (VIIIB).

The nucleophilic substitution reaction may optionally be performed with a base. Examples of the base to be used include inorganic bases such as sodium hydride, sodium hydrogen carbonate, or potassium carbonate; organic bases such as triethylamine, diisopropylethylamine, or pyridine; or a mixture thereof.

The amount of the base for use in the nucleophilic substitution reaction is preferably 0.5 to 20 equivalents, more preferably 1 to 3 equivalents, to the alcohol derivative (VIIIA) or (VIIIB).

A reaction solvent for use in the nucleophilic substitution reaction is appropriately selected depending on the type of reagents to be used, but it is not particularly limited as long as the reaction is not inhibited. Examples of the reaction solvent include alcohol-based solvents such as methanol or ethanol; nitrile-based solvents such as acetonitrile or propionitrile; aprotic polar solvents such as N,N-dimethylformamide, N,N-dimethylacetamide, or dimethyl sulfoxide; ether-based solvents such as diethyl ether, tetrahydrofuran, dimethoxyethane, or 1,4-dioxane; ester-based solvents such as ethyl acetate or propyl acetate; chlorine-based solvents such as dichloromethane, chloroform, or 1,2-dichloroethane; or mixed solvents thereof, and preferably include alcohol-based solvents such as methanol or ethanol; aprotic polar solvents such as N,N-dimethylformamide, N,N-dimethylacetamide, or dimethyl sulfoxide; or ether-based solvents such as diethyl ether, tetrahydrofuran, dimethoxyethane, or 1,4-dioxane.

The reaction temperature of the nucleophilic substitution reaction is preferably −20° C. to 200° C., more preferably 0-150° C.

The reaction time of the nucleophilic substitution reaction is appropriately selected depending on the conditions such as reaction temperature, and is preferably 1 to 30 hours.

The concentration of the alcohol derivative (VIIIA) or the alcohol derivative (VIIIB) for use in the nucleophilic substitution reaction is preferably 1 mmol/L to 1 mol/L at the start of the reaction.

Among cyclohexane derivatives (VIIA), a cyclohexane derivative (VIIA-b) in which $R^4$ is a halogenated heteroaryl can be obtained, for example, by nucleophilic substitution reaction of the alcohol derivative (VIIIA) with a dihalogenated heteroaryl derivative (XII) in the presence or absence of a base, as shown in Scheme 8:

Scheme 8

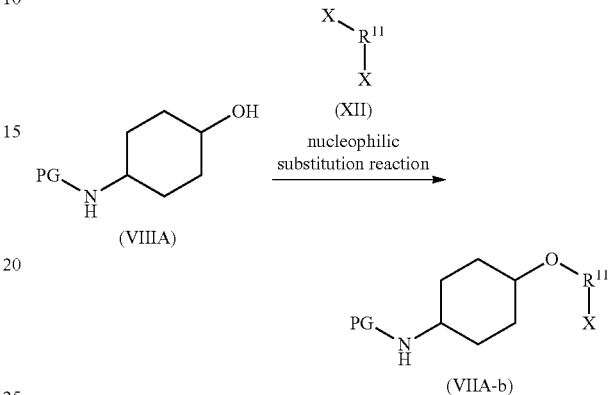

wherein X represents a halogen atom, $R^{11}$ is phenyl, pyridyl, pyridazinyl, or pyrimidinyl, and each of the other symbols is as defined above.

The alcohol derivative (VIIIA) for use in the nucleophilic substitution reaction is commercially available as a single isomer or a mixture of isomers as necessary. Moreover, it can also be produced by a known method or an equivalent method.

The dihalogenated heteroaryl derivative (XII) for use in the nucleophilic substitution reaction is commercially available. Moreover, it can also be produced by a known method.

The amount of the dihalogenated heteroaryl derivative (XII) for use in the nucleophilic substitution reaction is preferably 0.2 to 10 equivalents, more preferably 0.5 to 3 equivalents, to the alcohol derivative (VIIIA).

The nucleophilic substitution reaction may optionally be performed with a base. Examples of the base to be used include inorganic bases such as sodium hydride, sodium hydrogen carbonate, or potassium carbonate; organic bases such as triethylamine, diisopropylethylamine, or pyridine; or a mixture thereof.

The amount of the base for use in the nucleophilic substitution reaction is preferably 0.5 to 20 equivalents, more preferably 1 to 3 equivalents, to the alcohol derivative (VIIIA).

A reaction solvent for use in the nucleophilic substitution is appropriately selected depending on the type of reagents to be used, but it is not particularly limited as long as the reaction is not inhibited. Examples of the reaction solvent include alcohol-based solvents such as methanol or ethanol; nitrile-based solvents such as acetonitrile or propionitrile; aprotic polar solvents such as N,N-dimethylformamide, N,N-dimethylacetamide, or dimethyl sulfoxide; ether-based solvents such as diethyl ether, tetrahydrofuran, dimethoxyethane, or 1,4-dioxane; ester-based solvents such as ethyl acetate or propyl acetate; chlorine-based solvents such as dichloromethane, chloroform, or 1,2-dichloroethane; or mixed solvents thereof, and preferably include alcohol-based solvents such as methanol or ethanol; aprotic polar solvents such as N,N-dimethylformamide, N,N-dimethylacetamide, or dimethyl sulfoxide; or ether-based solvents such as diethyl ether, tetrahydrofuran, dimethoxyethane, or 1,4-dioxane.

The reaction temperature of the nucleophilic substitution reaction is preferably −20° C. to 200° C., more preferably 0-150° C.

The reaction time of the nucleophilic substitution reaction is appropriately selected depending on the conditions such as reaction temperature, and is preferably 1 to 30 hours.

The concentration of the alcohol derivative (VIIIA) for use in the nucleophilic substitution reaction is preferably 1 mmol/L to 1 mol/L at the start of the reaction.

Among cyclohexane derivatives (VII), a derivative represented by Formula (VIIA-a) can be obtained, for example, by nucleophilic substitution reaction or coupling reaction using the cyclohexane derivative (VIIA-b) in the presence or absence of a base, as shown in Scheme 9:

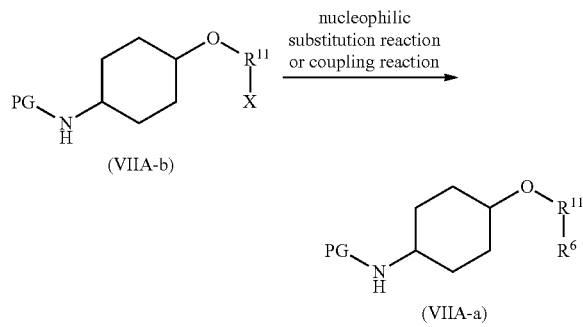

wherein each symbol is as defined above.

The above-described cyclohexane derivative (VIIA-b) can be obtained, for example, by nucleophilic substitution reaction of the alcohol derivative (VIIIA) with the halogenated heteroaryl derivative (IX) in the presence of a base, as shown in Scheme 5 described above.

The nucleophile for use in the nucleophilic substitution reaction is commercially available. Moreover, it can also be produced by a known method.

The amount of the nucleophile for use in the nucleophilic substitution is preferably 0.2 to 10 equivalents, more preferably 0.5 to 3 equivalents, to the cyclohexane derivative (VIIA-b).

The nucleophilic substitution reaction may optionally be performed with a base. Examples of the base to be used include inorganic bases such as sodium hydride, sodium hydrogen carbonate, or potassium carbonate; organic bases such as triethylamine, diisopropylethylamine, or pyridine; or a mixture thereof.

The amount of the base for use in the nucleophilic substitution reaction is preferably 0.5 to 20 equivalents, more preferably 1 to 3 equivalents, to the cyclohexane derivative (VIIA-b).

A reaction solvent for use in the nucleophilic substitution reaction is appropriately selected depending on the type of reagents to be used, but it is not particularly limited as long as the reaction is not inhibited. Examples of the reaction solvent include alcohol-based solvents such as methanol or ethanol; nitrile-based solvents such as acetonitrile or propionitrile; aprotic polar solvents such as N,N-dimethylformamide, N,N-dimethylacetamide, or dimethyl sulfoxide; ether-based solvents such as diethyl ether, tetrahydrofuran, dimethoxyethane, or 1,4-dioxane; ester-based solvents such as ethyl acetate or propyl acetate; chlorine-based solvents such as dichloromethane, chloroform, or 1,2-dichloroethane; or mixed solvents thereof, and preferably include alcohol-based solvents such as methanol or ethanol; aprotic polar solvents such as N,N-dimethylformamide, N,N-dimethylacetamide, or dimethyl sulfoxide; or ether-based solvents such as diethyl ether, tetrahydrofuran, dimethoxyethane, or 1,4-dioxane.

The reaction temperature of the nucleophilic substitution reaction is preferably −20° C. to 200° C., more preferably 0-150° C.

The reaction time of the nucleophilic substitution reaction is appropriately selected depending on the conditions such as reaction temperature, and is preferably 1 to 60 hours.

The concentration of the cyclohexane derivative (VIIA-b) for use in the nucleophilic substitution reaction is preferably 1 mmol/L to 1 mol/L at the start of the reaction.

Examples of the coupling reaction include a method in which an organometal compound such as an organomagnesium compound, an organozinc compound, or an organoboron compound and a halide such as a halogenated aryl, a halogenated heteroaryl, or a halogenated alkyl are used in the presence of a metal catalyst (see Angewante. Chem. Int. Ed., 2005, 44: 4442-4489).

The metal catalyst and organometal compound for use in the coupling reaction are commercially available. Moreover, they can also be produced by known methods or equivalent methods.

The amount of the organometal compound for use in the coupling reaction is preferably 0.5 to 20 equivalents, more preferably 1 to 3 equivalents, to the cyclohexane derivative (VIIA-b).

Examples of the metal catalyst for use in the coupling reaction include zero-valent palladium complex catalysts such as tetrakis(triphenylphosphine)palladium (0), tris (dibenzylideneacetone)dipalladium (0), or bis(dibenzylideneacetone)palladium (0), and preferably include tetrakis (triphenylphosphine)palladium (0).

The amount of the metal catalyst for use in the coupling reaction is preferably 0.001 to 10 equivalents, more preferably 0.01 to 1 equivalent, to the cyclohexane derivative (VIIA-b).

The coupling reaction may optionally be performed with a base. Examples of the base to be used include inorganic bases such as sodium hydroxide or sodium carbonate; metal alkyoxides such as sodium tert-butoxide or potassium tert-butoxide; carboxylic acid salts and the like such as sodium acetate or potassium acetate; or aqueous solutions thereof, and preferably include inorganic bases such as sodium hydroxide or sodium carbonate; or aqueous solutions thereof.

The amount of the base for use in the coupling reaction is preferably 0.5 to 100 equivalents, more preferably 1 to 30 equivalents, to the cyclohexane derivative (VIIA-b).

A reaction solvent for use in the coupling reaction is appropriately selected depending on the type of reagents to be used, but it is not particularly limited as long as the reaction is not inhibited. Examples of the reaction solvent include aromatic hydrocarbon-based solvents such as benzene or toluene; alcohol-based solvents such as methanol or ethanol; nitrile-based solvents such as acetonitrile or propionitrile; aprotic polar solvents such as N,N-dimethylformamide, N,N-dimethylacetamide, or dimethyl sulfoxide; ether-based solvents such as diethyl ether, tetrahydrofuran, dimethoxyethane, or 1,4-dioxane; ester-based solvents such as ethyl acetate or propyl acetate; chlorine-based solvents such as dichloromethane, chloroform, or 1,2-dichloroethane; or mixed solvents thereof, and preferably include aromatic solvents such as benzene or toluene; alcohol-based solvents such as methanol or ethanol; ether-based solvents such as diethyl ether, tetrahydrofuran, dimethoxyethane, or 1,4-dioxane; or mixed solvents thereof.

The reaction temperature of the coupling reaction is preferably 0° C. to 300° C., more preferably 20° C. to 200° C.

The reaction time of the coupling reaction is appropriately selected depending on the conditions such as reaction temperature, and is preferably 1 to 48 hours.

The concentration of the cyclohexane derivative (VIIA-b) for use in the coupling reaction is preferably 1 mmol/L to 1 mol/L at the start of the reaction.

Among urea derivatives (I), a urea derivative (IA-a) in which $R^4$ is $R^{11}$ substituted by one morpholinyl or $(R^7)R^8N$— can be obtained, for example, by urea coupling (Step 1) of the aniline derivative (IV) and a cyclohexanamine derivative (VA) in the presence of a urea coupling agent and a base, and nucleophilic substitution reaction (Step 2) of the resulting urea derivative (IA-b) with the nucleophile (IX) in the presence or absence of a base, as shown in Scheme 10:

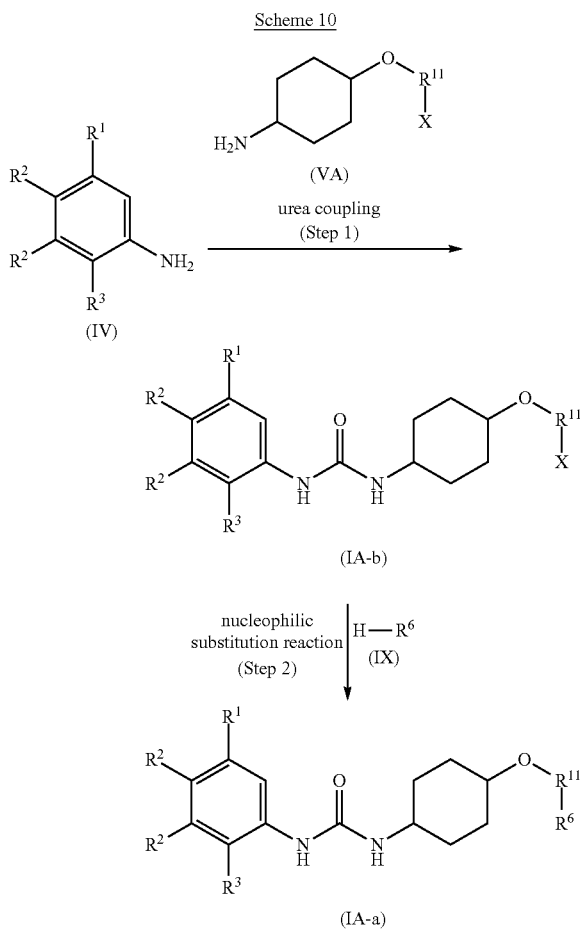

wherein each symbol is as defined above.

Step 1

The above-described cyclohexanamine derivative (VA) can be obtained, for example, by deprotection of the above-described cyclohexane derivative (VI), as shown in Scheme 4 described above.

The aniline derivative (IV) for use in the urea coupling reaction can be produced by a known method or an equivalent method.

The amount of the cyclohexanamine derivative (VA) for use in the urea coupling reaction is preferably 0.5 to 10 equivalents, more preferably 1 to 3 equivalents, to the aniline derivative (IV).

Examples of the urea coupling agent for use in the urea coupling reaction include chloroformate derivatives such as 2,2,2-trichloroethyl chloroformate, phenyl chloroformate, or p-nitrophenyl chloroformate; triphosgene, phosgene, N,N'-carbonyldiimidazole, or N,N'-disuccinimidyl carbonate, and preferably include triphosgene.

The amount of the urea coupling agent for use in the urea coupling reaction is preferably 0.1 to 100 equivalents, more preferably 0.3 to 30 equivalents, to the aniline derivative (IV).

Examples of the base for use in the urea coupling reaction include organic bases such as triethylamine or diisopropylethylamine; inorganic bases such as sodium hydrogen carbonate or potassium carbonate; metal hydride compounds such as sodium hydride, potassium hydride, or calcium hydride; alkyl lithium such as methyl lithium or butyl lithium; lithium amide such as lithium hexamethyldisilazide or lithium diisopropylamide; or a mixture thereof, and preferably include organic bases such as triethylamine or diisopropylethylamine.

The amount of the base for use in the urea coupling reaction is preferably 1 to 100 equivalents, more preferably 2 to 30 equivalents, to the aniline derivative (IV).

A reaction solvent for use in the urea coupling reaction is appropriately selected depending on the type of reagents to be used, but it is not particularly limited as long as the reaction is not inhibited. Examples of the reaction solvent include aprotic polar solvents such as N,N-dimethylformamide, N,N-dimethylacetamide, or dimethyl sulfoxide; ether-based solvents such as diethyl ether, tetrahydrofuran, dimethoxyethane, or 1,4-dioxane; ester-based solvents such as ethyl acetate or propyl acetate; chlorine-based solvents such as dichloromethane, chloroform, or 1,2-dichloroethane; nitrile-based solvents such as acetonitrile or propionitrile; or mixed solvents thereof, and preferably include chlorine-based solvents such as dichloromethane, chloroform, or 1,2-dichloroethane; or nitrile-based solvents such as acetonitrile or propionitrile.

The reaction temperature of the urea coupling reaction is preferably −40° C. to 200° C., more preferably −20° C. to 150° C.

The reaction time of the urea coupling reaction is appropriately selected depending on the conditions such as reaction temperature, and is preferably 30 minutes to 30 hours.

The concentration of the aniline derivative (IV) for use in the urea coupling reaction is preferably 1 mmol/L to 1 mol/L at the start of the reaction.

Step 2

The nucleophile (IX) for use in the nucleophilic substitution reaction is commercially available. Moreover, it can also be produced by a known method.

The amount of the nucleophile (IX) for use in the nucleophilic substitution reaction is preferably 0.2 to 10 equivalents, more preferably 0.5 to 3 equivalents, to the urea derivative (IA-b).

The nucleophilic substitution reaction may optionally be performed with a base. Examples of the base to be used include inorganic bases such as sodium hydride, sodium hydrogen carbonate, or potassium carbonate; organic bases such as triethylamine, diisopropylethylamine, or pyridine; or a mixture thereof.

The amount of the base for use in the nucleophilic substitution reaction is preferably 0.5 to 20 equivalents, more preferably 1 to 3 equivalents, to the urea derivative (IA-b).

A reaction solvent for use in the nucleophilic substitution reaction is appropriately selected depending on the type of reagents to be used, but it is not particularly limited as long as the reaction is not inhibited. Examples of the reaction solvent include alcohol-based solvents such as methanol or ethanol; nitrile-based solvents such as acetonitrile or propionitrile; aprotic polar solvents such as N,N-dimethylformamide, N,N-dimethylacetamide, or dimethyl sulfoxide; ether-based solvents such as diethyl ether, tetrahydrofuran, dimethoxyethane, or 1,4-dioxane; ester-based solvents such as ethyl acetate or propyl acetate; chlorine-based solvents such as dichloromethane, chloroform, or 1,2-dichloroethane; or mixed solvents thereof, and preferably include alcohol-based solvents such as methanol or ethanol; aprotic polar solvents such as N,N-dimethylformamide, N,N-dimethylacetamide, or dimethyl sulfoxide; or ether-based solvents such as diethyl ether, tetrahydrofuran, dimethoxyethane, or 1,4-dioxane.

The reaction temperature of the nucleophilic substitution reaction is preferably −20° C. to 200° C., more preferably 0-150° C.

The reaction time of the nucleophilic substitution reaction is appropriately selected depending on the conditions such as reaction temperature, and is preferably 1 to 60 hours.

The concentration of the urea derivative (IA-b) for use in the nucleophilic substitution is preferably 1 mmol/L to 1 mol/L at the start of the reaction.

The DDR1 inhibitor is characterized by comprising, as an active ingredient, the urea derivative (I) or a pharmaceutically acceptable salt thereof.

The term "DDR1 inhibitor" means a compound that inhibits the kinase activity of DDR1.

The urea derivative (I) or a pharmaceutically acceptable salt thereof has DDR1 inhibition activity and is thus expected to be a therapeutic agent against diseases, for example, cancer, with which improvement of the clinical state or amelioration of symptoms of the diseases is expected based on the corresponding mechanism of action.

Examples of "cancer" include pharynx cancer, larynx cancer, tongue cancer, non-small cell lung cancer, breast cancer, esophagus cancer, gastric cancer, colorectal cancer, uterine cancer, endometrial cancer, ovarian cancer, liver cancer, pancreatic cancer, gallbladder cancer, bile duct cancer, kidney cancer, renal pelvis and ureter cancer, bladder cancer, prostate cancer, malignant melanoma, thyroid cancer, neurogenic or osteogenic sarcoma, chondrosarcoma, rhabdomyosarcoma, angiosarcoma, fibrosarcoma, glioma, leukemia, malignant lymphoma, neuroblastoma, myeloma, or brain tumor.

The DDR1 inhibition activity of the urea derivative (I) or a pharmaceutically acceptable salt thereof can be evaluated with an in vitro study. Examples of the in vitro study include a method in which the kinase activity of DDR1 is evaluated based on measuring the amount of a phosphorylated substrate or consumed ATP (Analytical Biochemistry, 1999, 269: 94-104), and a method in which the binding of an assay target to DDR1 is measured (Journal of Biomolecular Screening, 2009, 14: 924-935). More specific examples of a method for the evaluation of DDR1 kinase activity include a method in which a purified intracellular domain protein of DDR1, a substrate peptide, and ATP are mixed and allowed to react and the amount of the phosphorylated substrate peptide is measured. The amount of the phosphorylated substrate peptide can be measured, for example, by measurement of fluorescence resonance energy transfer using the substrate peptide labeled in advance with biotin or a fluorescent substance.

EXAMPLES

Our derivatives, compounds and methods will be described in more details below by way of Examples and Reference Examples. However, this disclosure is not limited thereto.

For any compounds whose synthetic methods are not described in the context of the synthesis of the compounds of Examples, commercially available compounds were used. The names of solvents indicated in the NMR data represent the solvents used for the measurements. Moreover, 400 MHz NMR spectrum was measured using the JNM-AL400 nuclear magnetic resonance spectrometer (JEOL Ltd.) or the JNM-ECS400 nuclear magnetic resonance spectrometer (JEOL Ltd.). Chemical shifts were referenced to tetramethylsilane and expressed in δ (unit: ppm), while the multiplicity of each signal was expressed as s (singlet), d (doublet), t (triplet), q (quartet), m (multiplet), br (broad), dd (double-doublet), dt (double-triplet), ddd (double-double-doublet), dq (double-quartet), or tt (triple-triplet). ESI-MS spectrum was measured using the Agilent Technologies 1200 Series, G6130A (manufactured by Agilent Technology). All the used solvents were commercially available. The YFLC W-prep 2XH chromatograph (Yamazen Science, Inc.) was used for flash chromatography. The Monowave 300 manufactured by Anton Paar GmbH was used as a microwave synthesis reactor.

Raw materials and intermediates of urea derivatives (I) were synthesized by methods described in Reference Examples below. For any compounds whose synthetic methods are not described in the context of the synthesis of the compounds of Reference Examples, commercially available compounds were used.

Reference Example 1

Synthesis of tert-butyl trans-(4-hydroxycyclohexyl)carbamate

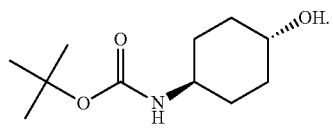

To a solution of trans-4-aminohexanol (10 g, 87 mmol) and triethylamine (18 mL, 0.13 mol) in dichloromethane (44 mL), di(tert-butyl) dicarbonate (21 g, 96 mmol) was added under cooling on ice. After stirring the obtained solution at room temperature for 6.5 hours, water and 1 N hydrochloric acid were added to the reaction solution, and the obtained solution was extracted with chloroform. The organic layer was dried over anhydrous sodium sulfate and then concentrated under vacuum. The obtained crude product was purified by recrystallization with a mixed solvent of hexane/ethyl acetate, and the precipitated solid was recovered by filtration to obtain the title compound (13 g).

$^1$H-NMR (400 MHz, CDCl$_3$) δ (ppm): 1.12-1.21 (2H, m), 1.33-1.44 (11H, m), 1.97-2.01 (4H, m), 3.40-3.43 (1H, m), 3.60-3.61 (1H, m), 4.33-4.35 (1H, m).

Reference Example 2

Synthesis of tert-butyl trans-(4-((2-chloropyrimidin-4-yl)oxy)cyclohexyl)carbamate and tert-butyl trans-(4-((4-chloropyrimidin-2-yl)oxy)cyclohexyl)carbamate

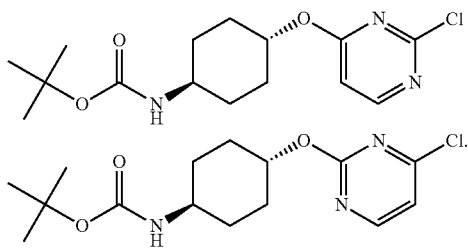

To a solution of tert-butyl trans-(4-hydroxycyclohexyl)carbamate (0.59 g, 2.7 mmol) in tetrahydrofuran (hereinafter referred to as THF) (10 mL), sodium hydride (55% by weight in mineral oil, 0.36 g) was added under cooling on ice. After stirring the obtained solution at room temperature for one and a half hours, a solution of 2,4-dichloropyrimidine (0.45 g, 3.0 mmol) in THF (5 mL) was added to the reaction solution. After stirring the obtained solution at 40° C. for two hours, the resulting solution was stirred at 60° C. for seven hours. Water was added to the reaction solution under cooling on ice, and the obtained solution was extracted with ethyl acetate. The organic layer was dried over anhydrous sodium sulfate and then concentrated under vacuum. The obtained crude product was purified by silica gel column chromatography (eluent; hexane:ethyl acetate=95:5→85:15) to obtain tert-butyl trans-(4-((2-chloropyrimidin-4-yl)oxy)cyclohexyl)carbamate (0.32 g) and tert-butyl trans-(4-((4-chloropyrimidin-2-yl)oxy)cyclohexyl)carbamate (0.17 g).

tert-butyl trans-(4-((2-chloropyrimidin-4-yl)oxy)cyclohexyl)carbamate $^1$H-NMR (400 MHz, CDCl$_3$) δ (ppm): 1.34 (2H, t, J=11.7 Hz), 1.45 (11H, s), 2.09-2.13 (4H, m), 3.50-3.53 (1H, m), 4.40-4.43 (1H, m), 5.07-5.09 (1H, m), 6.59 (1H, d, J=6.3 Hz), 8.26 (1H, d, J=6.3 Hz).

tert-butyl trans-(4-((4-chloropyrimidin-2-yl)oxy)cyclohexyl)carbamate $^1$H-NMR (400 MHz, CDCl$_3$) δ (ppm): 1.31-1.36 (2H, m), 1.44-1.46 (9H, m), 1.63-1.66 (2H, m), 2.10-2.16 (4H, m), 3.53 (1H, brs), 4.40 (1H, brs), 4.93-4.98 (1H, m), 6.95 (1H, d, J=5.1 Hz), 8.36 (1H, d, J=5.1 Hz).

Reference Example 3

Synthesis of trans-4-((2-chloropyrimidin-4-yl)oxy)cyclohexanamine hydrochloride

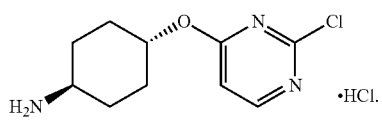 [SMILES: N[C@H]1CC[C@H](Oc2ccnc(Cl)n2)CC1]

A solution of tert-butyl trans-(4-((2-chloropyrimidin-4-yl)oxy)cyclohexyl)carbamate (0.33 g, 0.99 mmol) in a 4 N hydrogen chloride/ethyl acetate solution (2 mL) was stirred at room temperature for five hours. The reaction solution was concentrated under vacuum to obtain the title compound as a crude product.

Reference Example 4

Synthesis of 1-(trans-4-((2-chloropyrimidin-4-yl)oxy)cyclohexyl)-3-(2-methoxy-5-(trifluoromethoxy)phenyl)urea

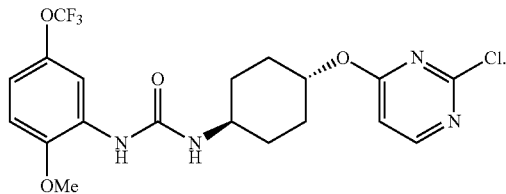 [SMILES: COc1ccc(OC(F)(F)F)cc1NC(=O)N[C@H]1CC[C@H](Oc2ccnc(Cl)n2)CC1]

To a solution of triphosgene (0.037 g, 0.13 mmol) in dichloromethane (3 mL), a solution of 2-methoxy-5-(trifluoromethoxy)aniline (0.79 g, 0.38 mmol) in dichloromethane (0.9 mL) and triethylamine (0.053 mL, 0.38 mmol) were added under cooling on ice. After stirring the reaction solution for one hour under cooling on ice, a solution of the crude product of trans-4-((2-chloropyrimidin-4-yl)oxy)cyclohexanamine hydrochloride (0.10 g) in N,N-dimethylformamide (hereinafter referred to as DMF) (0.6 mL) and triethylamine (0.26 mL, 1.9 mmol) were added thereto. After stirring the obtained solution at room temperature for one and a half hours, water was added to the reaction solution, and the obtained solution was extracted with chloroform. The organic layer was dried over anhydrous sodium sulfate and then concentrated under vacuum. The obtained crude product was purified by silica gel column chromatography (eluent; hexane:ethyl acetate=99:1→50:50) to obtain the title compound (0.015 g).

$^1$H-NMR (400 MHz, CDCl$_3$) δ (ppm): 1.35-1.40 (2H, m), 1.58-1.68 (2H, m), 2.16-2.18 (4H, m), 3.76-3.80 (1H, m), 3.88 (3H, s), 4.47 (1H, d, J=7.6 Hz), 5.08-5.14 (1H, m), 6.61 (1H, d, J=5.9 Hz), 6.79-6.81 (3H, m), 8.14 (1H, s), 8.27 (1H, d, J=5.9 Hz).

Example 1

Synthesis of 1-(2-methoxy-5-(trifluoromethoxy)phenyl)-3-(trans-4-((2-morpholinopyrimidin-4-yl)oxy)cyclohexyl)urea

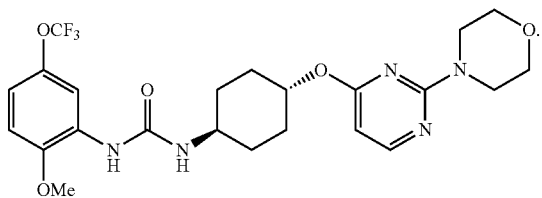

A solution of 1-(trans-4-((2-chloropyrimidin-4-yl)oxy)cyclohexyl)-3-(2-methoxy-5-(trifluoromethoxy)phenyl)urea (0.016 g, 0.034 mmol), morpholine (0.0032 g, 0.037 mmol) and sodium carbonate (0.068 g, 0.064 mmol) in ethanol (0.17 mL) was stirred at room temperature for one hour, and morpholine (0.010 g, 0.11 mmol) was then added to the reaction solution. After stirring the obtained solution overnight at room temperature, an aqueous solution of ammonium chloride was added to the reaction solution, and the obtained solution was extracted with ethyl acetate. The organic layer was sequentially washed with a saturated aqueous solution of sodium hydrogen carbonate and with a saturated aqueous solution of sodium chloride. The obtained organic layer was dried over anhydrous sodium sulfate and then concentrated under vacuum. The obtained crude product was purified by silica gel column chromatography (eluent; hexane:ethyl acetate=90:10→40:60) to obtain the title compound (0.0073 g) (hereinafter referred to as the compound of Example 1).

$^1$H-NMR (400 MHz, CDCl$_3$) δ (ppm): 1.24-1.39 (2H, m), 1.59-1.64 (2H, m), 2.15-2.17 (4H, m), 3.75 (9H, brs), 3.87 (3H, s), 4.52-4.54 (1H, m), 4.93-4.96 (1H, m), 5.97 (1H, d, J=5.6 Hz), 6.79-6.81 (3H, m), 8.06 (1H, d, J=5.6 Hz), 8.13 (1H, s).

MS(ESI) [M+H]$^+$: 512.

Example 2

Synthesis of 1-(2-methoxy-5-(trifluoromethoxy)phenyl)-3-(trans-4-(pyrimidin-4-yloxy)cyclohexyl)urea

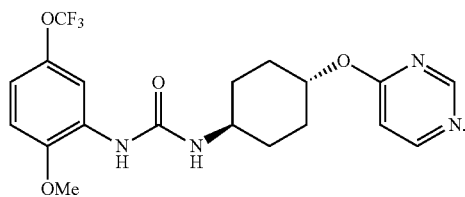 [SMILES: COc1ccc(OC(F)(F)F)cc1NC(=O)N[C@H]1CC[C@H](Oc2ccncn2)CC1]

A solution of 1-(trans-4-((2-chloropyrimidin-4-yl)oxy)cyclohexyl)-3-(2-methoxy-5-(trifluoromethoxy)phenyl)urea (0.020 g, 0.043 mmol), palladium (10% by weight) on carbon (containing 50% water by weight, 0.0046 g) and ammonium formate (0.0055 g, 0.087 mmol) in ethanol (0.33 mL) was stirred overnight at room temperature, and the reaction liquid was then filtered through Celite®, and the filtrate was concentrated under vacuum. The obtained crude product was purified by silica gel column chromatography (eluent; hexane:ethyl acetate=90:10→0:100) to obtain the title compound (0.014 g) (hereinafter referred to as the compound of Example 2).

$^1$H-NMR (400 MHz, CDCl$_3$) δ (ppm): 1.35-1.42 (2H, m), 1.56-1.66 (2H, m), 2.15-2.19 (4H, m), 3.76-3.80 (1H, m), 3.88 (3H, s), 4.45-4.49 (1H, m), 5.07-5.11 (1H, m), 6.68 (1H, d, J=6.0 Hz), 6.79-6.82 (3H, m), 8.14 (1H, s), 8.40 (1H, d, J=6.0 Hz), 8.74 (1H, s).

MS(ESI) [M+H]$^+$: 425.

Example 3

Synthesis of 1-(2-methoxy-5-(trifluoromethoxy)phenyl)-3-(trans-4-((2-(methylamino)pyrimidin-4-yl)oxy)cyclohexyl)urea

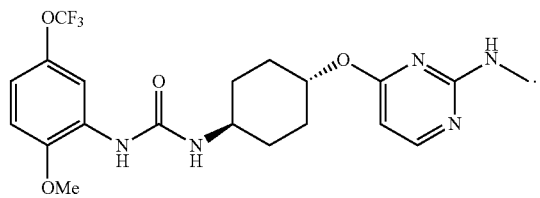 [SMILES: CNc1nccc(O[C@H]2CC[C@H](NC(=O)Nc3cc(OC(F)(F)F)ccc3OC)CC2)n1]

The title compound (0.010 g) (hereinafter referred to as the compound of Example 3) was obtained using a 1.0 N solution of methylamine in THF (0.20 mL) by a method similar to that for the synthesis of 1-(2-methoxy-5-(trifluoromethoxy)phenyl)-3-(trans-4-((2-morpholinopyrimidin-4-yl)oxy)cyclohexyl)urea (Example 1).

$^1$H-NMR (400 MHz, CD$_3$OD) δ (ppm): 1.37-1.40 (2H, m), 1.58-1.61 (2H, m), 2.06-2.15 (4H, m), 2.88 (3H, s), 3.61-3.64 (1H, m), 3.90 (3H, s), 4.59 (1H, brs), 5.06 (1H, brs), 5.97 (1H, d, J=5.9 Hz), 6.80 (1H, dd, J=9.1, 2.6 Hz), 6.96 (1H, d, J=8.8 Hz), 7.91 (1H, d, J=5.9 Hz), 8.09 (1H, d, J=2.9 Hz).

MS(ESI) [M+H]$^+$: 456.

Reference Example 5

Synthesis of 2-methoxy-3-nitro-5-(trifluoromethyl)benzaldehyde

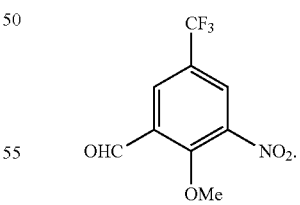

To a solution of 2-methoxy-5-(trifluoromethyl)benzaldehyde (3.0 g, 15 mmol) in concentrated sulfuric acid (44 mL), fuming nitric acid (0.79 mL) was added under cooling on ice. After stirring the reaction solution for one hour under cooling on ice, the reaction solution was poured into ice-cold water, and the obtained solution was extracted with ethyl acetate. The organic layer was washed with a saturated aqueous solution of sodium hydrogen carbonate, dried over anhydrous sodium sulfate, and then concentrated under vacuum. The obtained crude product was purified by silica gel column chromatography (eluent; hexane:ethyl acetate=99:1→90:10) to obtain the title compound (3.2 g).

$^1$H-NMR (400 MHz, CDCl$_3$) δ (ppm): 4.15 (3H, s), 8.33 (1H, d, J=2.2 Hz), 8.35 (1H, d, J=2.4 Hz), 10.43 (1H, s).

Reference Example 6

Synthesis of (2-methoxy-3-nitro-5-(trifluoromethyl)phenyl)methanol

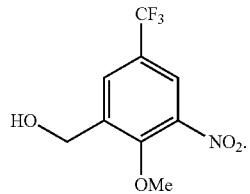 [SMILES: COc1c(CO)cc(C(F)(F)F)cc1[N+](=O)[O-]]

To a solution of 2-methoxy-3-nitro-5-(trifluoromethyl)benzaldehyde (2.0 g, 8.0 mmol) in methanol (40 mL), sodium borohydride (0.15 g, 4.0 mmol) was added under cooling on ice. After stirring the obtained solution for 10 minutes under cooling on ice, 1 N hydrochloric acid was added to the reaction solution, and the reaction solution was concentrated under vacuum. Water was added to the obtained crude product, and the obtained solution was extracted with ethyl acetate. The organic layer was dried over anhydrous sodium sulfate and then concentrated under vacuum. The obtained crude product was purified by silica gel column chromatography (eluent; hexane:ethyl acetate=90:10→75:25) to obtain the title compound (1.9 g).

$^1$H-NMR (400 MHz, CDCl$_3$) δ (ppm): 2.01 (1H, t, J=5.9 Hz), 3.98 (3H, s), 4.87 (2H, d, J=5.9 Hz), 8.01 (1H, d, J=1.8 Hz), 8.06 (1H, d, J=1.8 Hz).

Reference Example 7

Synthesis of (3-amino-2-methoxy-5-(trifluoromethyl)phenyl)methanol

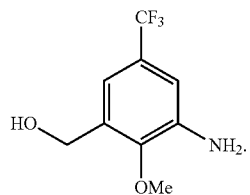 [SMILES: COc1c(N)cc(C(F)(F)F)cc1CO]

A solution of (2-methoxy-3-nitro-5-(trifluoromethyl)phenyl)methanol (1.0 g, 4.0 mmol), iron powder (1.1 g, 20 mmol) and ammonium chloride (1.1 g, 20 mmol) in a mixed solvent of ethanol/water (ethanol:water=2:1, v/v, 60 mL) was stirred at 90° C. for 1.5 hours, and the reaction liquid was then filtered through Celite®, and the filtrate was concentrated under vacuum. A saturated aqueous solution of sodium hydrogen carbonate was added to the obtained crude product, and the obtained solution was extracted with ethyl acetate. The organic layer was dried over anhydrous sodium sulfate and then concentrated under vacuum to obtain the title compound (0.84 g).

$^1$H-NMR (400 MHz, CDCl$_3$) δ (ppm): 1.96 (1H, s), 3.83 (3H, s), 3.97 (2H, s), 4.74 (2H, s), 6.95 (1H, d, J=1.4 Hz), 7.04 (1H, s).

MS(ESI) [M+H]$^+$: 222.

Reference Example 8

Synthesis of 2,2,2-trichloroethyl (3-(hydroxymethyl)-2-methoxy-5-(trifluoromethyl)phenyl)carbamate

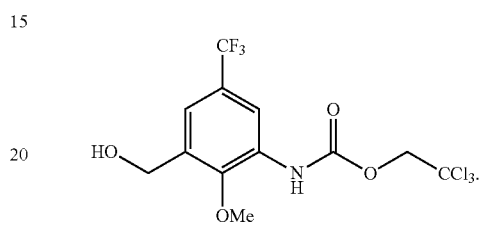

To a solution of (3-amino-2-methoxy-5-(trifluoromethyl)phenyl)methanol (0.84 g, 3.8 mmol) and diisopropylethylamine (hereinafter referred to as DIPEA) (0.99 mL, 5.7 mmol) in THF (38 mL), 2,2,2-trichloroethyl chloroformate (0.80 g, 3.8 mmol) was added under cooling on ice. After stirring the obtained solution at room temperature for 14 hours, 1 N hydrochloric acid was added to the reaction solution, and the obtained solution was extracted with ethyl acetate. The organic layer was dried over anhydrous sodium sulfate and then concentrated under vacuum. The obtained crude product was purified by silica gel column chromatography (eluent; hexane:ethyl acetate=90:10→65:35) to obtain the title compound (1.2 g).

$^1$H-NMR (400 MHz, CDCl$_3$) δ (ppm): 1.90 (1H, t, J=6.1 Hz), 3.89 (3H, s), 4.80 (2H, d, J=5.9 Hz), 4.87 (2H, s), 7.43 (1H, s), 7.46 (1H, d, J=1.4 Hz), 8.37 (1H, s).

Reference Example 9

Synthesis of 2-methoxy-3-nitro-5-(trifluoromethoxy)benzaldehyde

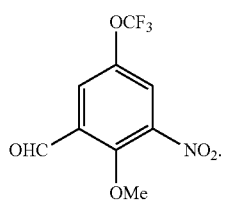 [SMILES: COc1c(C=O)cc(OC(F)(F)F)cc1[N+](=O)[O-]]

The title compound (21 g) was obtained using 2-methoxy-5-(trifluoromethoxy)benzaldehyde (25 g, 0.11 mol) by a method similar to that for the synthesis of 2-methoxy-3-nitro-5-(trifluoromethyl)benzaldehyde (Reference Example 5).

$^1$H-NMR (400 MHz, CDCl$_3$) δ (ppm): 4.11 (3H, s), 7.95-7.97 (2H, m), 10.40 (1H, t, J=3.5 Hz).

Reference Example 10

Synthesis of (2-methoxy-3-nitro-5-(trifluoromethoxy)phenyl)methanol

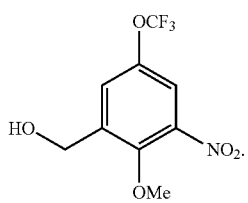 [SMILES: COc1c(CO)cc(OC(F)(F)F)cc1[N+](=O)[O-]]

The title compound (19 g) was obtained using 2-methoxy-3-nitro-5-(trifluoromethoxy)benzaldehyde (21 g, 0.081 mol) by a method similar to that for the synthesis of (2-methoxy-3-nitro-5-(trifluoromethyl)phenyl)methanol (Reference Example 6).

$^1$H-NMR (400 MHz, CDCl$_3$) δ (ppm): 2.01 (1H, t, J=5.9 Hz), 3.94 (3H, s), 4.84 (2H, d, J=5.6 Hz), 7.64-7.67 (2H, m).

Reference Example 11

Synthesis of (3-amino-2-methoxy-5-(trifluoromethoxy)phenyl)methanol

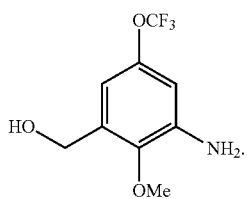 [SMILES: COc1c(N)cc(OC(F)(F)F)cc1CO]

The title compound (13 g) was obtained using (2-methoxy-3-nitro-5-(trifluoromethoxy)phenyl)methanol (19 g, 0.069 mol) by a method similar to that for the synthesis of (3-amino-2-methoxy-5-(trifluoromethyl)phenyl)methanol (Reference Example 7).

$^1$H-NMR (400 MHz, CDCl$_3$) δ (ppm): 1.97 (1H, t, J=6.2 Hz), 3.79 (3H, s), 3.92 (2H, s), 4.69 (2H, d, J=6.3 Hz), 6.56 (1H, s), 6.62 (1H, s).

Reference Example 12

Synthesis of 2,2,2-trichloroethyl (3-(hydroxymethyl)-2-methoxy-5-(trifluoromethoxy)phenyl)carbamate

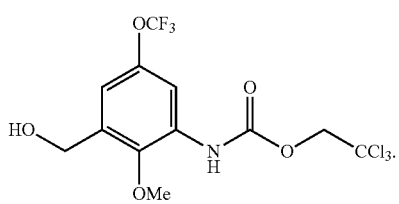

The title compound (11 g) was obtained using (2-methoxy-3-nitro-5-(trifluoromethoxy)phenyl)methanol (13 g, 0.057 mol) by a method similar to that for the synthesis of 2,2,2-trichloroethyl (3-(hydroxymethyl)-2-methoxy-5-(trifluoromethyl)phenyl)carbamate (Reference Example 8).

$^1$H-NMR (400 MHz, CDCl$_3$) δ (ppm): 1.89 (1H, t, J=6.0 Hz), 3.84 (3H, s), 4.77 (2H, d, J=5.9 Hz), 4.86 (2H, s), 7.05 (1H, s), 7.40 (1H, s), 8.00 (1H, s).

Reference Example 13

Synthesis of 1-methoxy-4-(pentafluorosulfanyl)benzene

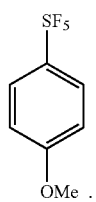

To a solution of 1-nitro-4-(pentafluorosulfanyl)benzene (20 g, 80 mmol) in DMF (100 mL), sodium methoxide (13 g, 24 mmol) was added over 30 minutes. After stirring the obtained solution at room temperature for one hour, water was added to the reaction solution, and the obtained solution was extracted with diethyl ether. The organic layer was dried over anhydrous sodium sulfate and then concentrated under vacuum. The obtained crude product was purified by silica gel column chromatography (eluent; hexane) to obtain the title compound (16 g).

$^1$H-NMR (400 MHz, CDCl$_3$) δ (ppm): 3.85 (3H, s), 6.91 (2H, d, J=9.6 Hz), 7.68 (2H, d, J=9.6 Hz).
MS(ESI) [M+H]$^+$: 235.

Reference Example 14

Synthesis of 2-methoxy-5-(pentafluorosulfanyl)benzaldehyde

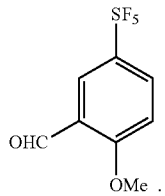

To a solution of 4-(pentafluorosulfanyl)anisole (1.3 g, 5.3 mmol) and dichloromethyl methyl ether (1.2 mL, 13 mmol) in dichloromethane (10 mL), titanium tetrachloride (1.5 mL, 13 mmol) was added over 10 minutes at −20° C. to keep the temperature of the reaction liquid within the range of −20 to −22° C. After stirring the obtained solution at −20° C. for 30 minutes, water was added to the reaction solution, and the obtained solution was extracted with dichloromethane. The organic layer was dried over anhydrous sodium sulfate and then concentrated under vacuum. The obtained crude product was purified by silica gel column chromatography (eluent; hexane:ethyl acetate=95:5→80:20) to obtain the title compound (0.52 g).

¹H-NMR (400 MHz, CDCl₃) δ (ppm): 4.02 (3H, s), 7.04-7.08 (1H, m), 7.90-7.95 (1H, m), 8.22-8.24 (1H, m), 10.5 (1H, s).
MS(ESI) [M+H]⁺: 263.

Reference Example 15

Synthesis of 2-methoxy-3-nitro-5-(pentafluorosulfanyl)benzaldehyde

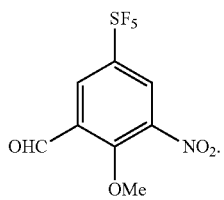

The title compound (0.070 g) was obtained using 2-methoxy-5-(pentafluorosulfanyl)benzaldehyde (0.10 g, 0.38 mol) by a method similar to that for the synthesis of 2-methoxy-3-nitro-5-(trifluoromethyl)benzaldehyde (Reference Example 5).
¹H-NMR (400 MHz, CDCl₃) δ (ppm): 4.15 (3H, s), 8.43-8.47 (2H, m), 10.4 (1H, s).
MS(ESI) [M+H]⁺: 308.

Reference Example 16

Synthesis of (2-methoxy-3-nitro-5-(pentafluorosulfanyl)phenyl)methanol

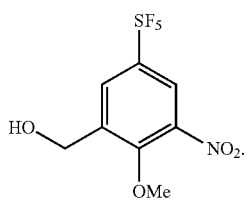

The title compound (0.067 g) was obtained using 2-methoxy-3-nitro-5-(pentafluorosulfanyl)benzaldehyde (0.070 g, 0.23 mmol) by a method similar to that for the synthesis of (2-methoxy-3-nitro-5-(trifluoromethyl)phenyl)methanol (Reference Example 6).
¹H-NMR (400 MHz, CDCl₃) δ (ppm): 3.97 (3H, s), 4.82-4.87 (2H, m), 8.12-8.21 (2H, m).
MS(ESI) [M+H]⁺: 310.

Reference Example 17

Synthesis of (3-amino-2-methoxy-5-(pentafluorosulfanyl)phenyl)methanol

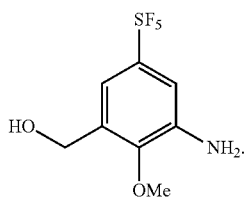

To a solution of (3-amino-2-methoxy-5-(pentafluorosulfanyl)phenyl)methanol (0.057 g, 0.18 mmol) in methanol (1 mL), platinum oxide (0.0042 g, 0.018 mmol) was added, and the obtained solution was stirred at room temperature for 30 minutes under hydrogen atmosphere. The reaction liquid was filtered through Celite® and the filtrate was concentrated under vacuum. The obtained crude product was purified by silica gel column chromatography (eluent; hexane: ethyl acetate=95:5→70:30) to obtain the title compound (0.049 g).
¹H-NMR (400 MHz, CDCl₃) δ (ppm): 3.82 (3H, s), 3.94-4.02 (2H, m), 4.71-4.74 (2H, m), 7.08-7.12 (1H, m), 7.16-7.20 (1H, m).
MS(ESI) [M+H]⁺: 280.

Reference Example 18

Synthesis of 2,2,2-trichloroethyl (3-(hydroxymethyl)-2-methoxy-5-(pentafluorosulfanyl)phenyl)carbamate

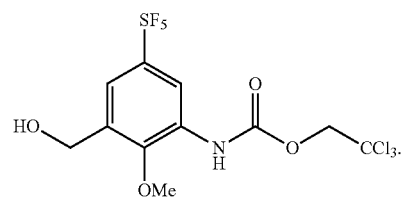

The title compound (0.071 g) was obtained using (3-amino-2-methoxy-5-(pentafluorosulfanyl)phenyl)methanol (0.049 g, 0.18 mmol) by a method similar to that for the synthesis of 2,2,2-trichloroethyl (3-(hydroxymethyl)-2-methoxy-5-(trifluoromethyl)phenyl)carbamate (Reference Example 8).
¹H-NMR (400 MHz, CDCl₃) δ (ppm): 3.88 (3H, s), 4.77-4.88 (4H, m), 7.37-7.47 (1H, m), 7.59-7.62 (1H, m), 8.46-8.58 (1H, m).
MS(ESI) [M+H]⁺: 455.

Reference Example 19

Synthesis of 4-(2-nitro-4-(trifluoromethyl)phenyl)piperazin-2-one

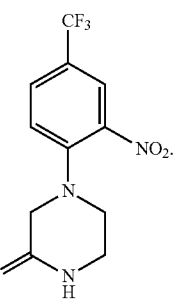

A solution of 1-chloro-2-nitro-4-(trifluoromethyl)benzene (0.30 g, 1.3 mmol), piperazin-2-one (0.17 mL, 1.7 mmol) and triethylamine (0.28 mL, 2.0 mmol) in dimethyl sulfoxide (hereinafter referred to as DMSO) (5 mL) was stirred for two hours, and water was then added to the reaction solution, and the obtained solution was extracted with ethyl acetate. The organic layer was dried over anhydrous sodium sulfate and then concentrated under vacuum. The obtained crude product was purified by silica gel column chromatography (eluent; hexane:ethyl acetate=95:5→0:100) to obtain 4-(2-nitro-4-(trifluoromethyl)phenyl)piperazin-2-one (0.32 g).

$^1$H-NMR (400 MHz, CDCl$_3$) δ (ppm): 3.38-3.39 (2H, m), 3.56-3.58 (2H, m), 3.91 (2H, d, J=3.7 Hz), 7.17-7.18 (1H, m), 7.72-7.75 (1H, m), 8.11-8.13 (1H, m).

Reference Example 20

Synthesis of 4-(2-amino-4-(trifluoromethyl)phenyl)piperazin-2-one

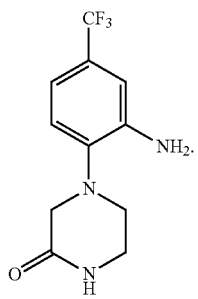 [SMILES: O=C1CN(c2ccc(C(F)(F)F)cc2[N+](=O)[O-])CCN1]

To a solution of 4-(2-nitro-4-(trifluoromethyl)phenyl)piperazin-2-one (0.15 g, 0.58 mol) in methanol (11 mL), palladium (10% by weight) on carbon (containing 50% water by weight, 0.062 g) was added at room temperature, and the obtained solution was stirred at room temperature for one hour under hydrogen atmosphere. The reaction liquid was filtered through Celite® and the filtrate was concentrated under vacuum to obtain the title compound (0.15 g).

$^1$H-NMR (400 MHz, CDCl$_3$) δ (ppm): 3.22-3.23 (2H, m), 3.47-3.50 (2H, m), 3.68 (2H, s), 4.09 (1H, s), 5.95 (1H, s), 6.97 (1H, s), 7.01 (2H, s).

Reference Example 21

Synthesis of 2,2,2-trichloroethyl (2-(3-oxopiperazin-1-yl)-5-(trifluoromethyl)phenyl)carbamate

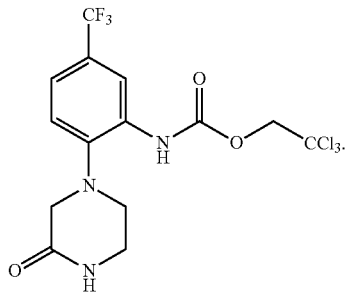

The title compound (0.17 g) was obtained using 4-(2-amino-4-(trifluoromethyl)phenyl)piperazin-2-one (0.15 g, 0.57 mmol) by a method similar to that for the synthesis of 2,2,2-trichloroethyl (3-(hydroxymethyl)-2-methoxy-5-(trifluoromethyl)phenyl)carbamate (Reference Example 8).

$^1$H-NMR (400 MHz, CDCl$_3$) δ (ppm): 3.18-3.20 (2H, m), 3.53-3.55 (2H, m), 3.67 (2H, s), 4.88 (2H, s), 6.01 (1H, s), 7.21-7.24 (1H, m), 7.38 (1H, d, J=8.3 Hz), 7.79 (1H, s), 8.40 (1H, s).

Reference Example 22

Synthesis of 2,2,2-trichloroethyl (2-(oxetan-3-yloxy)-5-(trifluoromethyl)phenyl)carbamate

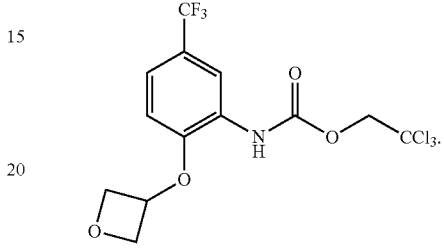

To a solution of 1-chloro-2-nitro-4-(trifluoromethyl)benzene (1.2 g, 5.2 mmol) in DMF, sodium hydride (55% by weight in mineral oil, 0.41 g) was added under cooling on ice. After stirring the obtained solution at room temperature for 30 minutes, oxetan-3-ol (3.2 g, 43 mmol) was added. After stirring the obtained solution overnight at room temperature, water was added to the reaction solution, and the obtained solution was extracted with ethyl acetate. The organic layer was sequentially washed with a saturated aqueous solution of ammonium chloride and with a saturated aqueous solution of sodium chloride. The obtained organic layer was dried over anhydrous sodium sulfate and then concentrated under vacuum, and a crude product was obtained. At room temperature, palladium (10% by weight) on carbon (containing 50% water by weight, 0.10 g) was added to a solution of the obtained crude product in methanol, and the obtained solution was stirred for five hours under hydrogen atmosphere. The reaction liquid was filtered through Celite® and the filtrate was concentrated under vacuum to obtain a crude product. To a solution of the obtained crude product and DIPEA (3.8 mL, 22 mmol) in THF, 2,2,2-trichloroethyl chloroformate (3.3 g, 16 mmol) was added under cooling on ice. After stirring the obtained solution overnight at room temperature, water was added to the reaction solution, and the obtained solution was extracted with ethyl acetate. The organic layer was sequentially washed with a saturated aqueous solution of ammonium chloride and with a saturated aqueous solution of sodium chloride. The obtained organic layer was dried over anhydrous sodium sulfate and then concentrated under vacuum. The obtained crude product was purified by recrystallization with a mixed solvent of hexane/diethyl ether, and the precipitated solid was recovered by filtration to obtain the title compound (3.8 g).

$^1$H-NMR (400 MHz, CDCl$_3$) δ (ppm): 4.83 (2H, dd, J=8.3, 5.1 Hz), 4.88 (2H, s), 5.05 (2H, dd, J=7.7, 6.7 Hz), 5.29-5.35 (1H, m), 6.49 (1H, d, J=8.5 Hz), 7.29 (1H, d, J=2.0 Hz), 7.46 (1H, s), 8.47 (1H, s).

MS(ESI) [M+H]$^+$: 408.

Reference Example 23

Synthesis of
1-chloro-2-nitro-4-(pentafluorosulfanyl)benzene

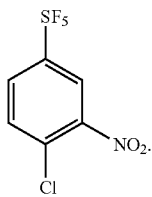

The title compound (5.9 g) was obtained using 1-chloro-4-(pentafluorosulfanyl)benzene (5.0 g, 21 mmol) by a method similar to that for the synthesis of 2-methoxy-3-nitro-5-(trifluoromethyl)benzaldehyde (Reference Example 5).

$^1$H-NMR (400 MHz, CDCl$_3$) δ (ppm): 7.71 (1H, d, J=8.6 Hz), 7.92 (1H, dd, J=8.6, 2.7 Hz), 8.31 (1H, d, J=2.7 Hz).

Reference Example 24

Synthesis of
3-(2-nitro-4-(pentafluorosulfanyl)phenoxy)oxetane

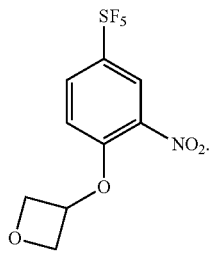

To a solution of oxetan-3-ol (94.0 mg, 1.27 mmol) in THF (1 mL), sodium hydride (55% by weight in mineral oil, 0.069 g) was added. After stirring the obtained solution at room temperature for 30 minutes, 1-chloro-2-nitro-4-(pentafluorosulfanyl)benzene (0.030 g, 1.1 mmol) was added to the reaction solution. After stirring the obtained solution at room temperature for four hours, water was added to the reaction solution, and the obtained solution was extracted with ethyl acetate. The organic layer was washed with a saturated aqueous solution of sodium chloride. The obtained organic layer was dried over anhydrous sodium sulfate and then concentrated under vacuum to obtain the title compound (0.34 g).

$^1$H-NMR (400 MHz, CD$_3$OD) δ (ppm): 4.72-4.75 (2H, m), 5.03-5.07 (2H, m), 5.52-5.57 (1H, m), 7.06 (1H, d, J=9.1 Hz), 8.04 (1H, dd, J=9.1, 2.8 Hz), 8.39 (1H, d, J=2.8 Hz).

MS(ESI) [M+H]$^+$: 322.

Reference Example 25

Synthesis of
2-(oxetan-3-yloxy)-5-(pentafluorosulfanyl)aniline

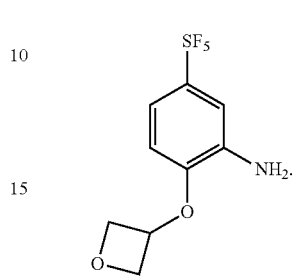

The title compound (0.31 g) was obtained using 3-(2-nitro-4-(pentafluorosulfanyl)phenoxy)oxetane (0.34 g, 1.1 mmol) by a method similar to that for the synthesis of 4-(2-amino-4-(trifluoromethyl)phenyl)piperazin-2-one (Reference Example 20).

$^1$H-NMR (400 MHz, CDCl$_3$) δ (ppm): 4.03 (2H, brs), 4.76-4.79 (2H, m), 4.99-5.03 (2H, m), 5.24-5.29 (1H, m), 6.30 (1H, d, J=8.8 Hz), 7.05 (1H, dd, J=8.8, 2.7 Hz), 7.12 (1H, d, J=2.7 Hz).

MS(ESI) [M+H]$^+$: 292.

Reference Example 26

Synthesis of 2,2,2-trichloroethyl (2-(oxetan-3-yloxy)-5-(pentafluorosulfanyl)phenyl)carbamate

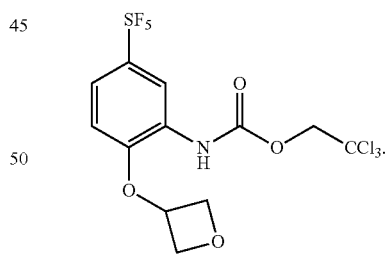

The title compound (0.32 g) was obtained using 2-(oxetan-3-yloxy)-5-(pentafluorosulfanyl)aniline (0.31 g, 1.1 mmol) by a method similar to that for the synthesis of 2,2,2-trichloroethyl (3-(hydroxymethyl)-2-methoxy-5-(trifluoromethyl)phenyl)carbamate (Reference Example 8).

$^1$H-NMR (400 MHz, CDCl$_3$) δ (ppm): 4.82 (2H, dd, J=8.3, 4.9 Hz), 4.88 (2H, s), 5.03-5.07 (2H, m), 5.30-5.35 (1H, m), 6.45 (1H, d, J=9.0 Hz), 7.42 (1H, dd, J=9.0, 2.7 Hz), 8.66 (1H, s).

MS(ESI) [M+H]$^+$: 466.

Reference Example 27

Synthesis of
1-methoxy-2-nitro-4-(pentafluorosulfanyl)benzene

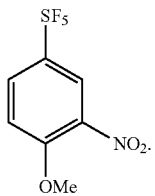

To a solution of 1-chloro-2-nitro-4-(pentafluorosulfanyl)benzene (3.0 g, 10 mmol) in THF (30 mL), a solution of sodium methoxide in methanol (28% by weight, 2.4 g, 13 mmol) was added under cooling on ice. After stirring the obtained solution at room temperature for two hours, a saturated aqueous solution of ammonium chloride was added to the reaction solution, and the obtained solution was extracted with dichloromethane. The organic layer was dried over anhydrous sodium sulfate and then concentrated under vacuum to obtain the title compound (2.5 g).

$^1$H-NMR (400 MHz, CDCl$_3$) δ (ppm): 4.04 (3H, s), 7.16 (1H, d, J=9.3 Hz), 7.94 (1H, dd, J=9.3, 2.7 Hz), 8.29 (1H, d, J=2.7 Hz).

MS(ESI) [M+H]$^+$: 280.

Reference Example 28

Synthesis of
2-methoxy-5-(pentafluorosulfanyl)aniline

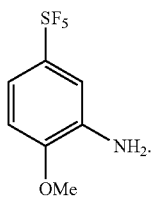

The title compound (0.45 g) was obtained using 1-methoxy-2-nitro-4-(pentafluorosulfanyl)benzene (0.34 g, 1.1 mmol) by a method similar to that for the synthesis of 4-(2-amino-4-(trifluoromethyl)phenyl)piperazin-2-one (Reference Example 20).

$^1$H-NMR (400 MHz, CDCl$_3$) δ (ppm): 3.90 (3H, s), 6.75 (1H, d, J=9.1 Hz), 7.09 (1H, d, J=2.7 Hz), 7.13 (1H, dd, J=9.1, 2.7 Hz).

MS(ESI) [M+H]$^+$: 250.

Reference Example 29

Synthesis of 2,2,2-trichloroethyl
(2-methoxy-5-(pentafluorosulfanyl)phenyl)carbamate

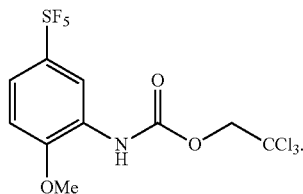

The title compound (5.0 g) was obtained using 2-methoxy-5-(pentafluorosulfanyl)aniline (4.5 g, 18 mmol) by a method similar to that for the synthesis of 2,2,2-trichloroethyl (3-(hydroxymethyl)-2-methoxy-5-(trifluoromethyl)phenyl)carbamate (Reference Example 8).

Reference Example 30

Synthesis of 2,2,2-trichloroethyl
(2-methoxy-5-(trifluoromethoxy)phenyl)carbamate

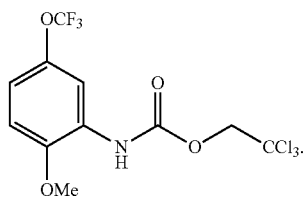

The title compound (7.0 g) was obtained using 2-methoxy-5-(trifluoromethoxy)aniline (5.0 g, 24 mmol) by a method similar to that for the synthesis of 2,2,2-trichloroethyl (3-(hydroxymethyl)-2-methoxy-5-(trifluoromethyl)phenyl)carbamate (Reference Example 8).

$^1$H-NMR (400 MHz, CDCl$_3$) δ (ppm): 3.92 (3H, s), 4.85 (2H, s), 6.86-6.91 (2H, m), 7.51 (1H, d, J=8.0 Hz), 8.08 (1H, s).

MS(ESI) [M+H]$^+$: 382.

Reference Example 31

Synthesis of 2,2,2-trichloroethyl
(2-methoxy-5-(trifluoromethyl)phenyl)carbamate

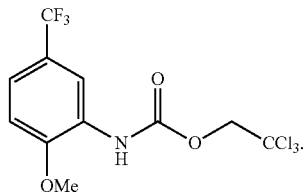

The title compound (7.8 g) was obtained using 2-methoxy-5-(trifluoromethyl)aniline (5.0 g, 26 mmol) by a method similar to that for the synthesis of 2,2,2-trichloroethyl (3-(hydroxymethyl)-2-methoxy-5-(trifluoromethyl)phenyl)carbamate (Reference Example 8).

$^1$H-NMR (400 MHz, CDCl$_3$) δ (ppm): 3.97 (3H, s), 4.86 (2H, s), 6.95 (1H, d, J=8.5 Hz), 7.33 (1H, dd, J=8.9, 1.8 Hz), 7.52 (1H, s), 8.42 (1H, s).

Reference Example 32

Synthesis of tert-butyl 4-(2-nitro-4-(trifluoromethyl)phenoxy)piperidine-1-carboxylate

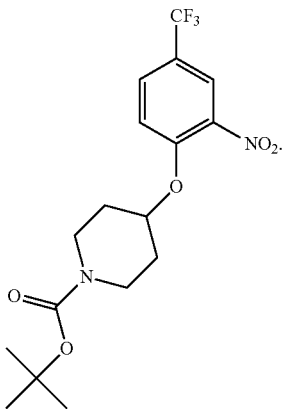 [SMILES: CC(C)(C)OC(=O)N1CCC(Oc2ccc(C(F)(F)F)cc2[N+](=O)[O-])CC1]

The title compound (0.11 g) was obtained using 1-chloro-2-nitro-4-(trifluoromethyl)benzene (0.10 g, 0.44 mmol) and tert-butyl 4-hydroxypiperidine-1-carboxylate (0.089 g, 0.044 mmol) by a method similar to that for the synthesis of tert-butyl trans-(4-((2-chloropyrimidin-4-yl)oxy)cyclohexyl)carbamate (Reference Example 2).

MS(ESI) [M−tBu]$^+$: 335.

Reference Example 33

Synthesis of tert-butyl 4-(2-amino-4-(trifluoromethyl)phenoxy)piperidine-1-carboxylate

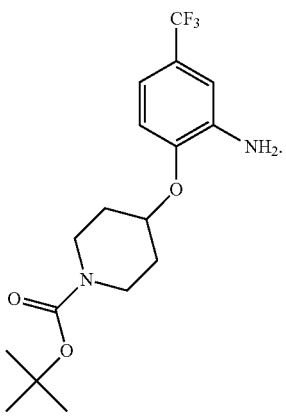 [SMILES: CC(C)(C)OC(=O)N1CCC(Oc2ccc(C(F)(F)F)cc2N)CC1]

The title compound (0.19 g) was obtained using tert-butyl 4-(2-nitro-4-(trifluoromethyl)phenoxy)piperidine-1-carboxylate (0.20 g, 0.51 mmol) by a method similar to that for the synthesis of 4-(2-amino-4-(trifluoromethyl)phenyl)piperazin-2-one (Reference Example 20).

MS(ESI) [M+H]$^+$: 437.

Reference Example 34

Synthesis of tert-butyl 4-(2-(((2,2,2-trichloroethoxy)carbonyl)amino)-4-(trifluoromethyl)phenoxy)piperidine-1-carboxylate

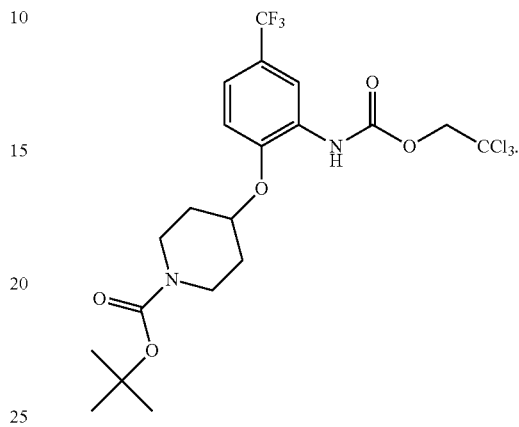

The title compound (0.13 g) was obtained using tert-butyl 4-(2-amino-4-(trifluoromethyl)phenoxy)piperidine-1-carboxylate (0.11 g, 0.30 mmol) by a method similar to that for the synthesis of 2,2,2-trichloroethyl (3-(hydroxymethyl)-2-methoxy-5-(trifluoromethyl)phenyl)carbamate (Reference Example 8).

MS(ESI) [M+H]$^+$: 534.

Reference Example 35

Synthesis of tert-butyl 3-(2-nitro-4-(trifluoromethyl)phenoxy)azetidine-1-carboxylate

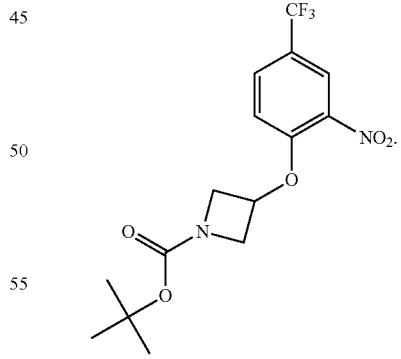

The title compound (0.12 g) was obtained using 1-chloro-2-nitro-4-(trifluoromethyl)benzene (0.10 g, 0.44 mmol) and tert-butyl 3-hydroxyazetidine-1-carboxylate (0.08 g, 0.44 mmol) by a method similar to that for the synthesis of tert-butyl trans-(4-((2-chloropyrimidin-4-yl)oxy)cyclohexyl)carbamate (Reference Example 2).

MS(ESI) [M−tBu]$^+$: 307.

Reference Example 36

Synthesis of (S)-tert-butyl 3-(2-nitro-4-(trifluoromethyl)phenoxy)pyrrolidine-1-carboxylate

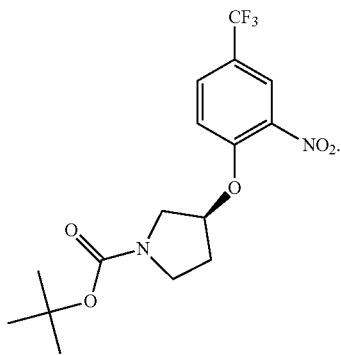 [SMILES: CC(C)(C)OC(=O)N1CC[C@H](Oc2ccc(C(F)(F)F)cc2[N+](=O)[O-])C1]

The title compound (0.62 g) was obtained using 1-chloro-2-nitro-4-(trifluoromethyl)benzene (0.50 g, 2.22 mmol) and (S)-tert-butyl 3-hydroxypyrrolidine-1-carboxylate (0.50 g, 2.66 mmol) by a method similar to that for the synthesis of tert-butyl trans-(4-((2-chloropyrimidin-4-yl)oxy)cyclohexyl)carbamate (Reference Example 2).

MS(ESI) [M−tBu]$^+$: 321.

Reference Example 37

Synthesis of (R)-tert-butyl 3-(2-nitro-4-(trifluoromethyl)phenoxy)pyrrolidine-1-carboxylate

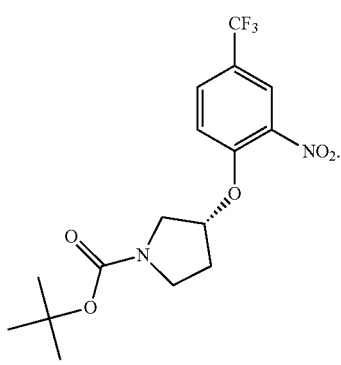 [SMILES: CC(C)(C)OC(=O)N1CC[C@@H](Oc2ccc(C(F)(F)F)cc2[N+](=O)[O-])C1]

The title compound (0.6 g) was obtained using 1-chloro-2-nitro-4-(trifluoromethyl)benzene (0.50 g, 2.22 mmol) and (R)-tert-butyl 3-hydroxypyrrolidine-1-carboxylate (0.50 g, 2.66 mmol) by a method similar to that for the synthesis of tert-butyl trans-(4-((2-chloropyrimidin-4-yl)oxy)cyclohexyl)carbamate (Reference Example 2).

MS(ESI) [M−tBu]$^+$: 321.

Reference Example 38

Synthesis of tert-butyl 3-(2-amino-4-(trifluoromethyl)phenoxy)azetidine-1-carboxylate

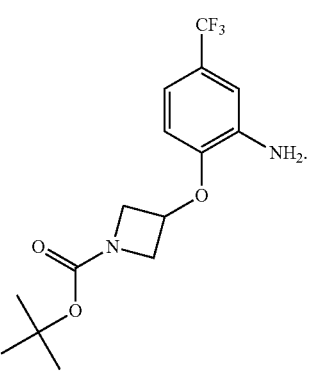 [SMILES: CC(C)(C)OC(=O)N1CC(Oc2ccc(C(F)(F)F)cc2N)C1]

The title compound (0.15 g) was obtained using tert-butyl 3-(2-nitro-4-(trifluoromethyl)phenoxy)azetidine-1-carboxylate (0.19 g, 0.51 mmol) by a method similar to that for the synthesis of 4-(2-amino-4-(trifluoromethyl)phenyl)piperazin-2-one (Reference Example 20).

MS(ESI) [M−tBu]$^+$: 277.

Reference Example 39

Synthesis of (S)-tert-butyl 3-(2-amino-4-(trifluoromethyl)phenoxy)pyrrolidine-1-carboxylate

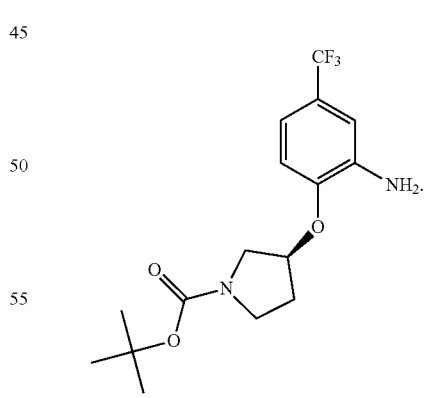

The title compound (0.5 g) was obtained using (S)-tert-butyl 3-(2-nitro-4-(trifluoromethyl)phenoxy)pyrrolidine-1-carboxylate (0.62 g, 1.65 mmol) by a method similar to that for the synthesis of 4-(2-amino-4-(trifluoromethyl)phenyl)piperazin-2-one (Reference Example 20). MS(ESI) [M−tBu]$^+$: 291.

Reference Example 40

Synthesis of (R)-tert-butyl 3-(2-amino-4-(trifluoromethyl)phenoxy)pyrrolidine-1-carboxylate

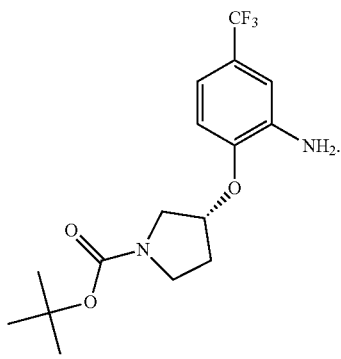

The title compound (0.51 g) was obtained using (R)-tert-butyl 3-(2-nitro-4-(trifluoromethyl)phenoxy)pyrrolidine-1-carboxylate (0.61 g, 1.62 mmol) by a method similar to that for the synthesis of 4-(2-amino-4-(trifluoromethyl)phenyl)piperazin-2-one (Reference Example 20).

MS(ESI) [M−tBu]$^+$: 291.

Reference Example 41

Synthesis of tert-butyl 3-(2-(((2,2,2-trichloroethyl)carbonyl)amino)-4-(trifluoromethyl)phenoxy)azetidine-1-carboxylate

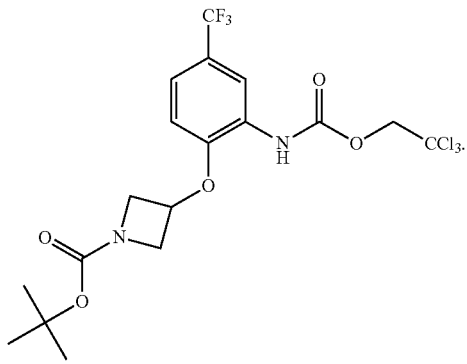

The title compound (0.15 g) was obtained using tert-butyl 3-(2-amino-4-(trifluoromethyl)phenoxy)azetidine-1-carboxylate (0.10 g, 0.30 mmol) by a method similar to that for the synthesis of 2,2,2-trichloroethyl (3-(hydroxymethyl)-2-methoxy-5-(trifluoromethyl)phenyl)carbamate (Reference Example 8).

MS(ESI) [M−tBu]$^+$: 451.

Reference Example 42

Synthesis of (S)-tert-butyl 3-(2-(((2,2,2-trichloroethyl)carbonyl)amino)-4-(trifluoromethyl)phenoxy)pyrrolidine-1-carboxylate

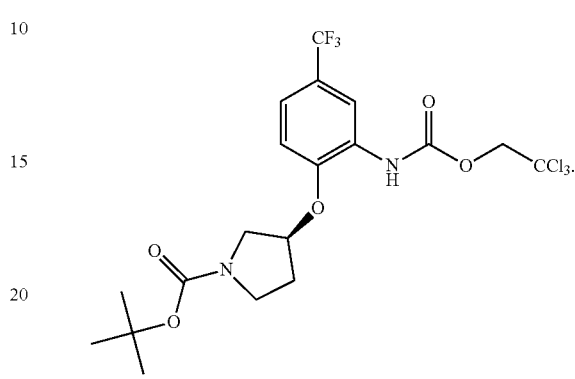

The title compound (0.49 g) was obtained using (S)-tert-butyl 3-(2-amino-4-(trifluoromethyl)phenoxy)pyrrolidine-1-carboxylate (0.34 g, 1.59 mmol) by a method similar to that for the synthesis of 2,2,2-trichloroethyl (3-(hydroxymethyl)-2-methoxy-5-(trifluoromethyl)phenyl)carbamate (Reference Example 8).

MS(ESI) [M−Boc]$^+$: 421.

Reference Example 43

Synthesis of (R)-tert-butyl 3-(2-(((2,2,2-trichloroethyl)carbonyl)amino)-4-(trifluoromethyl)phenoxy)pyrrolidine-1-carboxylate

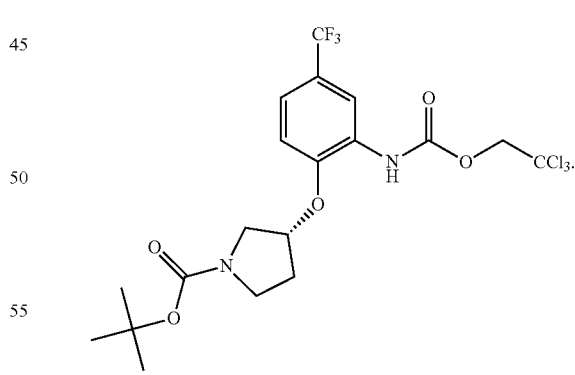

The title compound (0.51 g) was obtained using (R)-tert-butyl 3-(2-amino-4-(trifluoromethyl)phenoxy)pyrrolidine-1-carboxylate (0.50 g, 1.44 mmol) by a method similar to that for the synthesis of 2,2,2-trichloroethyl (3-(hydroxymethyl)-2-methoxy-5-(trifluoromethyl)phenyl)carbamate (Reference Example 8).

MS(ESI) [M−Boc]$^-$: 421.

Reference Example 44

Synthesis of 2,2,2-trichloroethyl (2-methyl-5-(trifluoromethyl)phenyl)carbamate

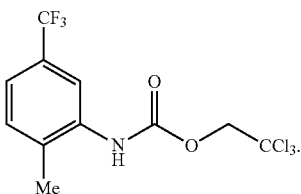

The title compound (0.18 g) was obtained using 2-methyl-5-(trifluoromethyl)aniline (0.20 g, 1.05 mmol) by a method similar to that for the synthesis of 2,2,2-trichloroethyl (3-(hydroxymethyl)-2-methoxy-5-(trifluoromethyl)phenyl)carbamate (Reference Example 8).
MS(ESI) [M+H]$^+$: 349.

Reference Example 45

Synthesis of 2,2,2-trichloroethyl (2-fluoro-5-(trifluoromethyl)phenyl)carbamate

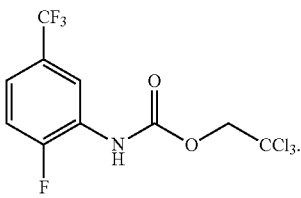

The title compound (0.15 g) was obtained using 2-fluoro-5-(trifluoromethyl)aniline (0.26 g, 1.23 mmol) by a method similar to that for the synthesis of 2,2,2-trichloroethyl (3-(hydroxymethyl)-2-methoxy-5-(trifluoromethyl)phenyl)carbamate (Reference Example 8).
MS(ESI) [M+H]$^+$: 354.

Reference Example 46

Synthesis of 2,2,2-trichloroethyl (2-chloro-5-(trifluoromethyl)phenyl)carbamate

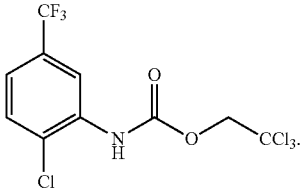

To a solution of 2-chloro-5-(trifluoromethyl)aniline (0.24 g, 1.1 mmol) and diazabicycloundecene (hereinafter referred to as DBU) (0.20 g, 1.3 mmol) in THF, 2,2,2-trichloroethyl chloroformate (0.20 g, 1.0 mmol) was added under cooling on ice. After stirring the obtained solution overnight at room temperature, water was added to the reaction solution, and the obtained solution was extracted with ethyl acetate. The organic layer was sequentially washed with a saturated aqueous solution of ammonium chloride and with a saturated aqueous solution of sodium chloride. The obtained organic layer was dried over anhydrous sodium sulfate and then concentrated under vacuum. The obtained crude product was purified by silica gel column chromatography (eluent; hexane:ethyl acetate=90:10→60:40) to obtain the title compound (0.12 g).
MS(ESI) [M+H]$^+$: 505.

Reference Example 47

Synthesis of 2,2,2-trichloroethyl (2-(oxetan-3-yloxy)-5-(trifluoromethoxy)phenyl)carbamate

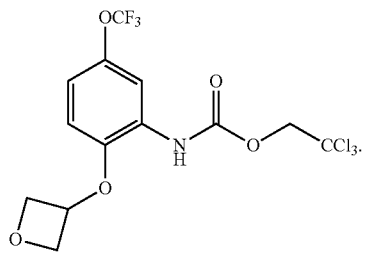

The title compound (0.12 g) was obtained using 1-chloro-2-nitro-4-(trifluoromethoxy)benzene (0.50 g, 1.79 mmol) by a method similar to that for 2,2,2-trichloroethyl (2-(oxetan-3-yloxy)-5-(trifluoromethyl)phenyl)carbamate (Reference Example 22).
MS(ESI) [M+H]$^+$: 424.

Reference Example 48

Synthesis of tert-butyl (trans-4-((2-morpholinopyrimidin-4-yl)oxy)cyclohexyl)carbamate

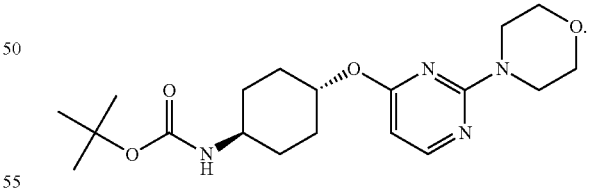

The title compound (0.54 g) was obtained using tert-butyl trans-(4-((2-chloropyrimidin-4-yl)oxy)cyclohexyl)carbamate (0.020 g, 0.061 mmol) by a method similar to that for the synthesis of 1-(2-methoxy-5-(trifluoromethoxy)phenyl)-3-(trans-4-((2-morpholinopyrimidin-4-yl)oxy)cyclohexyl)urea (Example 1).
$^1$H-NMR (400 MHz, CDCl$_3$) δ (ppm): 1.25-1.46 (13H, m), 2.10 (4H, m), 3.50 (1H, brs), 3.74-3.78 (8H, m), 4.41 (1H, brs), 4.92 (1H, brs), 5.96 (1H, d, J=5.6 Hz), 8.05 (1H, d, J=5.6 Hz).

Reference Example 49

Synthesis of tert-butyl (trans-4-(pyrimidin-2-yloxy)cyclohexyl)carbamate

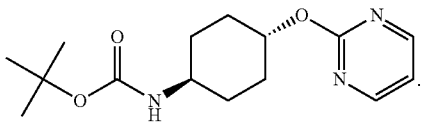 [SMILES: CC(C)(C)OC(=O)N[C@H]1CC[C@H](Oc2ncccn2)CC1]

The title compound (0.35 g) was obtained using 2-chloropyrimidine (0.30 g, 1.4 mmol) by a method similar to that for the synthesis of tert-butyl trans-(4-((2-chloropyrimidin-4-yl)oxy)cyclohexyl)carbamate (Reference Example 2).

$^1$H-NMR (400 MHz, CDCl$_3$) δ (ppm): 1.24-1.31 (2H, m), 1.42 (9H, s), 1.60-1.64 (2H, m), 2.07-2.15 (4H, m), 3.51 (1H, brs), 4.39 (1H, brs), 4.89-4.94 (1H, m), 6.86 (1H, t, J=4.8 Hz), 8.46 (2H, d, J=4.8 Hz).

Reference Example 50

Synthesis of tert-butyl (trans-4-(6-phenylpyridazin-3-yl)oxy)cyclohexyl)carbamate

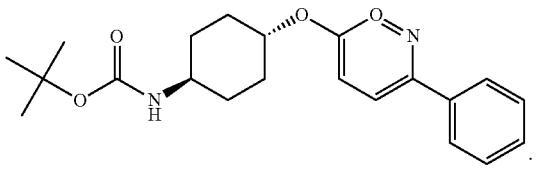

The title compound (0.060 g) was obtained using 3-chloro-6-phenylpyridazine (0.093 g, 0.49 mmol) by a method similar to that for the synthesis of tert-butyl trans-(4-((2-chloropyrimidin-4-yl)oxy)cyclohexyl)carbamate (Reference Example 2).

$^1$H-NMR (400 MHz, CDCl$_3$) δ (ppm): 1.33-1.36 (2H, m), 1.46 (9H, s), 1.61-1.64 (2H, m), 2.08-2.11 (2H, m), 2.29-2.31 (2H, m), 3.55 (1H, brs), 4.43 (1H, brs), 5.33 (1H, brs), 6.98 (1H, d, J=9.3 Hz), 7.48-7.50 (3H, m), 7.78 (1H, d, J=9.5 Hz), 8.00-8.02 (2H, m).

Reference Example 51

Synthesis of trans-4-((2-morpholinopyrimidin-4-yl)oxy)cyclohexanamine

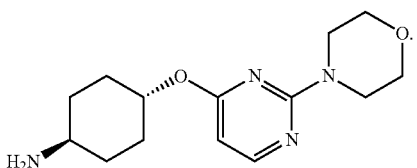

A solution of tert-butyl (trans-4-((2-morpholinopyrimidin-4-yl)oxy)cyclohexyl)carbamate (0.54 g, 1.4 mmol) in a 4 N hydrogen chloride/ethyl acetate solution (4 mL) was stirred at room temperature for two hours. The reaction solution was concentrated under vacuum, and a saturated aqueous solution of sodium hydrogen carbonate was added thereto, and the obtained solution was extracted with ethyl acetate and with a mixed solvent of chloroform/methanol. The organic layer was sequentially washed with a saturated aqueous solution of sodium hydrogen carbonate and with a saturated aqueous solution of sodium chloride. The obtained organic layer was dried over anhydrous sodium sulfate and then concentrated under vacuum to obtain the title compound (0.40 g).

$^1$H-NMR (400 MHz, CDCl$_3$) δ (ppm): 1.24-1.34 (2H, m), 1.48-1.55 (2H, m), 1.95-1.97 (2H, m), 2.12-2.15 (2H, m), 2.79-2.84 (1H, m), 3.75 (8H, s), 4.90-4.98 (1H, m), 5.95 (1H, d, J=5.6 Hz), 8.05 (1H, d, J=5.6 Hz).

Reference Example 52

Synthesis of trans-4-(pyrimidin-2-yloxy)cyclohexanamine

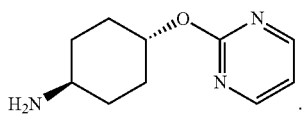

The title compound (0.020 g) was obtained using tert-butyl (trans-4-(pyrimidin-2-yloxy)cyclohexyl)carbamate (0.35 g, 1.2 mmol) by a method similar to that for the synthesis of trans-4-((2-morpholinopyrimidin-4-yl)oxy)cyclohexanamine (Reference Example 51).

$^1$H-NMR (400 MHz, CDCl$_3$) δ (ppm): 1.20-1.32 (2H, m), 1.55-1.60 (2H, m), 1.90-1.93 (2H, m), 2.14-2.16 (2H, m), 2.76-2.78 (1H, m), 4.92-4.94 (1H, m), 6.86 (1H, t, J=4.8 Hz), 8.46 (2H, d, J=4.9 Hz).

Reference Example 53

Synthesis of trans-4-(6-phenylpyridazin-3-yl)oxy)cyclohexanamine

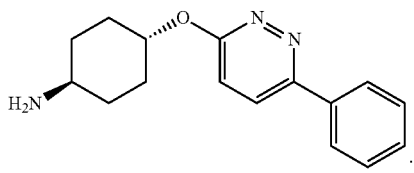 [SMILES: N[C@H]1CC[C@H](Oc2ccc(-c3ccccc3)nn2)CC1]

A crude product of the title compound (0.069 g) was obtained using tert-butyl (trans-4-(6-phenylpyridazin-3-yl)oxy)cyclohexyl)carbamate (0.060 g, 0.16 mmol) by a method similar to that for the synthesis of trans-4-((2-morpholinopyrimidin-4-yl)oxy)cyclohexanamine (Reference Example 51).

$^1$H-NMR (400 MHz, CDCl$_3$) δ (ppm): 1.32-1.35 (2H, m), 1.53-1.56 (2H, m), 1.94-1.97 (2H, m), 2.30-2.33 (2H, m), 2.80 (1H, brs), 5.33 (1H, brs), 6.98 (1H, d, J=9.0 Hz), 7.47-7.50 (3H, m), 7.78 (1H, d, J=9.0 Hz), 8.00-8.03 (2H, m).

Reference Example 54

Synthesis of tert-butyl (trans-4-(4-(methylamino) pyrimidin-2-yl)oxy)cyclohexyl)carbamate

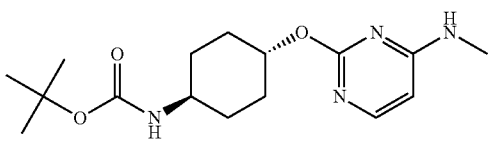

The title compound (0.048 g) was obtained using tert-butyl trans-(4-((4-chloropyrimidin-2-yl)oxy)cyclohexyl) carbamate (0.050 g, 0.15 mmol) by a method similar to that for the synthesis of 1-(2-methoxy-5-(trifluoromethoxy)phenyl)-3-(trans-4-((2-morpholinopyrimidin-4-yl)oxy)cyclohexyl)urea (Example 1).

$^1$H-NMR (400 MHz, CDCl$_3$) δ (ppm): 1.25-1.30 (2H, m), 1.43-1.46 (2H, m), 1.45 (9H, s), 2.06-2.15 (4H, m), 2.94 (3H, d, J=4.9 Hz), 3.50 (1H, brs), 4.39 (1H, brs), 4.85-4.91 (1H, m), 5.97 (1H, d, J=5.9 Hz), 7.96 (1H, d, J=5.9 Hz).

Reference Example 55

Synthesis of 2-((trans-4-aminocyclohexyl)oxy)-N-methylpyrimidin-4-amine dihydrochloride

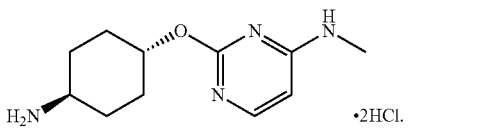 [SMILES: CNc1ccnc(O[C@H]2CC[C@H](N)CC2)n1]

A crude product of the title compound (0.056 g) was obtained using tert-butyl (trans-4-(4-(methylamino)-2-yl) oxy)cyclohexyl)carbamate (0.087 g, 0.27 mmol) by a method similar to that for the synthesis of trans-4-((2-chloropyrimidin-4-yl)oxy)cyclohexanamine hydrochloride (Reference Example 3).

Reference Example 56

Synthesis of trans-4-((4-morpholinopyrimidin-2-yl)oxy)cyclohexanamine

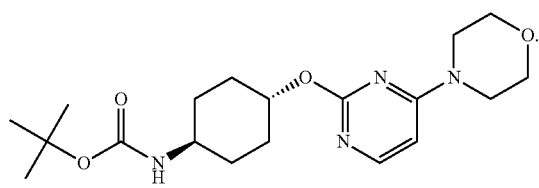 [SMILES: CC(C)(C)OC(=O)N[C@H]1CC[C@H](Oc2nccc(N3CCOCC3)n2)CC1]

The title compound (0.048 g) was obtained using tert-butyl trans-(4-((4-chloropyrimidin-2-yl)oxy)cyclohexyl) carbamate (0.020 g, 0.043 mmol) by a method similar to that for the synthesis of 1-(2-methoxy-5-(trifluoromethoxy)phenyl)-3-(trans-4-((2-morpholinopyrimidin-4-yl)oxy)cyclohexyl)urea (Example 1).

$^1$H-NMR (400 MHz, CDCl$_3$) δ (ppm): 1.25-1.28 (2H, m), 1.43-1.46 (11H, m), 2.05-2.17 (4H, m), 3.50 (1H, brs) 3.59-3.61 (4H, m), 3.75-3.76 (4H, m), 4.39 (1H, brs), 4.87 (1H, brs), 6.13 (1H, d, J=6.1 Hz), 8.02 (1H, d, J=6.1 Hz).

Reference Example 57

Synthesis of trans-4-((4-morpholinopyrimidin-2-yl) oxy)cyclohexanamine dihydrochloride

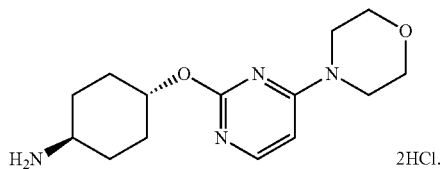 [SMILES: N[C@H]1CC[C@H](Oc2nccc(N3CCOCC3)n2)CC1]

A crude product of the title compound (0.056 g) was obtained using tert-butyl (trans-4-((4-morpholinopyrimidin-2-yl)oxy)cyclohexyl)carbamate (0.066 g, 0.15 mmol) by a method similar to that for the synthesis of trans-4-((2-chloropyrimidin-4-yl)oxy)cyclohexanamine hydrochloride (Reference Example 3).

Reference Example 58

Synthesis of tert-butyl trans-(4-((6-chloropyrimidin-4-yl)oxy)cyclohexyl)carbamate

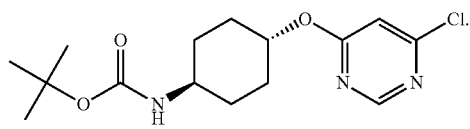

The title compound (0.56 g) was obtained using 4,6-dichloropyrimidine (0.35 g, 2.3 mmol) by a method similar to that for the synthesis of tert-butyl trans-(4-((2-chloropyrimidin-4-yl)oxy)cyclohexyl)carbamate (Reference Example 2).

$^1$H-NMR (400 MHz, CDCl$_3$) δ (ppm): 1.29-1.32 (2H, m), 1.44-1.46 (11H, m), 2.05-2.13 (4H, m), 3.50 (1H, s), 4.42 (1H, s), 5.06 (1H, s), 6.71 (1H, d, J=1.0 Hz), 8.53 (1H, d, J=0.7 Hz).

Reference Example 59

Synthesis of tert-butyl (trans-4-((6-morpholinopyrimidin-4-yl)oxy)cyclohexyl)carbamate

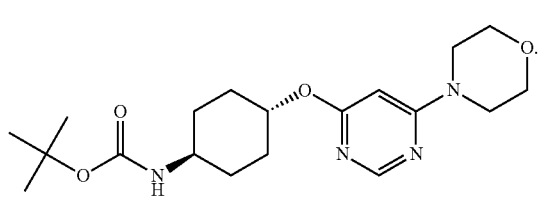 [SMILES: CC(C)(C)OC(=O)N[C@H]1CC[C@H](Oc2cc(N3CCOCC3)ncn2)CC1]

The title compound (0.058 g) was obtained using tert-butyl trans-(4-((6-chloropyrimidin-4-yl)oxy)cyclohexyl)

carbamate (0.050 g, 0.15 mmol) by a method similar to that for the synthesis of 1-(2-methoxy-5-(trifluoromethoxy)phenyl)-3-(trans-4-(2-morpholinopyrimidin-4-yl)oxy)cyclohexyl)urea (Example 1).

¹H-NMR (400 MHz, CDCl₃) δ (ppm): 1.17-1.35 (2H, m), 1.41-1.48 (11H, m), 2.07-2.10 (4H, m), 3.52-3.56 (4H, m), 3.74-3.58 (4H, m), 4.41 (1H, brs), 4.98 (1H, brs), 5.76 (1H, s), 8.29 (1H, s).

Reference Example 60

Synthesis of trans-4-((6-morpholinopyrimidin-4-yl)oxy)cyclohexanamine dihydrochloride

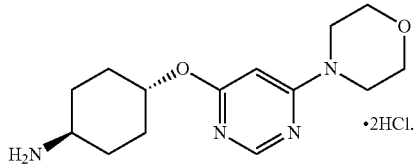

A crude product of the title compound (0.061 g) was obtained using tert-butyl (trans-4-((6-morpholinopyrimidin-4-yl)oxy)cyclohexyl)carbamate (0.059 g, 0.16 mmol) by a method similar to that for the synthesis of trans-4-((2-chloropyrimidin-4-yl)oxy)cyclohexanamine hydrochloride (Reference Example 3).

Reference Example 61

Synthesis of tert-butyl (trans-4-(6-(methylamino)pyrimidin-4-yl)oxy)cyclohexyl)carbamate

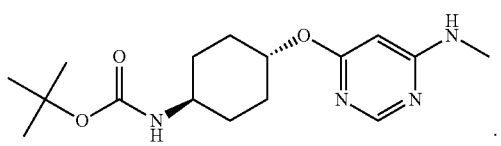 [SMILES: CNc1cc(O[C@H]2CC[C@H](NC(=O)OC(C)(C)C)CC2)ncn1]

The title compound (0.56 g) was obtained using tert-butyl trans-(4-((6-chloropyrimidin-4-yl)oxy)cyclohexyl)carbamate (0.050 g, 0.15 mmol) by a method similar to that for the synthesis of 1-(2-methoxy-5-(trifluoromethoxy)phenyl)-3-(trans-4-((2-morpholinopyrimidin-4-yl)oxy)cyclohexyl)urea (Example 1).

¹H-NMR (400 MHz, CDCl₃) δ (ppm): 1.30-1.32 (2H, m), 1.43-1.47 (11H, m), 2.07-2.11 (4H, m), 2.87 (3H, d, J=5.1 Hz), 3.50 (1H, brs), 4.42 (1H, brs), 4.83 (1H, brs), 4.99 (1H, brs), 5.60 (1H, d, J=0.7 Hz), 8.20 (1H, s).

Reference Example 62

Synthesis of 6-((trans-4-aminocyclohexyl)oxy)-N-methylpyrimidin-4-amine dihydrochloride

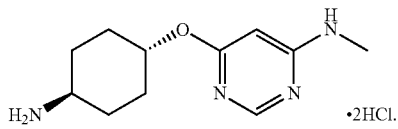

A crude product of the title compound (0.031 g) was obtained using tert-butyl (trans-4-(6-(methylamino)pyrimidin-4-yl)oxy)cyclohexyl)carbamate (0.029 g, 0.089 mmol) by a method similar to that for the synthesis of trans-4-((2-chloropyrimidin-4-yl)oxy)cyclohexanamine hydrochloride (Reference Example 3).

Reference Example 63

Synthesis of tert-butyl (trans-4-(2-(methylamino)pyrimidin-4-yl)oxy)cyclohexyl)carbamate

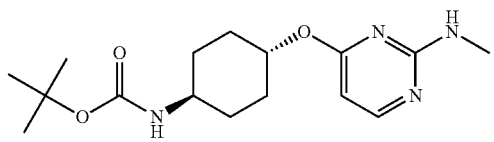

At room temperature, a solution of tert-butyl trans-(4-((2-chloropyrimidin-4-yl)oxy)cyclohexyl)carbamate (0.12 g, 0.37 mmol) in a methylamine/methanol solution (40% by weight, 0.37 mL) was stirred at room temperature for four hours. The reaction solution was concentrated under vacuum. The obtained crude product was purified by silica gel column chromatography (eluent; hexane:ethyl acetate=99:1→60:40) to obtain the title compound (0.087 g).

¹H-NMR (400 MHz, CDCl₃) δ (ppm): 1.25-1.29 (2H, m), 1.45 (9H, s), 1.51-1.55 (2H, m), 2.08-2.12 (4H, m), 2.96 (3H, d, J=5.1 Hz), 3.49 (1H, brs), 4.40 (1H, brs), 4.92 (1H, brs), 5.94 (1H, d, J=5.9 Hz), 8.00 (1H, d, J=5.6 Hz).

Reference Example 64

Synthesis of 4-((trans-4-aminocyclohexyl)oxy)-N-methylpyrimidin-2-amine dihydrochloride

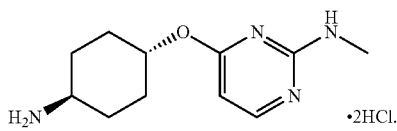 [SMILES: CNc1nccc(O[C@H]2CC[C@H](N)CC2)n1]

A crude product of the title compound (0.078 g) was obtained using tert-butyl (trans-4-(2-(methylamino)-4-yl)oxy)cyclohexyl)carbamate (0.087 g, 0.27 mmol) by a method similar to that for the synthesis of trans-4-((2-chloropyrimidin-4-yl)oxy)cyclohexanamine hydrochloride (Reference Example 3).

Reference Example 65

Synthesis of tert-butyl (trans-4-((2-((2-hydroxymethyl)amino)pyrimidin-4-yl)oxy)cyclohexyl)carbamate

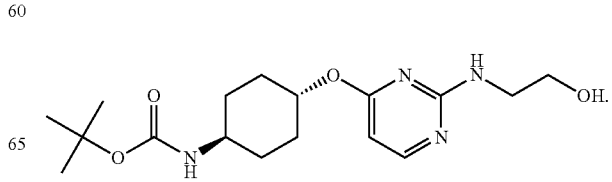

A crude product of the title compound (0.15 g) was obtained using 2-aminoethanol (55 mL, 0.92 mmol) and tert-butyl trans-(4-((2-chloropyrimidin-4-yl)oxy)cyclohexyl)carbamate (0.15 g, 0.46 mmol) by a method similar to that for the synthesis of 1-(2-methoxy-5-(trifluoromethoxy)phenyl)-3-(trans-4-((2-morpholinopyrimidin-4-yl)oxy)cyclohexyl)urea (Example 1).

Reference Example 66

Synthesis of tert-butyl (trans-4-((2-((2-hydroxymethyl)amino)pyrimidin-4-yl)oxy)cyclohexyl)carbamate dihydrochloride

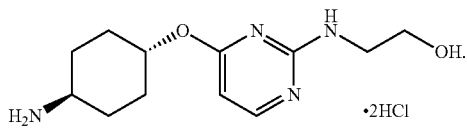 [SMILES: N[C@H]1CC[C@H](Oc2ccnc(NCCO)n2)CC1]

A crude product of the title compound (0.11 g) was obtained using tert-butyl (trans-4-((2-((2-hydroxymethyl)amino)pyrimidin-4-yl)oxy)cyclohexyl)carbamate (0.15 g, 0.43 mmol) by a method similar to that for the synthesis of trans-4-((2-chloropyrimidin-4-yl)oxy)cyclohexanamine hydrochloride (Reference Example 3).

Reference Example 67

Synthesis of tert-butyl (trans-4-(pyridin-4-ylmethoxy)cyclohexyl)carbamate

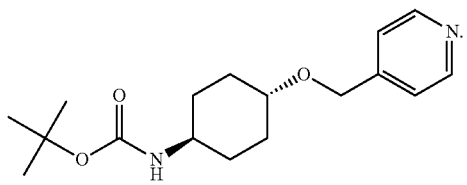 [SMILES: CC(C)(C)OC(=O)N[C@H]1CC[C@H](OCc2ccncc2)CC1]

To a solution of tert-butyl trans-(4-hydroxycyclohexyl)carbamate (0.20 g, 0.93 mmol) and 4-(bromomethyl)pyridine hydrobromide (0.18 g, 0.72 mmol) in DMF, sodium hydride (55% by weight in mineral oil, 0.096 g) was added. After stirring the obtained solution at room temperature for one and a half hours, water was added to the reaction solution, and the obtained solution was extracted with ethyl acetate and sequentially washed with a saturated aqueous solution of ammonium chloride and with a saturated aqueous solution of sodium chloride. The organic layer was dried over anhydrous sodium sulfate and then concentrated under vacuum. The obtained crude product was purified by silica gel column chromatography (eluent; hexane:ethyl acetate=95:5→35:65) to obtain the title compound (0.053 g).

MS(ESI) [M+H]$^+$: 307.

Reference Example 68

Synthesis of trans-4-(pyridin-4-ylmethoxy)cyclohexanamine dihydrochloride

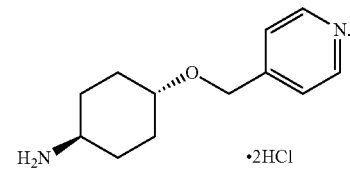 [SMILES: N[C@H]1CC[C@H](OCc2ccncc2)CC1]

The title compound (0.012 g) was obtained using tert-butyl (trans-4-(pyridin-4-ylmethoxy)cyclohexyl)carbamate (0.017 g, 0.055 mmol) by a method similar to that for the synthesis of trans-4-((2-chloropyrimidin-4-yl)oxy)cyclohexanamine hydrochloride (Reference Example 3).

MS(ESI) [M+H]$^+$: 207.

Reference Example 69

Synthesis of tert-butyl (trans-4-(pyridin-3-ylmethoxy)cyclohexyl)carbamate

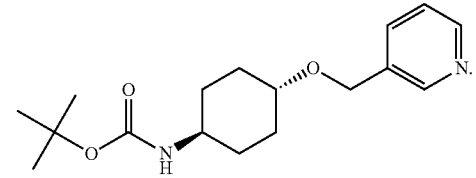 [SMILES: CC(C)(C)OC(=O)N[C@H]1CC[C@H](OCc2cccnc2)CC1]

The title compound (0.094 g) was obtained using 3-(bromomethyl)pyridine hydrobromide (0.53 g, 2.1 mmol) by a method similar to that for the synthesis of tert-butyl (trans-4-(pyridin-4-ylmethoxy)cyclohexyl)carbamate (Reference Example 67).

$^1$H-NMR (400 MHz, CDCl$_3$) δ (ppm): 1.13-1.16 (2H, m), 1.42-1.46 (11H, s), 2.05-2.06 (4H, m), 3.33 (1H, brs), 3.45 (1H, brs), 4.37 (1H, brs), 4.55 (2H, s), 7.25-7.28 (1H, m), 7.68 (1H, d, J=8.0 Hz), 8.54-8.56 (2H, m).

Reference Example 70

Synthesis of trans-4-(pyridin-3-ylmethoxy)cyclohexanamine dihydrochloride

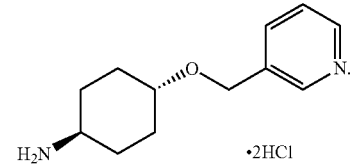

A crude product of the title compound (0.078 g) was obtained using tert-butyl (trans-4-(pyridin-3-ylmethoxy)cyclohexyl)carbamate (0.029 g, 0.089 mmol) by a method similar to that for the synthesis of trans-4-((2-chloropyrimidin-4-yl)oxy)cyclohexanamine hydrochloride (Reference Example 3).

Reference Example 71

Synthesis of tert-butyl (trans-4-((pyridin-3-yl-methoxy)methyl)cyclohexyl)carbamate

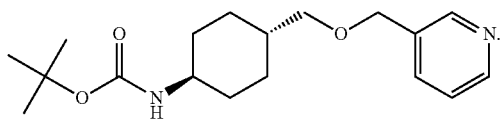 [SMILES: CC(C)(C)OC(=O)N[C@H]1CC[C@H](COCc2cccnc2)CC1]

The title compound (0.12 g) was obtained using tert-butyl (trans-4-(hydroxylmethyl)cyclohexyl)carbamate (0.20 g, 0.87 mmol) and 3-(bromomethyl)pyridine hydrobromide (0.20 g, 0.79 mmol) by a method similar to that for the synthesis of tert-butyl (trans-4-(pyridin-4-ylmethoxy)cyclohexyl)carbamate (Reference Example 67).

$^1$H-NMR (400 MHz, CDCl$_3$) δ (ppm): 1.03-1.11 (4H, m), 1.44 (9H, s), 1.53-1.57 (1H, m), 1.83-1.86 (2H, m), 2.02-2.04 (2H, m), 3.29-3.30 (2H, m), 3.38-3.41 (1H, m), 4.37 (1H, brs), 4.50 (2H, brs), 7.28-7.29 (1H, m), 7.66 (1H, d, J=8.0 Hz), 8.53-8.55 (2H, m).

Reference Example 72

Synthesis of trans-4-((pyridin-3-ylmethoxy)methyl)cyclohexanamine dihydrochloride

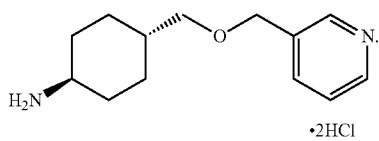 [SMILES: N[C@H]1CC[C@H](COCc2cccnc2)CC1]

A crude product of the title compound (0.084 g) was obtained using tert-butyl (trans-4-((pyridin-3-ylmethoxy)methyl)cyclohexyl)carbamate (0.12 g, 0.38 mmol) by a method similar to that for the synthesis of trans-4-((2-chloropyrimidin-4-yl)oxy)cyclohexanamine hydrochloride (Reference Example 3).

Reference Example 73

Synthesis of tert-butyl (trans-4-((pyridin-4-yl-methoxy)methyl)cyclohexyl)carbamate

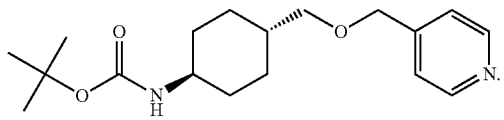 [SMILES: CC(C)(C)OC(=O)N[C@H]1CC[C@H](COCc2ccncc2)CC1]

The title compound (0.14 g) was obtained using tert-butyl (trans-4-(hydroxymethyl)cyclohexyl)carbamate (0.20 g, 0.87 mmol) and 4-(bromomethyl)pyridine hydrobromide (0.20 g, 0.79 mmol) by a method similar to that for the synthesis of tert-butyl (trans-4-(pyridin-4-ylmethoxy)cyclohexyl)carbamate (Reference Example 67).

$^1$H-NMR (400 MHz, CDCl$_3$) δ (ppm): 1.07-1.16 (4H, m), 1.44 (9H, s), 1.53-1.57 (1H, m), 1.85-1.87 (2H, m), 2.03-2.05 (2H, m), 3.31 (2H, d, J=6.6 Hz), 3.39 (1H, brs), 4.38 (1H, brs), 4.50 (2H, s), 7.24 (2H, dd, J=3.4, 2.7 Hz), 8.56 (2H, dd, J=4.4, 1.5 Hz).

Reference Example 74

Synthesis of trans-4-((pyridin-4-ylmethoxy)methyl)cyclohexanamine dihydrochloride

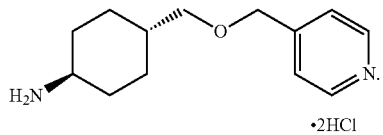 [SMILES: N[C@H]1CC[C@H](COCc2ccncc2)CC1]

A crude product of the title compound (0.097 g) was obtained using tert-butyl (trans-4-((pyridin-4-ylmethoxy)methyl)cyclohexyl)carbamate (0.14 g, 0.44 mmol) by a method similar to that for the synthesis of trans-4-((2-chloropyrimidin-4-yl)oxy)cyclohexanamine hydrochloride (Reference Example 3).

Reference Example 75

Synthesis of methyl 5-((trans-4-((tert-butoxycarbonyl)amino)cyclohexyl)methoxy)nicotinate

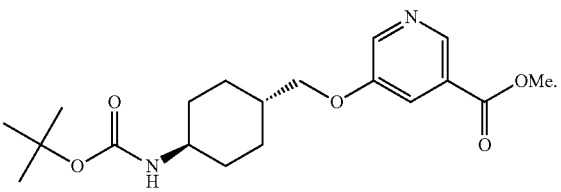 [SMILES: COC(=O)c1cncc(OC[C@H]2CC[C@H](NC(=O)OC(C)(C)C)CC2)c1]

To a solution of tert-butyl (trans-4-(hydroxymethyl)cyclohexyl)carbamate (0.10 g, 0.44 mmol), methyl 5-hydroxynicotinate (0.10 g, 0.65 mmol) and triphenylphosphine (0.17 g, 0.65 mmol) in THF (5 mL), bis(2-methoxyethyl) azodicarboxylate (0.15 g, 0.65 mmol) was added under cooling on ice. After stirring the obtained solution overnight at room temperature, water was added to the reaction solution, and the obtained solution was extracted with ethyl acetate. The organic layer was dried over anhydrous sodium sulfate and then concentrated under vacuum. The obtained crude product was purified by silica gel column chromatography (eluent; hexane:ethyl acetate=80:20→55:45) to obtain the title compound (0.12 g).

$^1$H-NMR (400 MHz, CDCl$_3$) δ (ppm): 1.13-1.24 (4H, m), 1.45 (9H, s), 1.76-1.80 (1H, m), 1.94-1.96 (2H, m), 2.06-2.09 (2H, m), 3.42 (1H, brs), 3.84 (2H, d, J=6.3 Hz), 3.95 (3H, s), 4.41 (1H, brs), 7.73-7.73 (1H, m), 8.45 (1H, d, J=2.9 Hz), 8.81 (1H, d, J=1.5 Hz).

Reference Example 76

Synthesis of 5-((trans-4-((tert-butoxycarbonyl)amino)cyclohexyl)methoxy)nicotinic acid

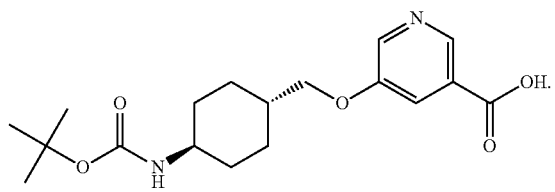 [SMILES: CC(C)(C)OC(=O)N[C@H]1CC[C@H](COc2cncc(C(=O)O)c2)CC1]

To a solution of methyl 5-((trans-4-((tert-butoxycarbonyl)amino)cyclohexyl)methoxy)nicotinate (0.092 g, 0.25 mmol) in a mixed solvent of THF/methanol (THF:methanol=1:1, v/v, 2 mL), a 1 N aqueous solution of sodium hydroxide (0.50 mL) was added. After stirring the obtained solution overnight at room temperature, a saturated aqueous solution of ammonium chloride was added to the reaction solution, and the obtained solution was extracted with ethyl acetate. The organic layer was dried over anhydrous sodium sulfate and then concentrated under vacuum, and a crude product of the title compound (0.086 g) was obtained.

Reference Example 77

Synthesis of tert-butyl (trans-4-(((5-carbamoylpyridin-3-yl)oxy)methyl)cyclohexyl)carbamate

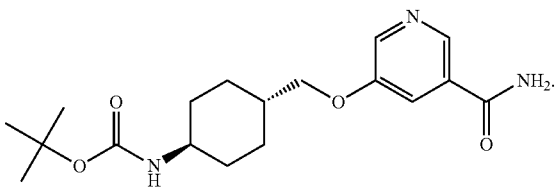 [SMILES: CC(C)(C)OC(=O)N[C@H]1CC[C@H](COc2cncc(C(N)=O)c2)CC1]

To a solution of 5-((trans-4-((tert-butoxycarbonyl)amino)cyclohexyl)methoxy)nicotinic acid (0.086 g, 0.25 mmol), ammonium chloride (0.13 g, 2.5 mmol), 2-(7-aza-1H-benzotriazol-1-yl)-1,1,3,3-tetramethyluronium hexafluorophosphate and O-(benzotriazol-1-yl)-N,N,N',N'-tetramethyluronium hexafluorophosphate (hereinafter referred to as HATU) (0.14 g, 0.37 mmol) in DMF (2 mL), DIPEA (0.48 mL, 3.7 mmol) was added under cooling on ice. After stirring the obtained solution overnight at room temperature, water and 1 N hydrochloric acid were added to the reaction solution, the obtained solution was extracted with ethyl acetate. The organic layer was dried over anhydrous sodium sulfate and then concentrated under vacuum. The obtained crude product was purified by silica gel column chromatography (eluent; chloroform:methanol=99:1→95:5) to obtain the title compound (0.019 g).

$^1$H-NMR (400 MHz, CDCl$_3$) δ (ppm): 1.14-1.19 (4H, m), 1.45 (9H, s), 1.76-1.80 (1H, m), 1.93-1.96 (2H, m), 2.08-2.11 (2H, m), 3.42 (1H, brs), 3.86 (2H, d, J=6.3 Hz), 4.41 (1H, brs), 7.66 (1H, s), 8.43 (1H, d, J=2.9 Hz), 8.53 (1H, d, J=1.7 Hz).

Reference Example 78

Synthesis of 5-((trans-4-aminocyclohexyl)methoxy)nicotinamide dihydrochloride

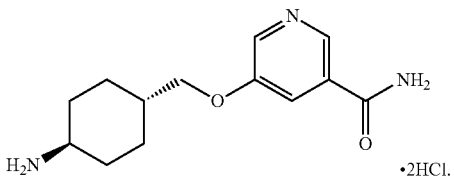 [SMILES: NC(=O)c1cncc(OC[C@H]2CC[C@H](N)CC2)c1]

A crude product of the title compound (0.014 g) was obtained using tert-butyl (trans-4-(((5-carbamoylpyridin-3-yl)oxy)methyl)cyclohexyl)carbamate (0.019 g, 0.054 mmol) by a method similar to that for the synthesis of trans-4-((2-chloropyrimidin-4-yl)oxy)cyclohexanamine hydrochloride (Reference Example 3).

Reference Example 79

Synthesis of methyl 3-((trans-4-((tert-butoxycarbonyl)amino)cyclohexyl)methoxy)benzoate

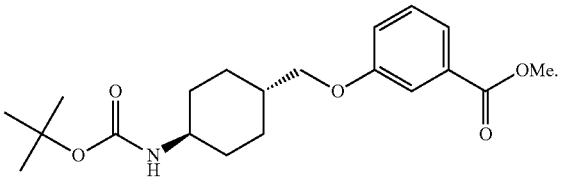 [SMILES: COC(=O)c1cccc(OC[C@H]2CC[C@H](NC(=O)OC(C)(C)C)CC2)c1]

The title compound (0.092 g) was obtained using methyl 3-hydroxybenzoate (0.10 g, 0.65 mmol) by a method similar to that for the synthesis of methyl 5-((trans-4-((tertbutoxycarbonyl)amino)cyclohexyl)methoxy)nicotinate (Reference Example 75).

$^1$H-NMR (400 MHz, CDCl$_3$) δ (ppm): 1.12-1.20 (4H, m), 1.45 (9H, s), 1.76 (1H, brs), 1.94-1.96 (2H, m), 2.06-2.08 (2H, m), 3.42 (1H, brs), 3.80 (2H, d, J=6.3 Hz), 3.91 (3H, s), 4.40 (1H, brs), 7.07 (1H, dt, J=8.3, 1.2 Hz), 7.33 (1H, t, J=7.9 Hz), 7.52 (1H, t, J=2.0 Hz), 7.61 (1H, dt, J=7.6, 1.2 Hz).

Reference Example 80

Synthesis of 3-((trans-4-((tert-butoxycarbonyl)amino)cyclohexyl)methoxy)benzoic acid

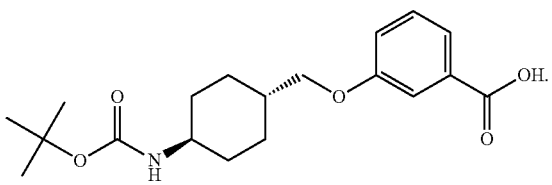 [SMILES: CC(C)(C)OC(=O)N[C@H]1CC[C@H](COc2cccc(C(=O)O)c2)CC1]

The title compound (0.081 g) was obtained using methyl 3-((trans-4-((tert-butoxycarbonyl)amino)cyclohexyl)methoxy)benzoate (0.092 g, 0.25 mmol) by a method similar to that for the synthesis of 5-((trans-4-((tert-butoxycarbonyl)amino)cyclohexyl)methoxy)nicotinic acid (Reference Example 76).

Reference Example 81

Synthesis of tert-butyl (trans-4-((3-carbamoylphenoxy)methyl)cyclohexyl)carbamate

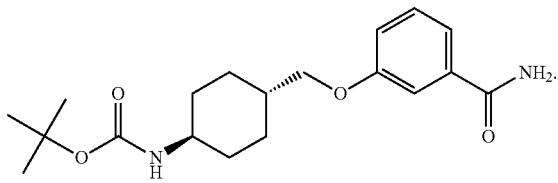 [SMILES: CC(C)(C)OC(=O)N[C@H]1CC[C@H](COc2cccc(C(N)=O)c2)CC1]

The title compound (0.081 g) was obtained using 3-((trans-4-((tertbutoxycarbonyl)amino)cyclohexyl)methoxy)benzoic acid (0.081 g, 0.23 mmol) by a method similar to that for the synthesis of tert-butyl (trans-4-(((5-carbamoylpyridin-3-yl)oxy)methyl)cyclohexyl)carbamate (Reference Example 77).
$^1$H-NMR (400 MHz, CDCl$_3$) δ (ppm): 1.12-1.22 (4H, m), 1.76 (1H, s), 1.94 (2H, d, J=8.5 Hz), 2.08 (2H, s), 3.42 (1H, s), 3.81 (2H, d, J=6.3 Hz), 4.41 (1H, s), 5.58 (1H, s), 6.02 (1H, s), 7.03-7.06 (1H, m), 7.31-7.34 (3H, m).

Reference Example 82

Synthesis of 3-((trans-4-aminocyclohexyl)methoxy)benzamide hydrochloride

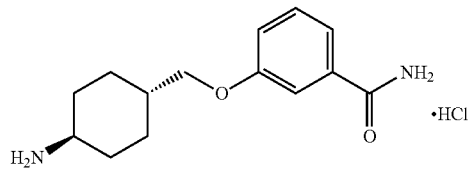

A crude product of the title compound (0.045 g) was obtained using 3-((trans-4-((tert-butoxycarbonyl)amino)cyclohexyl)methoxy)benzoic acid (0.081 g, 0.23 mmol) by a method similar to that for the synthesis of trans-4-((2-chloropyrimidin-4-yl)oxy)cyclohexanamine hydrochloride (Reference Example 3).

Reference Example 83

Synthesis of tert-butyl (trans-4-((2-chloropyridin-4-yl)oxy)cyclohexyl)carbamate

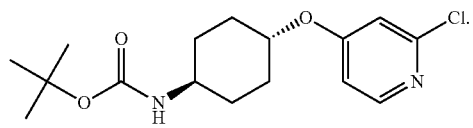 [SMILES: CC(C)(C)OC(=O)N[C@H]1CC[C@H](Oc2ccnc(Cl)c2)CC1]

The title compound (0.082 g) was obtained using 2-chloro-4-nitropyridine (0.10 g, 0.46 mmol) by a method similar to that for the synthesis of tert-butyl (trans-4-(pyridin-4-ylmethoxy)cyclohexyl)carbamate (Reference Example 67).
MS(ESI) [M+H]$^+$: 327.

Reference Example 84

Synthesis of tert-butyl (trans-4-((2-chloropyridin-4-yl)oxy)cyclohexyl)carbamate

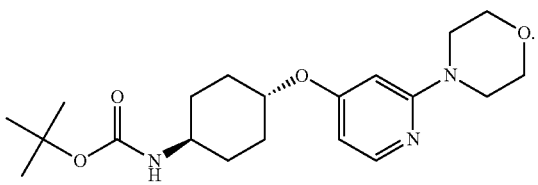

A solution of tert-butyl (trans-4-((2-chloropyridin-4-yl)oxy)cyclohexyl)carbamate (0.10 g, 0.31 mmol) in morpholine (5 mL) was stirred for 30 minutes at 170° C. by using the microwave synthesis reactor, and water was subsequently added to the reaction solution, and the obtained solution was extracted with ethyl acetate and sequentially washed with 0.01 N hydrochloric acid and with a saturated aqueous solution of sodium chloride. The organic layer was dried over anhydrous sodium sulfate and then concentrated under vacuum. The obtained crude product was purified by silica gel column chromatography (eluent; hexane:ethyl acetate=80:20→50:50) to obtain the title compound (0.025 g).
MS(ESI) [M+H]$^+$: 378.

Reference Example 85

Synthesis of trans-4-((2-morpholinopyridin-4-yl)oxy)cyclohexanamine dihydrochloride

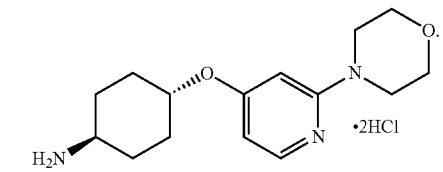 [SMILES: N[C@H]1CC[C@H](Oc2ccnc(N3CCOCC3)c2)CC1 ; "·2HCl"]

The title compound (0.010 g) was obtained using tert-butyl (trans-4-((2-chloropyridin-4-yl)oxy)cyclohexyl)carbamate (0.025 g, 0.066 mmol) by a method similar to that for the synthesis of trans-4-((2-chloropyrimidin-4-yl)oxy)cyclohexanamine hydrochloride (Reference Example 3).
MS(ESI) [M+H]$^+$: 278.

Reference Example 86

Synthesis of tert-butyl (trans-4-(pyridin-4-yloxy)cyclohexyl)carbamate hydrochloride

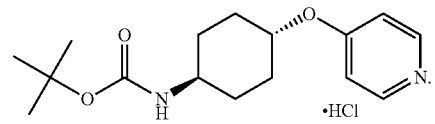 [SMILES: CC(C)(C)OC(=O)N[C@H]1CC[C@H](Oc2ccncc2)CC1 ; Cl]

The title compound (0.042 g) was obtained using tert-butyl (trans-4-((2-chloropyridin-4-yl)oxy)cyclohexyl)carbamate (0.050 g, 0.15 mmol) by a method similar to that for the synthesis of 4-(2-amino-4-(trifluoromethyl)phenyl)piperazin-2-one (Reference Example 20).

MS(ESI) [M+H]⁺: 293.

Reference Example 87

Synthesis of trans-4-(pyridin-4-yloxy)cyclohexanamine dihydrochloride

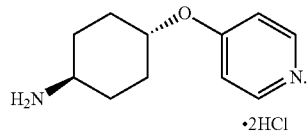 [SMILES: N[C@H]1CC[C@H](Oc2ccncc2)CC1 ; "·2HCl"]

A crude product of the title compound (0.025 g) was obtained using tert-butyl (trans-4-(pyridin-4-yloxy)cyclohexyl)carbamate (0.040 g, 0.14 mmol) by a method similar to that for the synthesis of trans-4-((2-chloropyrimidin-4-yl)oxy)cyclohexanamine hydrochloride (Reference Example 3).

MS(ESI) [M+H]⁺: 193.

Reference Example 88

Synthesis of tert-butyl (trans-4-((2-(pyridin-3-yl)pyrimidin-4-yl)oxy)cyclohexyl)carbamate

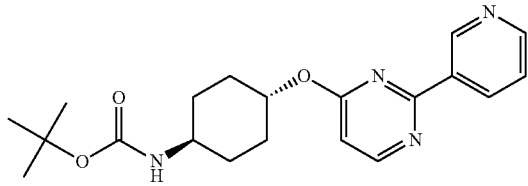

A solution of tert-butyl trans-(4-((2-chloropyrimidin-4-yl)oxy)cyclohexyl)carbamate (0.063 g, 0.19 mmol), pyridine-3-boronic acid (0.028 g, 0.23 mmol), PdCl₂(PPh₃)₂ (0.0067 g, 0.0096 mmol) and potassium carbonate (0.056 g, 0.40 mmol) in a mixed solvent of 1,4-dioxane/water (1,4-dioxane:water=2:1, v/v) was stirred at 105° C. for eight hours under nitrogen atmosphere, and water was subsequently added to the reaction solution, and the obtained solution was extracted with ethyl acetate. The organic layer was sequentially washed with a saturated aqueous solution of ammonium chloride and with a saturated aqueous solution of sodium chloride. The obtained organic layer was dried over anhydrous sodium sulfate and then concentrated under vacuum, and the obtained crude product was purified by silica gel column chromatography (eluent; hexane:ethyl acetate=90:10→60:40) to obtain the title compound (0.047 g).

MS(ESI) [M+H]⁺: 371.

Reference Example 89

Synthesis of tert-butyl (trans-4-((4-(pyridin-3-yl)pyrimidin-2-yl)oxy)cyclohexyl)carbamate

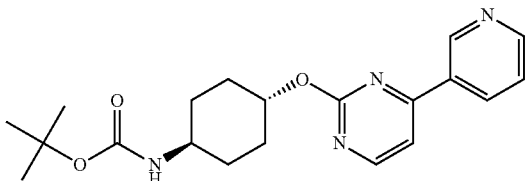

The title compound (0.05 g) was obtained using tert-butyl trans-(4-((4-chloropyrimidin-2-yl)oxy)cyclohexyl)carbamate (0.07 g, 0.21 mmol) by a method similar to that for the synthesis of tert-butyl (trans-4-((2-(pyridin-3-yl)pyrimidin-4-yl)oxy)cyclohexyl)carbamate (Reference Example 88).

MS(ESI) [M+H]⁺: 371.

Reference Example 90

Synthesis of trans-4-((2-(pyridin-3-yl)pyrimidin-4-yl)oxy)cyclohexanamine dihydrochloride

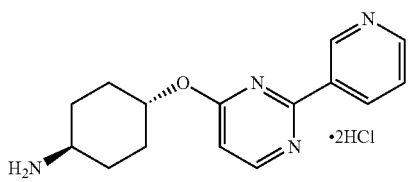

The title compound (0.03 g) was obtained using tert-butyl (trans-4-((2-(pyridin-3-yl)pyrimidin-4-yl)oxy)cyclohexyl)carbamate (0.05 g, 0.14 mmol) by a method similar to that for the synthesis of trans-4-((2-chloropyrimidin-4-yl)oxy)cyclohexanamine hydrochloride (Reference Example 3).

Reference Example 91

Synthesis of trans-4-((4-(pyridin-3-yl)pyrimidin-2-yl)oxy)cyclohexanamine dihydrochloride

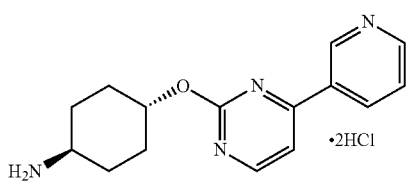

The title compound (0.03 g) was obtained using tert-butyl (trans-4-((4-(pyridin-3-yl)pyrimidin-2-yl)oxy)cyclohexyl)carbamate (0.047 g, 0.13 mmol) by a method similar to that for the synthesis of trans-4-((2-chloropyrimidin-4-yl)oxy)cyclohexanamine hydrochloride (Reference Example 3).

Reference Example 92

Synthesis of tert-butyl (trans-4-((2-(pyridin-4-yl)pyrimidin-4-yl)oxy)cyclohexyl)carbamate

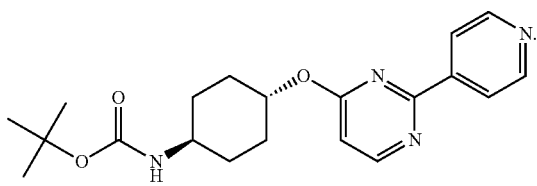 [SMILES: CC(C)(C)OC(=O)N[C@H]1CC[C@H](Oc2ccnc(-c3ccncc3)n2)CC1]

The title compound (0.10 g) was obtained using tert-butyl trans-(4-((4-chloropyrimidin-2-yl)oxy)cyclohexyl)carbamate (0.2 g, 0.61 mmol) and pyridine-4-boronic acid (0.09 g, 0.73 mmol) by a method similar to that for the synthesis of tert-butyl (trans-4-((2-(pyridin-3-yl)pyrimidin-4-yl)oxy)cyclohexyl)carbamate (Reference Example 88).
MS(ESI) [M+H]$^+$: 371.

Reference Example 93

Synthesis of trans-4-((2-(pyridin-4-yl)pyrimidin-4-yl)oxy)cyclohexanamine dihydrochloride

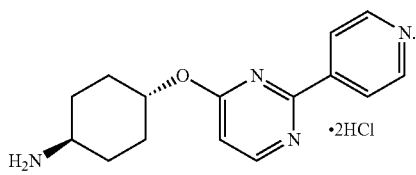 [SMILES: N[C@H]1CC[C@H](Oc2ccnc(-c3ccncc3)n2)CC1 ; "·2HCl"]

The title compound (0.059 g) was obtained using tert-butyl (trans-4-((2-(pyridin-3-yl)pyrimidin-4-yl)oxy)cyclohexyl)carbamate (0.2 g, 0.28 mmol) by a method similar to that for the synthesis of trans-4-((2-chloropyrimidin-4-yl)oxy)cyclohexanamine hydrochloride (Reference Example 3).

Reference Example 94

Synthesis of 2-morpholino-5-(trifluoromethyl)aniline

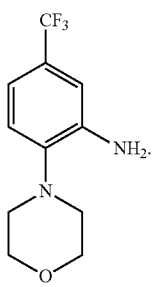

Morpholine (5.0 ml) was added to 1-chloro-2-nitro-4-(trifluoromethyl)benzene (0.4 g, 1.77 mmol), and the obtained solution was heated at 100° C. for five hours. A solution of 0.01 N hydrochloric acid was added to the reaction solution, and the obtained solution was then extracted with ethyl acetate and washed with a saturated aqueous solution of sodium chloride. The organic layer was dried over anhydrous sodium sulfate and then concentrated under vacuum, and the obtained crude product was used in a similar way to the synthesis of 4-(2-amino-4-(trifluoromethyl)phenyl)piperazin-2-one (Reference Example 20) to obtain the title compound. The obtained compound was used without purification in the next reaction.
MS(ESI) [M+H]$^+$: 247.

Reference Example 95

Synthesis of 2,2,2-trichloroethyl (2-morpholino-5-(trifluoromethyl)phenyl)carbamate

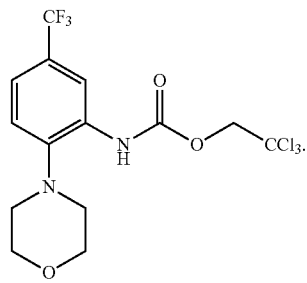

The title compound (0.18 g) was obtained using 2-morpholino-5-(trifluoromethyl)aniline (0.19 g, 0.89 mol) by a method similar to that for the synthesis of 2,2,2-trichloroethyl (3-(hydroxymethyl)-2-methoxy-5-(trifluoromethyl)phenyl)carbamate (Reference Example 8).
MS(ESI) [M+H]$^+$: 421.

Reference Example 96

Synthesis of methyl 3-amino-5-(trifluoromethyl)benzoate

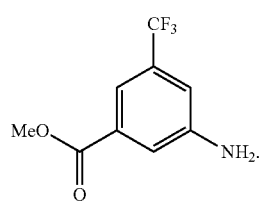 [SMILES: COC(=O)c1cc(N)cc(C(F)(F)F)c1]

To a solution of 3-nitro-5-(trifluoromethyl)benzoic acid (1.0 g, 4.25 mmol) in methanol, a catalyst amount of p-toluenesulfonic acid was added, and the obtained solution was heated under reflux for 15 hours. The obtained reaction liquid was returned to room temperature and then concentrated to the half of the original volume. Palladium (10% by weight) on carbon (containing 50% water by weight, 0.062 g) was added to the reaction liquid, and the obtained solution was stirred for one hour under hydrogen atmosphere. The reaction liquid was filtered through Celite®, the filtrate was concentrated under vacuum, and the obtained crude product was purified by silica gel column chromatography (eluent; hexane:ethyl acetate=90:10→60:40) to obtain the title compound (0.85 g).
MS(ESI) [M+H]$^+$: 221.

Reference Example 97

Synthesis of (3-amino-5-(trifluoromethyl)phenyl)methanol

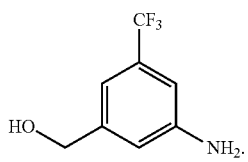

To a solution of methyl 3-amino-5-(trifluoromethyl)benzoate (0.4 g, 1.825 mmol) in THF, lithium aluminium hydride (0.215 g, 5.66 mmol) was slowly added under cooling on ice. The ice bath was removed, and the obtained solution was stirred overnight. Water was slowly added to the reaction solution, and the obtained solution was extracted with ethyl acetate. The organic layer was sequentially washed with a saturated aqueous solution of ammonium chloride and with a saturated aqueous solution of sodium chloride. The obtained organic layer was dried over anhydrous sodium sulfate and then concentrated under vacuum, and the obtained crude product was purified by silica gel column chromatography (eluent; hexane:ethyl acetate=90:10→60:40) to obtain the title compound (0.32 g).
MS(ESI) [M+H]⁺: 371.

Reference Example 98

Synthesis of 2,2,2-trichloroethyl (3-(hydroxymethyl)-5-(trifluoromethyl)phenyl)carbamate

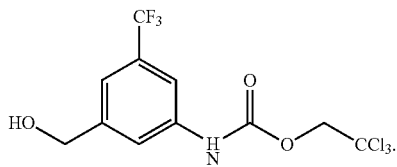

The title compound (0.13 g) was obtained using (3-amino-5-(trifluoromethyl)phenyl)methanol (0.318 g, 1.5 mmol) by a method similar to that for the synthesis of 2,2,2-trichloroethyl (3-(hydroxymethyl)-2-methoxy-5-(trifluoromethyl)phenyl)carbamate (Reference Example 8).
MS(ESI) [M+H]⁺: 367.

Reference Example 99

Synthesis of methyl 4-amino-6-(trifluoromethyl)benzoate

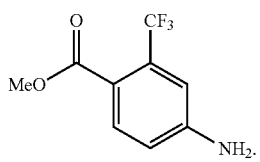

The title compound (0.9 g) was obtained using 4-nitro-6-(trifluoromethyl)benzoic acid (1.0 g, 4.25 mmol) by a method similar to that for the synthesis of methyl 3-amino-5-(trifluoromethyl)benzoate (Reference Example 96).
MS(ESI) [M+H]⁺: 221.

Reference Example 100

Synthesis of (4-amino-6-(trifluoromethyl)phenyl)methanol

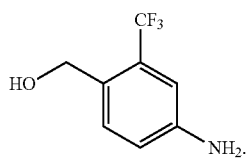

The title compound (0.31 g) was obtained using methyl 4-amino-6-(trifluoromethyl)benzoate (0.4 g, 1.825 mmol) by a method similar to that for the synthesis of (3-amino-5-(trifluoromethyl)phenyl)methanol (Reference Example 97).
MS(ESI) [M+H]⁺: 371.

Reference Example 101

2,2,2-trichloroethyl (4-(hydroxymethyl)-5-(trifluoromethyl)phenyl)carbamate

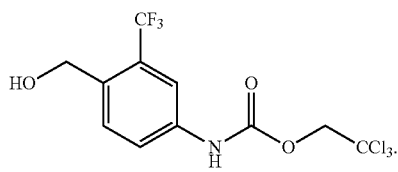

The title compound (0.16 g) was obtained using (4-amino-6-(trifluoromethyl)phenyl)methanol (0.13 g, 0.61 mmol) by a method similar to that for the synthesis of 2,2,2-trichloroethyl (3-(hydroxymethyl)-2-methoxy-5-(trifluoromethyl)phenyl)carbamate (Reference Example 8).
MS(ESI) [M+H]⁺: 367.

Example 4

Synthesis of 1-(2-methoxy-5-(pentafluorosulfanyl)phenyl)-3-(trans-4-((2-morpholinopyrimidin-4-yl)oxy)cyclohexyl)urea

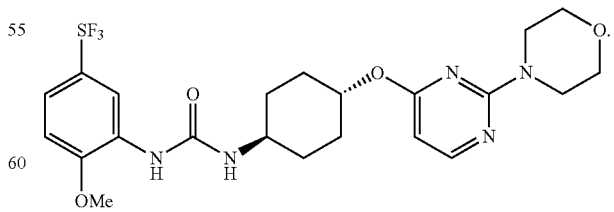

A solution of 2,2,2-trichloroethyl (2-methoxy-5-(pentafluorosulfanyl)phenyl)carbamate (0.046 g, 0.11 mmol), trans-4-((2-morpholinopyrimidin-4-yl)oxy)cyclohexanamine (0.020 g, 0.072 mmol) and DIPEA (0.038 mL, 0.22 mmol) in acetonitrile (5 mL) was stirred for 30 minutes at 150° C. by using the microwave synthesis reactor, and the reaction solution was then concentrated under vacuum. The obtained crude product was purified by silica gel column chromatography (eluent; chloroform:methanol=99:1→96:4) to obtain the title compound (0.032 g) (hereinafter referred to as the compound of Example 4).

$^1$H-NMR (400 MHz, CDCl$_3$) δ (ppm): 1.34-1.36 (2H, m), 1.59-1.62 (2H, m), 2.16-2.18 (4H, m), 3.74-3.77 (9H, m), 3.93 (3H, s), 4.46 (1H, d, J=7.8 Hz), 4.95 (1H, brs), 5.97 (1H, d, J=5.6 Hz), 6.76 (1H, s), 6.85 (1H, d, J=9.0 Hz), 7.37 (1H, dd, J=9.0, 2.7 Hz), 8.06 (1H, d, J=5.6 Hz), 8.69 (1H, d, J=2.7 Hz).

MS(ESI) [M+H]$^+$: 554.

Reference Example 102

Synthesis of 1-(trans-4-hydroxycyclohexyl)-3-(2-methoxy-5-(trifluoromethoxy)phenyl)urea

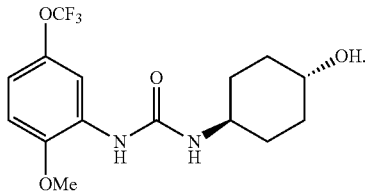 [SMILES: COc1ccc(OC(F)(F)F)cc1NC(=O)N[C@H]1CC[C@H](O)CC1]

The title compound (0.25 g) was obtained using 2,2,2-trichloroethyl (2-methoxy-5-(trifluoromethoxy)phenyl)carbamate (0.50 g, 1.3 mmol) and trans-4-aminohexanol (0.15 g, 1.3 mmol) by a method similar to that for the synthesis of 1-(2-methoxy-5-(pentafluorosulfanyl)phenyl)-3-(trans-4-((2-morpholinopyrimidin-4-yl)oxy)cyclohexyl)urea (Example 4).

$^1$H-NMR (400 MHz, CD$_3$OD) δ (ppm): 1.21-1.42 (4H, m), 1.96-1.99 (4H, m), 3.89 (3H, s), 6.79 (1H, ddd, J=8.8, 2.9, 0.9 Hz), 6.95 (1H, d, J=8.8 Hz), 8.07 (1H, dd, J=2.9, 1.0 Hz).

MS(ESI) [M+H]$^+$: 349.

Example 5

Synthesis of 1-(3-(hydroxymethyl)-2-methoxy-5-(pentafluorosulfanyl)phenyl)-3-(trans-4-((2-morpholinopyrimidin-4-yl)oxy)cyclohexyl)urea

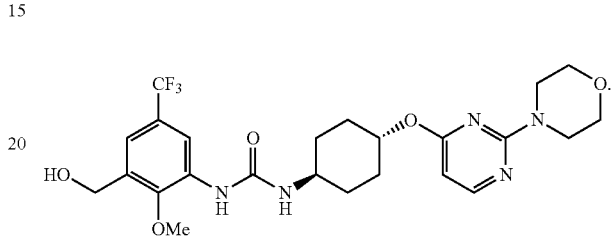

The title compound (0.029 g) (hereinafter referred to as the compound of Example 5) was obtained using 2,2,2-trichloroethyl (3-(hydroxymethyl)-2-methoxy-5-(pentafluorosulfanyl)phenyl)carbamate (0.033 g, 0.072 mmol) by a method similar to that for the synthesis of 1-(2-methoxy-5-(pentafluorosulfanyl)phenyl)-3-(trans-4-((2-morpholinopyrimidin-4-yl)oxy)cyclohexyl)urea (Example 4).

$^1$H-NMR (400 MHz, CDCl$_3$) δ (ppm): 1.36-1.38 (2H, m), 1.61-1.63 (2H, m), 1.89 (1H, t, J=6.1 Hz), 2.17-2.19 (4H, m), 3.74-3.77 (9H, m), 3.84 (3H, s), 4.55 (1H, d, J=7.1 Hz), 4.77 (2H, d, J=6.1 Hz), 4.96 (1H, brs), 5.98 (1H, d, J=5.9 Hz), 6.69 (1H, s), 7.50 (1H, d, J=2.7 Hz), 8.06 (1H, d, J=5.6 Hz), 8.59 (1H, d, J=2.7 Hz).

MS(ESI) [M+H]$^+$: 584.

Example 6

Synthesis of 1-(3-(hydroxymethyl)-2-methoxy-5-(trifluoromethyl)phenyl)-3-(trans-4-((2-morpholinopyrimidin-4-yl)oxy)cyclohexyl)urea

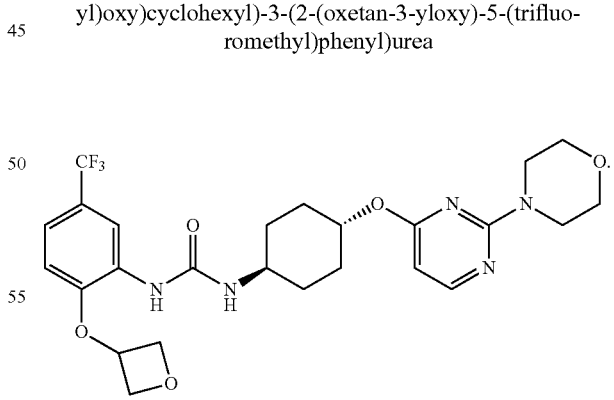

The title compound (0.025 g) (hereinafter referred to as the compound of Example 6) was obtained using 2,2,2-trichloroethyl (3-(hydroxymethyl)-2-methoxy-5-(trifluoromethyl)phenyl)carbamate (0.043 g, 0.11 mmol) by a method similar to that for the synthesis of 1-(2-methoxy-5-(pentafluorosulfanyl)phenyl)-3-(trans-4-((2-morpholinopyrimidin-4-yl)oxy)cyclohexyl)urea (Example 4).

$^1$H-NMR (400 MHz, CDCl$_3$) δ (ppm): 1.36-1.39 (2H, m), 1.61-1.64 (2H, m), 1.90 (1H, t, J=6.0 Hz), 2.17-2.19 (4H, m), 3.74-3.76 (9H, m), 3.84 (3H, s), 4.59 (1H, d, J=7.6 Hz), 4.77 (2H, d, J=5.9 Hz), 4.96 (1H, brs), 5.97 (1H, d, J=5.6 Hz), 6.74 (1H, s), 7.35 (1H, d, J=2.0 Hz), 8.06 (1H, d, J=5.6 Hz), 8.39 (1H, d, J=2.0 Hz).

MS(ESI) [M+H]$^+$: 526.

Example 7

Synthesis of 1-(trans-4-((2-morpholinopyrimidin-4-yl)oxy)cyclohexyl)-3-(2-(oxetan-3-yloxy)-5-(trifluoromethyl)phenyl)urea The title compound (0.049 g) (hereinafter referred to as the compound of Example 7) was obtained using 2,2,2-trichloroethyl (2-(oxetan-3-yloxy)-5-(trifluoromethyl)phenyl)carbamate (0.044 mg, 0.11 mmol) by a method similar to that for the synthesis of 1-(2-methoxy-5-(pentafluorosulfanyl)phenyl)-3-(trans-4-((2-morpholinopyrimidin-4-yl)oxy)cyclohexyl)urea (Example 4).

¹H-NMR (400 MHz, CDCl₃) δ (ppm): 1.36-1.41 (2H, m), 1.59-1.65 (2H, m), 2.17-2.20 (4H, m), 3.75 (9H, s), 4.65-4.78 (3H, m), 4.95-4.98 (1H, m), 5.04 (2H, t, J=6.8 Hz), 5.26-5.32 (1H, m), 5.98 (1H, d, J=5.6 Hz), 6.44 (1H, d, J=8.5 Hz), 6.85 (1H, s), 7.17 (1H, d, J=8.5 Hz), 8.06 (1H, d, J=5.9 Hz), 8.54 (1H, d, J=2.0 Hz).
MS(ESI) [M+H]⁺: 538.

Example 8

Synthesis of 1-(trans-4-((2-morpholinopyrimidin-4-yl)oxy)cyclohexyl)-3-(2-(3-oxopiperazin-1-yl)-5-(trifluoromethyl)phenyl)urea

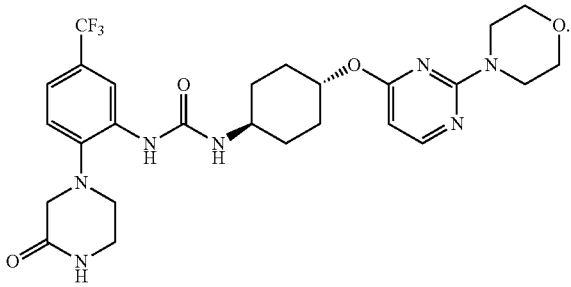 [SMILES: O=C1CN(c2ccc(C(F)(F)F)cc2NC(=O)N[C@H]2CC[C@H](Oc3ccnc(N4CCOCC4)n3)CC2)CCN1]

The title compound (0.027 g) (hereinafter referred to as the compound of Example 8) was obtained using 2,2,2-trichloroethyl (2-(3-oxopiperazin-1-yl)-5-(trifluoromethyl)phenyl)carbamate (0.030 g, 0.069 mmol) by a method similar to that for the synthesis of 1-(2-methoxy-5-(pentafluorosulfanyl)phenyl)-3-(trans-4-((2-morpholinopyrimidin-4-yl)oxy)cyclohexyl)urea (Example 4).
¹H-NMR (400 MHz, CDCl₃) δ (ppm): 1.38-1.40 (2H, m), 1.55-1.57 (2H, m), 2.16-2.18 (4H, m), 3.19 (2H, t, J=5.5 Hz), 3.53 (2H, brs), 3.58 (2H, s), 3.75 (9H, s), 4.96 (1H, brs), 5.97-5.98 (2H, m), 7.46 (1H, s), 8.06-8.07 (2H, m), 8.56 (1H, s).
MS(ESI) [M+H]⁺: 564.

Example 9

Synthesis of 1-(2-methoxy-5-(trifluoromethoxy)phenyl)-3-(trans-4-(pyrimidin-2-yloxy)cyclohexyl)urea

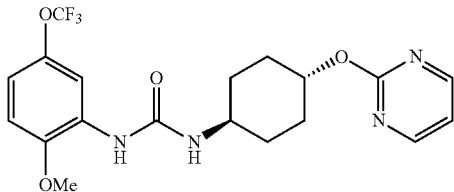

The title compound (0.018 g) (hereinafter referred to as the compound of Example 9) was obtained using 2,2,2-trichloroethyl (2-methoxy-5-(trifluoromethoxy)phenyl)carbamate (0.030 g, 0.078 mmol) and trans-4-(pyrimidin-2-yloxy)cyclohexanamine (0.015 g, 0.078 mmol) by a method similar to that for the synthesis of 1-(2-methoxy-5-(pentafluorosulfanyl)phenyl)-3-(trans-4-((2-morpholinopyrimidin-4-yl)oxy)cyclohexyl)urea (Example 4).

¹H-NMR (400 MHz, CDCl₃) δ (ppm): 1.36-1.39 (2H, m), 1.71-1.74 (2H, m), 2.17-2.20 (4H, m), 3.78 (1H, brs), 3.87 (3H, s), 4.48 (1H, brs), 4.97 (1H, brs), 6.79 (3H, brs), 6.91 (1H, brs), 8.15 (1H, brs), 8.50 (2H, brs).
MS(ESI) [M+H]⁺: 425.

Example 10

Synthesis of 1-(2-methoxy-5-(pentafluorosulfanyl)phenyl)-3-(trans-4-(pyrimidin-2-yloxy)cyclohexyl)urea

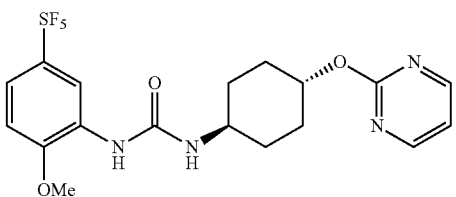

The title compound (0.040 g) (hereinafter referred to as the compound of Example 10) was obtained using 2,2,2-trichloroethyl (2-methoxy-5-(pentafluorosulfanyl)phenyl)carbamate (0.066 g, 0.16 mmol) and trans-4-(pyrimidin-2-yloxy)cyclohexanamine (0.020 g, 0.10 mmol) by a method similar to that for the synthesis of 1-(2-methoxy-5-(pentafluorosulfanyl)phenyl)-3-(trans-4-((2-morpholinopyrimidin-4-yl)oxy)cyclohexyl)urea (Example 4).
¹H-NMR (400 MHz, CDCl₃) δ (ppm): 1.35-1.38 (2H, m), 1.66-1.75 (2H, m), 2.16-2.19 (4H, m), 3.76-3.77 (1H, m), 3.90 (3H, s), 4.47 (1H, d, J=7.8 Hz), 4.92-4.94 (1H, m), 6.76 (1H, s), 6.81 (1H, d, J=9.3 Hz), 6.88 (1H, t, J=4.8 Hz), 7.34 (1H, dd, J=8.9, 2.8 Hz), 8.47 (1H, d, J=4.9 Hz), 8.68 (1H, d, J=2.7 Hz).
MS(ESI) [M+H]⁺: 469.

Example 11

Synthesis of 1-(2-methoxy-5-(trifluoromethyl)phenyl)-3-(trans-4-(pyrimidin-2-yloxy)cyclohexyl)urea

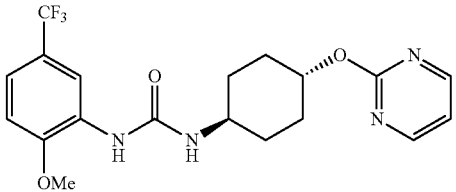

The title compound (0.032 g) (hereinafter referred to as the compound of Example 11) was obtained using 2,2,2-trichloroethyl (2-methoxy-5-(trifluoromethyl)phenyl)carbamate (0.057 g, 0.16 mmol) and trans-4-(pyrimidin-2-yloxy)cyclohexanamine (0.020 g, 0.10 mmol) by a method similar to that for the synthesis of 1-(2-methoxy-5-(pentafluorosulfanyl)phenyl)-3-(trans-4-((2-morpholinopyrimidin-4-yl)oxy)cyclohexyl)urea (Example 4).
¹H-NMR (400 MHz, CDCl₃) δ (ppm): 1.34-1.37 (2H, m), 1.68-1.71 (2H, m), 2.15-2.18 (4H, m), 3.76 (1H, s), 3.89 (3H, s), 4.45 (1H, brs), 4.94 (1H, brs), 6.79 (1H, brs), 6.87-6.88 (2H, m), 7.20-7.21 (1H, m), 8.46-8.48 (3H, m).

Example 12

Synthesis of 1-(3-(hydroxymethyl)-2-methoxy-5-(trifluoromethyl)phenyl)-3-(trans-4-(pyrimidin-2-yloxy)cyclohexyl)urea

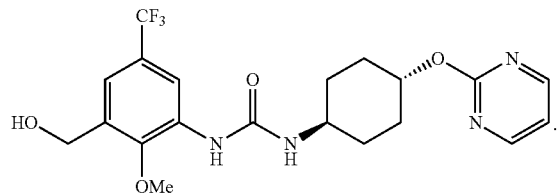 [SMILES: COc1c(CO)cc(C(F)(F)F)cc1NC(=O)N[C@H]1CC[C@H](Oc2ncccn2)CC1]

The title compound (0.045 g) (hereinafter referred to as the compound of Example 12) was obtained using 2,2,2-trichloroethyl (3-(hydroxymethyl)-2-methoxy-5-(trifluoromethyl)phenyl)carbamate (0.062 g, 0.16 mmol) and trans-4-(pyrimidin-2-yloxy)cyclohexanamine (0.020 g, 0.10 mmol) by a method similar to that for the synthesis of 1-(2-methoxy-5-(pentafluorosulfanyl)phenyl)-3-(trans-4-((2-morpholinopyrimidin-4-yl)oxy)cyclohexyl)urea (Example 4).

$^1$H-NMR (400 MHz, CDCl$_3$) δ (ppm): 1.35-1.38 (2H, m), 1.68-1.71 (2H, m), 1.92 (1H, brs), 2.16-2.20 (4H, m), 3.74 (1H, brs), 3.82 (3H, s), 4.58 (1H, brs), 4.74 (2H, d, J=5.6 Hz), 4.94 (1H, brs), 6.74 (1H, s), 6.88 (1H, t, J=4.9 Hz), 7.30-7.33 (1H, m), 8.39 (1H, d, J=1.7 Hz), 8.47-8.48 (2H, m).

MS(ESI) [M+H]$^+$: 439.

Example 13

Synthesis of 1-(2-(oxetan-3-yloxy)-5-(trifluoromethyl)phenyl)-3-(trans-4-(pyrimidin-2-yloxy)cyclohexyl)urea

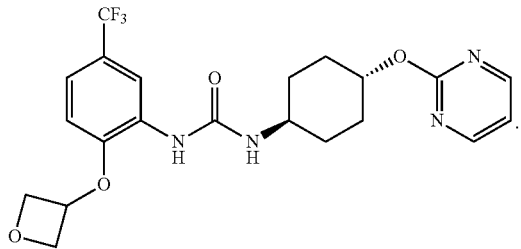 [SMILES: O=C(Nc1cc(C(F)(F)F)ccc1OC1COC1)N[C@H]1CC[C@H](Oc2ncccn2)CC1]

The title compound (0.042 g) (hereinafter referred to as the compound of Example 13) was obtained using 2,2,2-trichloroethyl (2-(oxetan-3-yloxy)-5-(trifluoromethyl)phenyl)carbamate (0.063 g, 0.16 mmol) and trans-4-(pyrimidin-2-yloxy)cyclohexanamine (0.020 g, 0.10 mmol) by a method similar to that for the synthesis of 1-(2-methoxy-5-(pentafluorosulfanyl)phenyl)-3-(trans-4-((2-morpholinopyrimidin-4-yl)oxy)cyclohexyl)urea (Example 4).

$^1$H-NMR (400 MHz, CDCl$_3$) δ (ppm): 1.41-1.44 (2H, m), 1.71-1.73 (2H, m), 2.21-2.24 (4H, m), 3.80 (1H, s), 4.58 (1H, d, J=7.3 Hz), 4.78 (2H, dd, J=8.3, 4.9 Hz), 5.03-5.05 (3H, m), 5.29-5.30 (1H, m), 6.44 (1H, d, J=8.3 Hz), 6.81 (1H, brs), 6.91 (1H, t, J=4.8 Hz), 7.17 (1H, d, J=6.8 Hz), 8.50 (2H, d, J=4.6 Hz), 8.56 (1H, d, J=1.7 Hz).

Example 14

Synthesis of 1-(2-(oxetan-3-yloxy)-5-(pentafluorosulfanyl)phenyl)-3-(trans-4-(pyrimidin-2-yloxy)cyclohexyl)urea

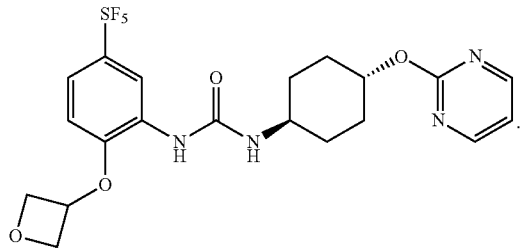

The title compound (0.042 g) (hereinafter referred to as the compound of Example 14) was obtained using 2,2,2-trichloroethyl (2-(oxetan-3-yloxy)-5-(pentafluorosulfanyl)phenyl)carbamate (0.072 g, 0.16 mmol) and trans-4-(pyrimidin-2-yloxy)cyclohexanamine (0.020 g, 0.10 mmol) by a method similar to that for the synthesis of 1-(2-methoxy-5-(pentafluorosulfanyl)phenyl)-3-(trans-4-((2-morpholinopyrimidin-4-yl)oxy)cyclohexyl)urea (Example 4).

$^1$H-NMR (400 MHz, CDCl$_3$) δ (ppm): 1.40-1.42 (2H, m), 1.72-1.75 (2H, m), 2.21-2.23 (4H, m), 4.57 (1H, d, J=7.3 Hz), 4.76-4.78 (2H, m), 5.03-5.05 (3H, m), 5.30 (1H, brs), 6.40 (1H, d, J=9.5 Hz), 6.77 (1H, s), 6.91 (1H, t, J=4.8 Hz), 7.31 (1H, dd, J=9.0, 2.7 Hz), 8.50 (2H, d, J=4.9 Hz), 8.77 (1H, d, J=2.7 Hz).

MS(ESI) [M−H]$^-$: 509.

Example 15

Synthesis of 1-(2-(3-oxopiperazin-1-yl)-5-(trifluoromethyl)phenyl)-3-(trans-4-(pyrimidin-2-yloxy)cyclohexyl)urea

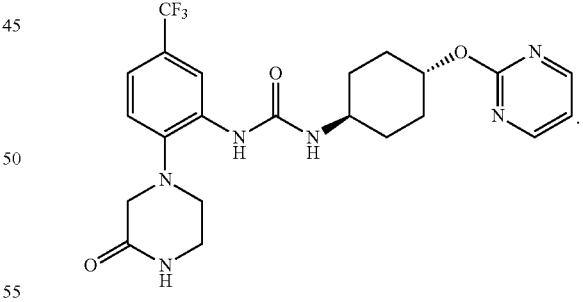

The title compound (0.023 g) (hereinafter referred to as the compound of Example 15) was obtained using 2,2,2-trichloroethyl (2-(3-oxopiperazin-1-yl)-5-(trifluoromethyl)phenyl)carbamate (0.068 g, 0.16 mmol) and trans-4-(pyrimidin-2-yloxy)cyclohexanamine (0.020 g, 0.10 mmol) by a method similar to that for the synthesis of 1-(2-methoxy-5-(pentafluorosulfanyl)phenyl)-3-(trans-4-((2-morpholinopyrimidin-4-yl)oxy)cyclohexyl)urea (Example 4).

$^1$H-NMR (400 MHz, CD$_3$OD) δ (ppm): 1.42-1.45 (2H, m), 1.65-1.69 (2H, m), 2.11-2.21 (4H, m), 3.19 (2H, t, J=5.2 Hz), 3.49 (2H, t, J=5.5 Hz), 3.53 (2H, s), 3.67 (1H, s), 5.04

(1H, d, J=3.9 Hz), 7.06 (1H, t, J=4.9 Hz), 7.30 (2H, dd, J=26.8, 8.3 Hz), 8.46 (1H, d, J=2.2 Hz), 8.54 (2H, d, J=4.9 Hz).

MS(ESI) [M+H]$^+$: 479.

Example 16

Synthesis of 1-(3-(hydroxymethyl)-2-methoxy-5-(trifluoromethyl)phenyl)-3-(4-((6-phenylpyridazin-3-yl)oxy)cyclohexyl)urea

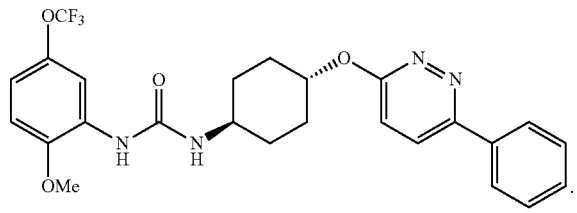 [SMILES: COc1ccc(OC(F)(F)F)cc1NC(=O)N[C@H]1CC[C@H](Oc2ccc(-c3ccccc3)nn2)CC1]

The title compound (0.017 g) (hereinafter referred to as the compound of Example 16) was obtained using 2,2,2-trichloroethyl (2-methoxy-5-(trifluoromethoxy)phenyl)carbamate (0.040 g, 0.10 mmol) and trans-4-(6-phenylpyridazin-3-yl)oxy)cyclohexanamine (0.014 g, 0.052 mmol) by a method similar to that for the synthesis of 1-(2-methoxy-5-(pentafluorosulfanyl)phenyl)-3-(trans-4-((2-morpholinopyrimidin-4-yl)oxy)cyclohexyl)urea (Example 4).

$^1$H-NMR (400 MHz, CDCl$_3$) δ (ppm): 1.41-1.44 (2H, m), 1.65-1.68 (2H, m), 2.17-2.21 (2H, m), 2.33-2.37 (2H, m), 3.82 (1H, brs), 3.87 (3H, s), 4.53 (1H, d, J=7.2 Hz), 5.33-5.36 (1H, m), 6.80-6.82 (2H, m), 7.01 (1H, d, J=9.1 Hz), 7.47-7.50 (3H, m), 7.80 (1H, d, J=9.1 Hz), 8.00-8.02 (2H, m), 8.17 (1H, s).

MS(ESI) [M−H]$^−$: 501.

Example 17

Synthesis of 1-(3-(hydroxymethyl)-2-methoxy-5-(trifluoromethyl)phenyl)-3-(4-((6-phenylpyridazin-3-yl)oxy)cyclohexyl)urea

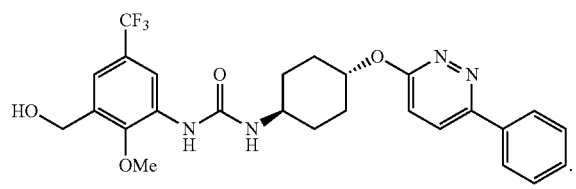 [SMILES: COc1c(CO)cc(C(F)(F)F)cc1NC(=O)N[C@H]1CC[C@H](Oc2ccc(-c3ccccc3)nn2)CC1]

The title compound (0.018 g) (hereinafter referred to as the compound of Example 17) was obtained using 2,2,2-trichloroethyl (3-(hydroxymethyl)-2-methoxy-5-(trifluoromethyl)phenyl)carbamate (0.041 g, 0.10 mmol) and trans-4-(6-phenylpyridazin-3-yl)oxy)cyclohexanamine (0.014 g, 0.052 mmol) by a method similar to that for the synthesis of 1-(2-methoxy-5-(pentafluorosulfanyl)phenyl)-3-(trans-4-((2-morpholinopyrimidin-4-yl)oxy)cyclohexyl)urea (Example 4).

$^1$H-NMR (400 MHz, CD$_3$OD) δ (ppm): 1.43-1.46 (2H, m), 1.66-1.69 (2H, m), 2.07-2.10 (2H, m), 2.24-2.27 (2H, m), 3.77-3.79 (4H, m), 4.68 (2H, s), 5.22-5.26 (1H, m), 7.18 (1H, d, J=9.3 Hz), 7.33 (1H, s), 7.47-7.49 (4H, m), 7.92-7.94 (2H, m), 8.01 (1H, d, J=9.3 Hz), 8.39 (1H, s).

Example 18

Synthesis of 1-(2-methoxy-5-(trifluoromethoxy)phenyl)-3-(trans-4-(pyridin-3-yloxy)cyclohexyl)urea

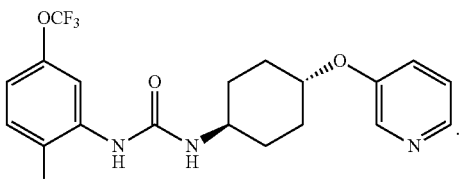

The title compound (0.012 g) (hereinafter referred to as the compound of Example 18) was obtained using 3-fluoropyridine (0.062 g, 0.63 mmol) and 1-(trans-4-hydroxycyclohexyl)-3-(2-methoxy-5-(trifluoromethoxy)phenyl)urea (0.20 g, 0.57 mmol) by a method similar to that for the synthesis of tert-butyl (trans-4-(pyridin-4-ylmethoxy)cyclohexyl)carbamate (Reference Example 67).

$^1$H-NMR (400 MHz, CDCl$_3$) δ (ppm): 1.22-1.37 (2H, m), 1.60-1.69 (2H, m), 2.16-2.18 (4H, m), 3.77-3.80 (1H, m), 3.85 (3H, s), 4.22-4.25 (1H, m), 4.70 (1H, brs), 6.78-6.81 (2H, m), 6.89-6.91 (1H, m), 7.20-7.21 (2H, m), 8.15 (1H, s), 8.20 (1H, dd, J=3.9, 2.0 Hz), 8.29 (1H, d, J=2.2 Hz).

MS(ESI) [M+H]$^+$: 426.

Example 19

Synthesis of 1-(2-methoxy-5-(trifluoromethoxy)phenyl)-3-(trans-4-(pyridin-4-ylmethoxy)cyclohexyl)urea

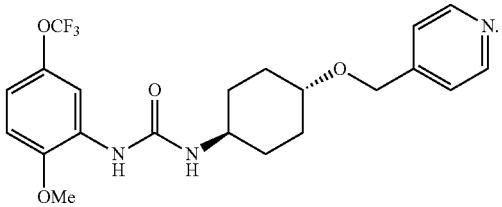 [SMILES: COc1ccc(OC(F)(F)F)cc1NC(=O)N[C@H]1CC[C@H](OCc2ccncc2)CC1]

The title compound (0.018 g) (hereinafter referred to as the compound of Example 19) was obtained using 2,2,2-trichloroethyl (2-methoxy-5-(trifluoromethoxy)phenyl)carbamate (0.042 g, 0.11 mmol) and trans-4-(pyridin-4-ylmethoxy)cyclohexanamine dihydrochloride (0.015 g, 0.073 mmol) by a method similar to that for the synthesis of 1-(2-methoxy-5-(pentafluorosulfanyl)phenyl)-3-(trans-4-((2-morpholinopyrimidin-4-yl)oxy)cyclohexyl)urea (Example 4).

$^1$H-NMR (400 MHz, CD$_3$OD) δ (ppm): 1.10-1.30 (2H, m), 1.40-1.50 (2H, m), 2.00-2.20 (4H, m), 3.40-3.50 (1H, m), 3.55-3.65 (1H, m), 3.89 (3H, s), 4.63 (2H, s), 6.79 (1H, d, J=8.0 Hz), 6.95 (1H, dd, J=8.0, 4.0 Hz), 7.41 (2H, bs), 8.07 (1H, s), 8.47 (2H, bs).

MS(ESI) [M+H]$^+$: 440.

Example 20

Synthesis of 1-(3-(hydroxymethyl)-5-(trifluoromethyl)phenyl)-3-(trans-4-(pyridin-4-ylmethoxy)cyclohexyl)urea

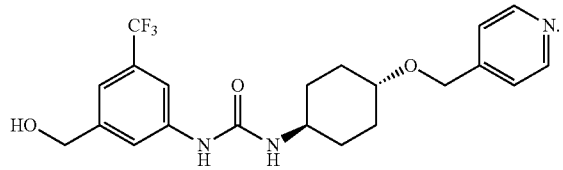 [SMILES: O=C(Nc1cc(CO)cc(C(F)(F)F)c1)N[C@H]1CC[C@H](OCc2ccncc2)CC1]

The title compound (0.017 g) (hereinafter referred to as the compound of Example 20) was obtained using 2,2,2-trichloroethyl (3-(hydroxymethyl)-5-(trifluoromethyl)phenyl)carbamate (0.030 g, 0.08 mmol) and trans-4-(pyridin-4-ylmethoxy)cyclohexanamine dihydrochloride (0.010 g, 0.048 mmol) by a method similar to that for the synthesis of 1-(2-methoxy-5-(pentafluorosulfanyl)phenyl)-3-(trans-4-((2-morpholinopyrimidin-4-yl)oxy)cyclohexyl)urea (Example 4).

$^1$H-NMR (400 MHz, CD$_3$OD) δ (ppm): 1.20-1.30 (2H, m), 1.40-1.50 (2H, m), 2.00-2.20 (4H, m), 3.40-3.50 (1H, m), 3.55-3.65 (1H, m), 4.61 (2H, s), 4.64 (2H, s), 7.23 (1H, s), 7.43 (2H, d, J=8.0 Hz), 7.47 (1H, s), 7.73 (1H, s), 8.47 (1H, d, J=8.0, 4.0 Hz).

MS(ESI) [M+H]$^+$: 424.

Example 21

Synthesis of 1-(3-(hydroxymethyl)-2-methoxy-5-(trifluoromethyl)phenyl)-3-(trans-4-(pyridin-4-ylmethoxy)cyclohexyl)urea

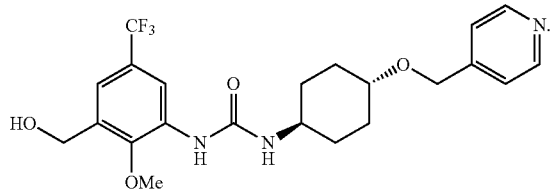 [SMILES: COc1c(CO)cc(C(F)(F)F)cc1NC(=O)N[C@H]1CC[C@H](OCc2ccncc2)CC1]

The title compound (0.017 g) (hereinafter referred to as the compound of Example 21) was obtained using 2,2,2-trichloroethyl (3-(hydroxymethyl)-2-methoxy-5-(trifluoromethyl)phenyl)carbamate (0.030 g, 0.076 mmol) and trans-4-(pyridin-4-ylmethoxy)cyclohexanamine dihydrochloride (0.010 g, 0.048 mmol) by a method similar to that for the synthesis of 1-(2-methoxy-5-(pentafluorosulfanyl)phenyl)-3-(trans-4-((2-morpholinopyrimidin-4-yl)oxy)cyclohexyl)urea (Example 4).

$^1$H-NMR (400 MHz, CD$_3$OD) δ (ppm): 1.25-1.40 (2H, m), 1.45-1.55 (2H, m), 2.00-2.20 (4H, m), 3.40-3.50 (1H, m), 3.55-3.65 (1H, m), 4.64 (2H, s), 4.72 (2H, s), 7.36 (1H, d, J=4.0 Hz), 7.43 (2H, d, J=4.0 Hz), 8.41 (1H, d, J=4.0 Hz), 8.47 (2H, dd, J=8.0, 4.0 Hz).

MS(ESI) [M+H]$^+$: 454.

Example 22

Synthesis of 1-(trans-4-(pyridin-4-ylmethoxy)cyclohexyl)-3-(3-(trifluoromethyl)phenyl)urea

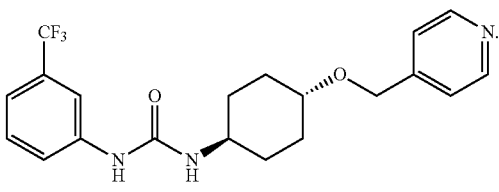 [SMILES: O=C(Nc1cccc(C(F)(F)F)c1)N[C@H]1CC[C@H](OCc2ccncc2)CC1]

The title compound (0.015 g) (hereinafter referred to as the compound of Example 22) was obtained using phenyl (3-(trifluoromethyl)phenyl)carbamate (0.030 g, 0.076 mmol) and trans-4-(pyridin-4-ylmethoxy)cyclohexanamine dihydrochloride (0.010 g, 0.048 mmol) by a method similar to that for the synthesis of 1-(2-methoxy-5-(pentafluorosulfanyl)phenyl)-3-(trans-4-((2-morpholinopyrimidin-4-yl)oxy)cyclohexyl)urea (Example 4).

$^1$H-NMR (400 MHz, CD$_3$OD) δ (ppm): 1.20-1.40 (2H, m), 1.40-1.50 (2H, m), 2.00-2.20 (4H, m), 3.40-3.50 (1H, m), 3.55-3.65 (1H, m), 4.64 (2H, s), 7.06 (1H, d, J=8.0 Hz), 7.22 (1H, d, J=8.0 Hz), 7.43 (3H, bs), 7.48 (1H, d, J=8.0 Hz), 7.81 (1H, s), 8.47 (2H, dd, J=8.0, 4.0 Hz).

MS(ESI) [M+H]$^+$: 394.

Example 23

Synthesis of 1-(4-(hydroxymethyl)-3-(trifluoromethyl)phenyl)-3-(trans-4-(pyridin-4-ylmethoxy)cyclohexyl)urea

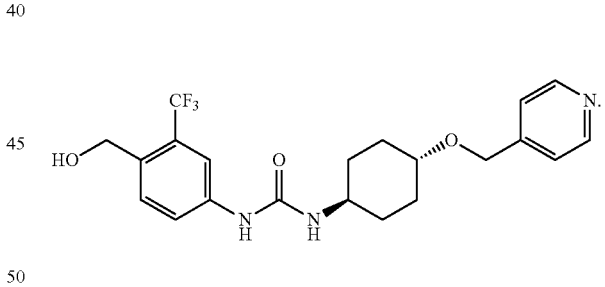

The title compound (0.015 g) (hereinafter referred to as the compound of Example 23) was obtained using 2,2,2-trichloroethyl (4-(hydroxymethyl)-3-(trifluoromethyl)phenyl)carbamate (0.030 g, 0.082 mmol) and trans-4-(pyridin-4-ylmethoxy)cyclohexanamine dihydrochloride (0.010 g, 0.048 mmol) by a method similar to that for the synthesis of 1-(2-methoxy-5-(pentafluorosulfanyl)phenyl)-3-(trans-4-((2-morpholinopyrimidin-4-yl)oxy)cyclohexyl)urea (Example 4).

$^1$H-NMR (400 MHz, DMSO-d$_6$) δ (ppm): 1.10-1.40 (4H, m), 2.00-2.20 (4H, m), 1.90-1.92 (2H, m), 2.00-2.10 (2H, m), 3.30-3.40 (1H, m), 3.45-3.55 (1H, m), 4.57 (4H, bs), 5.31 (1H, t, J=8.0 Hz), 6.16 (1H, d, J=8.0 Hz), 7.32 (2H, d, J=4.0 Hz), 7.47 (1H, d, J=8.0 Hz), 7.58 (1H, d, J=8.0 Hz), 7.91 (1H, s), 8.52 (2H, dd, J=8.0, 4.0 Hz), 8.61 (1H, s).

MS(ESI) [M+H]$^+$: 424.

Example 24

Synthesis of 1-(2-methoxy-5-(trifluoromethyl)phenyl)-3-(trans-4-(pyridin-4-ylmethoxy)cyclohexyl)urea

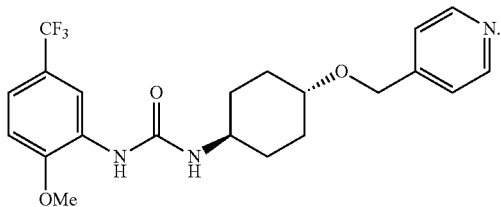 [SMILES: COc1ccc(C(F)(F)F)cc1NC(=O)N[C@H]1CC[C@H](OCc2ccncc2)CC1]

The title compound (0.018 g) (hereinafter referred to as the compound of Example 24) was obtained using 2,2,2-trichloroethyl (2-methoxy-5-(trifluoromethyl)phenyl)carbamate (0.030 g, 0.082 mmol) and trans-4-(pyridin-4-ylmethoxy)cyclohexanamine dihydrochloride (0.010 g, 0.048 mmol) by a method similar to that for the synthesis of 1-(2-methoxy-5-(pentafluorosulfanyl)phenyl)-3-(trans-4-((2-morpholinopyrimidin-4-yl)oxy)cyclohexyl)urea (Example 4).

$^1$H-NMR (400 MHz, CD$_3$OD) δ (ppm): 1.10-1.30 (2H, m), 1.40-1.50 (2H, m), 2.00-2.20 (4H, m), 3.40-3.50 (1H, m), 3.55-3.65 (1H, m), 3.94 (3H, s), 4.63 (2H, s), 7.06 (1H, d, J=8.0 Hz), 7.21 (1H, dd, J=8.0, 4.0 Hz), 7.43 (2H, d, J=8.0 Hz), 8.43 (1H, s), 8.47 (1H, dd, J=8.0, 4.0 Hz).

MS(ESI) [M+H]$^+$: 424.

Example 25

Synthesis of 1-(2-methyl-5-(trifluoromethyl)phenyl)-3-(trans-4-(pyridin-4-ylmethoxy)cyclohexyl)urea

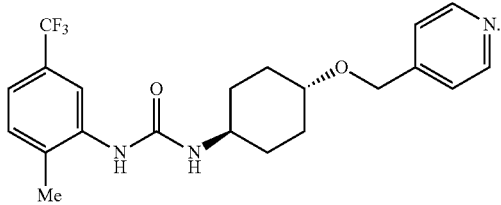 [SMILES: Cc1ccc(C(F)(F)F)cc1NC(=O)N[C@H]1CC[C@H](OCc2ccncc2)CC1]

The title compound (0.016 g) (hereinafter referred to as the compound of Example 25) was obtained using 2,2,2-trichloroethyl (2-methyl-5-(trifluoromethyl)phenyl)carbamate (0.030 g, 0.086 mmol) and trans-4-(pyridin-4-ylmethoxy)cyclohexanamine dihydrochloride (0.010 g, 0.048 mmol) by a method similar to that for the synthesis of 1-(2-methoxy-5-(pentafluorosulfanyl)phenyl)-3-(trans-4-((2-morpholinopyrimidin-4-yl)oxy)cyclohexyl)urea (Example 4).

$^1$H-NMR (400 MHz, CD$_3$OD) δ (ppm): 1.20-1.35 (2H, m), 1.45-1.55 (2H, m), 2.00-2.20 (4H, m), 2.29 (3H, s), 3.40-3.50 (1H, m), 3.55-3.65 (1H, m), 4.64 (2H, s), 7.06 (1H, d, J=8.0 Hz), 7.20 (1H, d, J=8.0 Hz), 7.31 (1H, d, J=8.0 Hz), 7.43 (2H, d, J=8.0 Hz), 8.13 (1H, s), 8.47 (1H, dd, J=8.0, 4.0 Hz).

MS(ESI) [M+H]$^+$: 408.

Example 26

Synthesis of 1-(2-methoxy-5-(pentafluorosulfanyl)phenyl)-3-(trans-4-(pyridin-4-ylmethoxy)cyclohexyl)urea

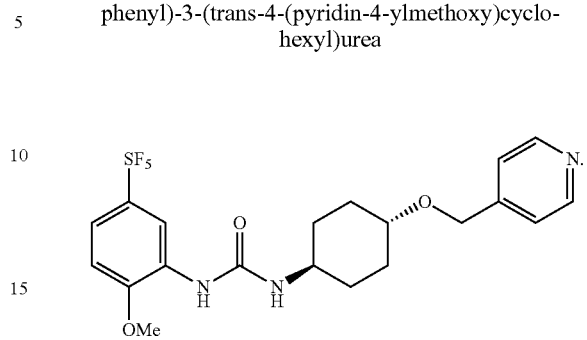

The title compound (0.005 g) (hereinafter referred to as the compound of Example 26) was obtained using 2,2,2-trichloroethyl (2-methyl-5-(pentafluorosulfanyl)phenyl)carbamate (0.030 g, 0.071 mmol) and trans-4-(pyridin-4-ylmethoxy)cyclohexanamine dihydrochloride (0.010 g, 0.048 mmol) by a method similar to that for the synthesis of 1-(2-methoxy-5-(pentafluorosulfanyl)phenyl)-3-(trans-4-((2-morpholinopyrimidin-4-yl)oxy)cyclohexyl)urea (Example 4).

$^1$H-NMR (400 MHz, CD$_3$OD) δ (ppm): 1.25-1.35 (2H, m), 1.45-1.55 (2H, m), 2.00-2.20 (4H, m), 3.40-3.50 (1H, m), 3.55-3.65 (1H, m), 3.95 (3H, s), 4.63 (2H, s), 7.04 (1H, d, J=8.0 Hz), 7.37 (1H, dd, J=8.0, 4.0 Hz), 7.42 (2H, d, J=8.0 Hz), 8.47 (2H, dd, J=8.0, 4.0 Hz), 8.67 (1H, bs).

MS(ESI) [M+H]$^+$: 482.

Example 27

Synthesis of 1-(2-fluoro-5-(trifluoromethyl)phenyl)-3-(trans-4-(pyridin-4-ylmethoxy)cyclohexyl)urea

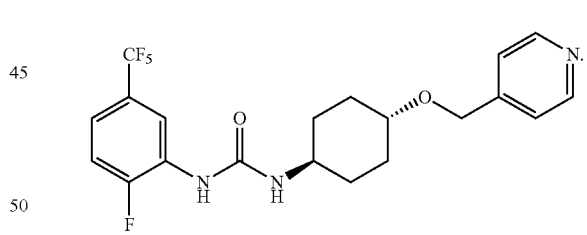

The title compound (0.017 g) (hereinafter referred to as the compound of Example 27) was obtained using 2,2,2-trichloroethyl (2-fluoro-5-(trifluoromethyl)phenyl)carbamate (0.030 g, 0.085 mmol) and trans-4-(pyridin-4-ylmethoxy)cyclohexanamine dihydrochloride (0.010 g, 0.048 mmol) by a method similar to that for the synthesis of 1-(2-methoxy-5-(pentafluorosulfanyl)phenyl)-3-(trans-4-((2-morpholinopyrimidin-4-yl)oxy)cyclohexyl)urea (Example 4).

$^1$H-NMR (400 MHz, CD$_3$OD) δ (ppm): 1.20-1.35 (2H, m), 1.45-1.55 (2H, m), 2.00-2.20 (4H, m), 3.40-3.50 (1H, m), 3.55-3.65 (1H, m), 4.64 (2H, s), 7.25-7.30 (2H, m), 7.42 (2H, d, J=8.0 Hz), 8.46-8.52 (3H, m).

MS(ESI) [M+H]$^+$: 412.

Example 28

Synthesis of 1-(2-morpholino-5-(trifluoromethyl)phenyl)-3-(trans-4-(pyridin-4-ylmethoxy)cyclohexyl)urea

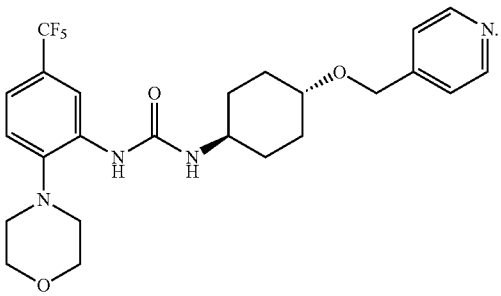

The title compound (0.015 g) (hereinafter referred to as the compound of Example 28) was obtained using 2,2,2-trichloroethyl (2-morpholino-5-(trifluoromethyl)phenyl)carbamate (0.032 g, 0.076 mmol) and trans-4-(pyridin-4-ylmethoxy)cyclohexanamine dihydrochloride (0.016 g, 0.076 mmol) by a method similar to that for the synthesis of 1-(2-methoxy-5-(pentafluorosulfanyl)phenyl)-3-(trans-4-((2-morpholinopyrimidin-4-yl)oxy)cyclohexyl)urea (Example 4).

$^1$H-NMR (400 MHz, CD$_3$OD) δ (ppm): 1.20-1.35 (2H, m), 1.40-1.50 (2H, m), 2.00-2.20 (4H, m), 2.80 (4H, bs), 3.40-3.50 (1H, m), 3.55-3.65 (1H, m), 3.88 (4H, bs), 4.62 (2H, s), 7.20 (2H, d, J=8.0 Hz), 7.30 (2H, d, J=8.0 Hz), 7.41 (2H, d, J=8.0 Hz), 8.39 (1H, s), 8.47 (2H, d, J=8.0 Hz).

MS(ESI) [M+H]$^+$: 479.

Example 29

Synthesis of 1-(2-chloro-5-(trifluoromethyl)phenyl)-3-(trans-4-(pyridin-4-ylmethoxy)cyclohexyl)urea

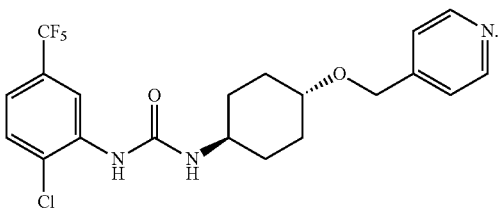

The title compound (0.015 g) (hereinafter referred to as the compound of Example 29) was obtained using 2,2,2-trichloroethyl (2-chloro-5-(trifluoromethyl)phenyl)carbamate (0.030 g, 0.081 mmol) and trans-4-(pyridin-4-ylmethoxy)cyclohexanamine dihydrochloride (0.010 g, 0.048 mmol) by a method similar to that for the synthesis of 1-(2-methoxy-5-(pentafluorosulfanyl)phenyl)-3-(trans-4-((2-morpholinopyrimidin-4-yl)oxy)cyclohexyl)urea (Example 4).

$^1$H-NMR (400 MHz, DMSO-d$_6$) δ (ppm): 1.15-1.25 (2H, m), 1.35-1.45 (2H, m), 1.90-2.00 (4H, m), 3.40-3.50 (1H, m), 3.55-3.65 (1H, m), 4.56 (2H, s), 7.19 (1H, d, J=8.0 Hz), 7.27 (1H, d, J=8.0 Hz), 7.33 (2H, d, J=4.0 Hz), 7.64 (1H, d, J=8.0 Hz), 8.25 (1H, s), 8.53 (2H, d, J=4.0 Hz), 8.66 (1H, bs).

MS(ESI) [M+H]$^+$: 428.

Example 30

Synthesis of 1-(2-(oxetan-3-yloxy)-5-(trifluoromethoxy)phenyl)-3-(trans-4-(pyridin-4-ylmethoxy)cyclohexyl)urea

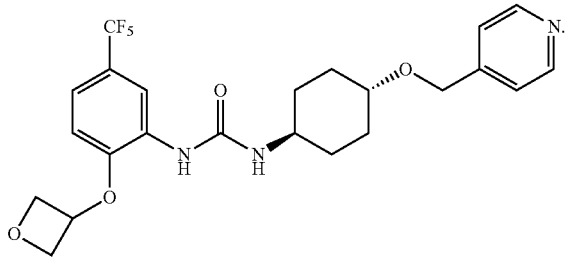

The title compound (0.013 g) (hereinafter referred to as the compound of Example 30) was obtained using 2,2,2-trichloroethyl (2-(oxetan-3-yloxy)-5-(trifluoromethoxy)phenyl)carbamate (0.040 g, 0.098 mmol) and trans-4-(pyridin-4-ylmethoxy)cyclohexanamine dihydrochloride (0.020 g, 0.098 mmol) by a method similar to that for the synthesis of 1-(2-methoxy-5-(pentafluorosulfanyl)phenyl)-3-(trans-4-((2-morpholinopyrimidin-4-yl)oxy)cyclohexyl)urea (Example 4).

$^1$H-NMR (400 MHz, DMSO-d$_6$) δ (ppm): 1.15-1.25 (2H, m), 1.30-1.40 (2H, m), 2.00-2.20 (4H, m), 3.30-3.40 (1H, m), 3.45-3.55 (1H, m), 3.94 (3H, s), 4.57 (2H, s), 4.61-4.65 (2H, m), 4.95 (2H, t, J=8.0 Hz), 5.30-5.35 (1H, m), 6.65 (1H, d, J=8.0 Hz), 6.78 (1H, dd, J=8.0, 4.0 Hz), 7.02 (1H, d, J=8.0 Hz), 7.31 (2H, d, J=8.0 Hz), 8.05 (1H, s), 8.24 (1H, bs), 8.52 (2H, dd, J=8.0, 4.0 Hz).

Reference Example 103

Synthesis of tert-butyl 3-(2-(3-(trans-4-(pyridin-4-ylmethoxy)cyclohexyl)ureido)-4-(trifluoromethyl)phenoxy)azetidine-1-carboxylate

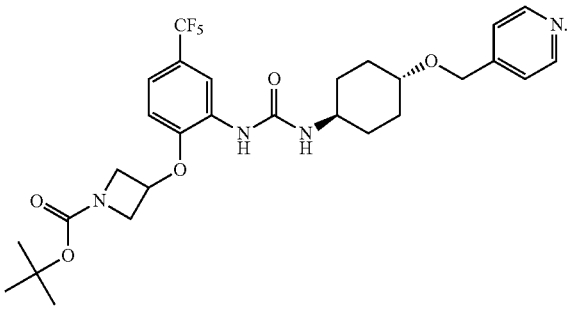

The title compound (0.032 g) was obtained using tert-butyl 3-(2-(((2,2,2-trichloroethyl)carbonyl)amino)-4-(trifluoromethyl)phenoxy)azetidine-1-carboxylate (0.050 g, 0.098 mmol) and trans-4-(pyridin-4-ylmethoxy)cyclohexanamine dihydrochloride (0.020 g, 0.098 mmol) by a method similar to that for the synthesis of 1-(2-methoxy-5-(pentafluorosulfanyl)phenyl)-3-(trans-4-((2-morpholinopyrimidin-4-yl)oxy)cyclohexyl)urea (Example 4).

MS(ESI) [M+H]$^+$: 565.

Reference Example 104

Synthesis of tert-butyl 4-(2-(3-(trans-4-(pyridin-4-ylmethoxy)cyclohexyl)ureido)-4-(trifluoromethyl)phenoxy)piperidine-1-carboxylate

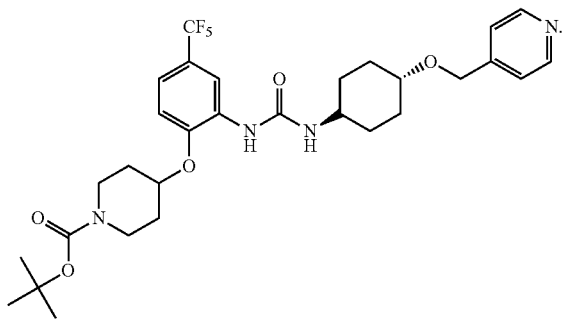

The title compound (0.025) was obtained using tert-butyl 4-(2-(((2,2,2-trichloroethoxy)carbonyl)amino)-4-(trifluoromethyl)phenoxy)piperidine-1-carboxylate (0.050 g, 0.093 mmol) and trans-4-(pyridin-4-ylmethoxy)cyclohexanamine dihydrochloride (0.019 g, 0.093 mmol) by a method similar to that for the synthesis of 1-(2-methoxy-5-(pentafluorosulfanyl)phenyl)-3-(trans-4-((2-morpholinopyrimidin-4-yl)oxy)cyclohexyl)urea (Example 4).

MS(ESI) [M+H]$^+$: 593.

Example 31

Synthesis of 1-(2-(azetidin-3-yloxy)-5-(trifluoromethyl)phenyl)-3-(trans-4-(pyridin-4-ylmethoxy)cyclohexyl)urea

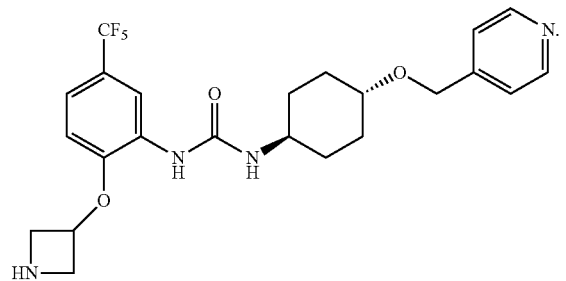

The title compound (0.015 g) (hereinafter referred to as the compound of Example 31) was obtained using tert-butyl 3-(2-(3-(trans-4-(pyridin-4-ylmethoxy)cyclohexyl)ureido)-4-(trifluoromethyl)phenoxy)azetidine-1-carboxylate (0.020 g, 0.035 mmol) by a method similar to that for the synthesis of trans-4-((2-morpholinopyrimidin-4-yl)oxy)cyclohexanamine (Reference Example 51).

$^1$H-NMR (400 MHz, CD$_3$OD) δ (ppm): 1.35-1.45 (2H, m), 1.48-1.58 (2H, m), 2.00-2.20 (4H, m), 3.50-3.75 (2H, m), 4.35 (2H, dd, J=8.0, 4.0 Hz), 4.57-4.61 (2H, m), 4.92 (2H, s), 5.25-5.30 (1H, m), 6.83 (1H, d, J=8.0 Hz), 7.21 (1H, dd, J=8.0, 4.0 Hz), 8.08 (2H, d, J=8.0 Hz), 8.51 (1H, s), 8.79 (2H, d, J=8.0 Hz).

MS(ESI) [M+H]$^+$: 465.

Example 32

Synthesis of 1-(2-(piperidin-4-yloxy)-5-(trifluoromethyl)phenyl)-3-(trans-4-(pyridin-4-ylmethoxy)cyclohexyl)urea

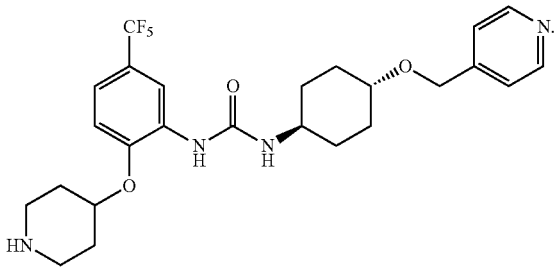

The title compound (0.015 g) (hereinafter referred to as the compound of Example 32) was obtained using tert-butyl 4-(2-(3-(trans-4-(pyridin-4-ylmethoxy)cyclohexyl)ureido)-4-(trifluoromethyl)phenoxy)piperidine-1-carboxylate (0.020 g, 0.034 mmol) by a method similar to that for the synthesis of trans-4-((2-morpholinopyrimidin-4-yl)oxy)cyclohexanamine (Reference Example 51).

$^1$H-NMR (400 MHz, CD$_3$OD) δ (ppm): 1.25-1.40 (2H, m), 1.45-1.55 (2H, m), 2.00-2.20 (4H, m), 3.19-3.26 (1H, m), 3.50-3.65 (2H, m), 4.92 (2H, dd, J=8.0, 4.0 Hz), 7.17 (1H, d, J=8.0 Hz), 7.23 (1H, d, J=8.0 Hz), 8.08 (2H, d, J=8.0 Hz), 8.43 (1H, s), 8.79 (2H, d, J=8.0 Hz).

MS(ESI) [M+H]$^+$: 493.

Example 33

Synthesis of 1-(2-((1-acetylazetidin-3-yl)oxy)-5-(trifluoromethyl)phenyl)-3-(trans-4-(pyridin-4-ylmethoxy)cyclohexyl)urea

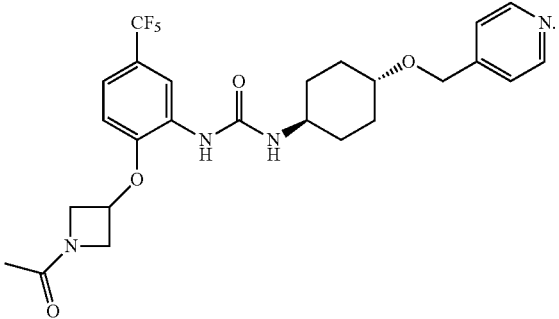

To a solution of 1-(2-(azetidin-3-yloxy)-5-(trifluoromethyl)phenyl)-3-(trans-4-(pyridin-4-ylmethoxy)cyclohexyl)urea (0.010 g, 0.022 mmol) and triethylamine (0.01 ml) in THF, acetic anhydride (0.01 ml) was added. After stirring the obtained solution at room temperature for 30 minutes, water was added to the reaction solution, and the obtained solution was extracted with ethyl acetate. The organic layer was sequentially washed with a saturated aqueous solution of ammonium chloride and with a saturated aqueous solution of sodium chloride. The obtained organic layer was dried over anhydrous sodium sulfate and then concentrated under vacuum, and the obtained crude product was purified by silica gel column chromatography (eluent; chloroform:

methanol=100:0→90:10) to obtain the title compound (0.0080 g) (hereinafter referred to as the compound of Example 33).

$^1$H-NMR (400 MHz, CD$_3$OD) δ (ppm): 1.15-1.25 (2H, m), 1.35-1.45 (2H, m), 1.81 (3H, s), 1.95-2.05 (4H, m), 3.31-3.40 (1H, m), 3.45-3.55 (1H, m), 4.00 (1H, dd, J=8.0, 4.0 Hz), 4.16 (1H, dd, J=8.0, 4.0 Hz), 4.32-4.36 (1H, m), 4.51 (2H, s), 4.50-4.60 (1H, m), 5.00-5.10 (1H, m), 6.71 (1H, d, J=8.0 Hz), 7.10 (1H, dd, J=8.0, 4.0 Hz), 7.31 (2H, d, J=8.0 Hz), 8.3 (2H, d, J=8.0 Hz), 8.41 (1H, s).

MS(ESI) [M+H]$^+$: 507.

Example 34

Synthesis of 1-(2-((1-acetylpiperidin-4-yl)oxy)-5-(trifluoromethyl)phenyl)-3-(trans-4-(pyridin-4-ylmethoxy)cyclohexyl)urea

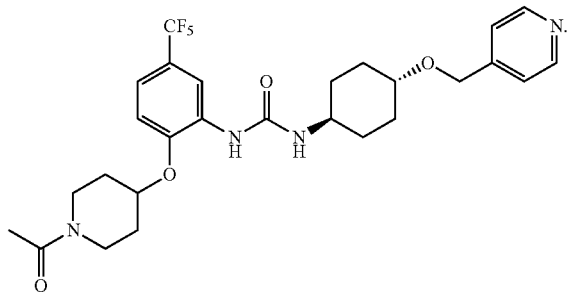

The title compound (0.007 g) (hereinafter referred to as the compound of Example 34) was obtained using tert-butyl 4-(2-(3-(trans-4-(pyridin-4-ylmethoxy)cyclohexyl)ureido)-4-(trifluoromethyl)phenoxy)piperidine-1-carboxylate (0.010 g, 0.020 mmol) by a method similar to that for the synthesis of 1-(2-((1-acetylazetidin-3-yl)oxy)-5-(trifluoromethyl)phenyl)-3-(trans-4-(pyridin-4-ylmethoxy)cyclohexyl)urea (Example 33).

$^1$H-NMR (400 MHz, CD$_3$OD) δ (ppm): 1.25-1.40 (2H, m), 1.45-1.50 (2H, m), 1.69-1.81 (2H, m), 1.98-2.05 (10H, m), 3.31-3.40 (2H, m), 3.50-3.60 (1H, m), 3.83-3.90 (1H, m), 4.09-4.15 (1H, m), 4.62 (2H, s), 4.75-4.80 (1H, m), 7.14-7.22 (2H, m), 7.42 (2H, d, J=4.0 Hz), 8.45-8.50 (3H, m).

MS(ESI) [M+H]$^+$: 535.

Example 35

Synthesis of 1-(trans-4-(pyridin-4-ylmethoxy)cyclohexyl)-3-(2-((R)-pyrrolidin-3-yloxy)-5-(trifluoromethyl)phenyl)urea

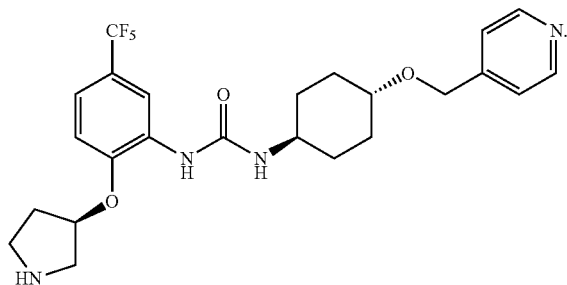

(R)-tert-butyl 3-(2-(((2,2,2-trichloroethyl)carbonyl)amino)-4-(trifluoromethyl)phenoxy)pyrrolidine-1-carboxylate (0.040 g, 0.077 mmol) and trans-4-(pyridin-4-ylmethoxy)cyclohexanamine dihydrochloride (0.015 g, 0.077 mmol) were used by a method similar to that for the synthesis of 1-(2-methoxy-5-(pentafluorosulfanyl)phenyl)-3-(trans-4-((2-morpholinopyrimidin-4-yl)oxy)cyclohexyl)urea (Example 4) to synthesize (R)-tert-butyl 3-(2-(3-(trans-4-(pyridin-4-ylmethoxy)cyclohexyl)ureido)-4-(trifluoromethyl)phenoxy)pyrrolidine-1-carboxylate, and the obtained product was used by a method similar to that for the synthesis of trans-4-((2-morpholinopyrimidin-4-yl)oxy)cyclohexanamine (Reference Example 51) to obtain the title compound (0.012 g) (hereinafter referred to as the compound of Example 35).

$^1$H-NMR (400 MHz, DMSO-d$_6$) δ (ppm): 1.20-1.36 (4H, m), 1.80-2.00 (3H, m) 2.80-2.95 (1H, m), 2.98-3.19 (3H, m), 4.57 (2H, s), 5.00 (1H, bs), 7.06-7.10 (2H, m), 7.18 (1H, d, J=4.0 Hz), 7.32 (2H, d, J=8.0 Hz), 7.80 (1H, s), 8.52 (2H, d, J=4.0 Hz), 8.55 (1H, d, J=4.0 Hz).

MS(ESI) [M+H]$^+$: 479.

Example 36

Synthesis of 1-(trans-4-(pyridin-4-ylmethoxy)cyclohexyl)-3-(2-((S)-pyrrolidin-3-yloxy)-5-(trifluoromethyl)phenyl)urea

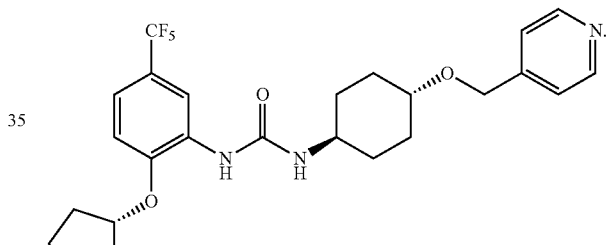

(S)-tert-butyl 3-(2-(((2,2,2-trichloroethyl)carbonyl)amino)-4-(trifluoromethyl)phenoxy)pyrrolidine-1-carboxylate (0.040 g, 0.077 mmol) and trans-4-(pyridin-4-ylmethoxy)cyclohexanamine dihydrochloride (0.015 g, 0.077 mmol) were used by a method similar to that for the synthesis of 1-(2-methoxy-5-(pentafluorosulfanyl)phenyl)-3-(trans-4-((2-morpholinopyrimidin-4-yl)oxy)cyclohexyl)urea (Example 4) to synthesize (S)-tert-butyl 34243-(trans-4-(pyridin-4-ylmethoxy)cyclohexyl)ureido)-4-(trifluoromethyl)phenoxy)pyrrolidine-1-carboxylate, and the obtained product was used by a method similar to that for the synthesis of trans-4-((2-morpholinopyrimidin-4-yl)oxy)cyclohexanamine (Reference Example 51) to obtain the title compound (0.014 g) (hereinafter referred to as the compound of Example 36).

$^1$H-NMR (400 MHz, DMSO-d$_6$) δ (ppm): 1.10-1.40 (4H, m), 1.70-1.85 (1H, m), 1.90-1.98 (2H, m), 2.0-2.1 (3H, m), 2.75-2.82 (1H, m), 2.90-3.10 (3H, m), 4.47 (2H, s), 4.98 (1H, bs), 7.06-7.10 (2H, m), 7.18 (1H, d, J=4.0 Hz), 7.32 (2H, d, J=8.0 Hz), 7.80 (1H, s), 8.52 (2H, d, J=4.0 Hz), 8.55 (1H, d, J=4.0 Hz).

MS(ESI) [M+H]$^+$: 479.

Example 37

Synthesis of 1-(2-methoxy-5-(trifluoromethyl)phenyl)-3-(trans-4-((2-(pyridin-3-yl)pyrimidin-4-yl)oxy)cyclohexyl)urea

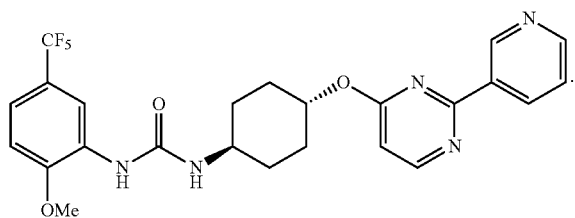

The title compound (0.015 g) (hereinafter referred to as the compound of Example 37) was obtained using 2,2,2-trichloroethyl (2-methoxy-5-(trifluoromethyl)phenyl)carbamate (0.020 g, 0.055 mmol) and trans-4-((2-(pyridin-3-yl)pyrimidin-4-yl)oxy)cyclohexanamine dihydrochloride (0.015 g, 0.055 mmol) by a method similar to that for the synthesis of 1-(2-methoxy-5-(pentafluorosulfanyl)phenyl)-3-(trans-4-((2-morpholinopyrimidin-4-yl)oxy)cyclohexyl)urea (Example 4).

$^1$H-NMR (400 MHz, DMSO-d$_6$) δ (ppm): 1.40-1.50 (2H, m), 1.55-1.65 (2H, m), 1.99-2.00 (2H, m), 2.17-2.20 (2H, m), 2.75-2.82 (1H, m), 3.56-3.61 (1H, m), 3.93 (3H, s), 5.25-5.31 (1H, m), 6.92 (1H, d, J=8.0 Hz), 7.06 (1H, d, J=8.0 Hz), 7.14 (1H, d, J=8.0 Hz), 7.23 (1H, d, J=8.0 Hz), 7.57 (1H, q, J=4.0 Hz), 8.18 (1H, s), 8.54 (1H, d, J=4.0 Hz), 8.60-8.70 (2H, m), 8.73 (1H, dd, J=8.0, 4.0 Hz), 9.50 (1H, d, J=4.0 Hz).

MS(ESI) [M+H]$^+$: 488.

Example 38

Synthesis of 1-(2-(oxetan-3-yloxy)-5-(trifluoromethyl)phenyl)-3-(trans-4-((2-(pyridin-3-yl)pyrimidin-4-yl)oxy)cyclohexyl)urea

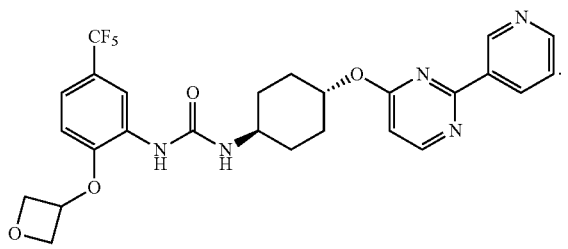

The title compound (0.018 g) (hereinafter referred to as the compound of Example 38) was obtained using 2,2,2-trichloroethyl (2-(oxetan-3-yloxy)-5-(trifluoromethyl)phenyl)carbamate (0.020 g, 0.049 mmol) and trans-4-((2-(pyridin-3-yl)pyrimidin-4-yl)oxy)cyclohexanamine dihydrochloride (0.013 g, 0.049 mmol) by a method similar to that for the synthesis of 1-(2-methoxy-5-(pentafluorosulfanyl)phenyl)-3-(trans-4-((2-morpholinopyrimidin-4-yl)oxy)cyclohexyl)urea (Example 4).

$^1$H-NMR (400 MHz, DMSO-d$_6$) δ (ppm): 1.40-1.50 (2H, m), 1.55-1.65 (2H, m), 1.99-2.00 (2H, m), 2.17-2.20 (2H, m), 2.75-2.82 (1H, m), 3.56-3.61 (1H, m), 4.65-4.75 (2H, m), 4.98 (2H, t, J=8.0 Hz), 5.25-5.31 (1H, m), 5.40-5.45 (1H, m), 6.77 (1H, d, J=8.0 Hz), 6.90-6.95 (1H, m), 7.10 (1H, d, J=8.0 Hz), 7.17 (1H, d, J=8.0 Hz), 7.57 (1H, q, J=4.0 Hz), 8.15 (1H, s), 8.59 (1H, s), 8.63-8.66 (2H, m), 8.73 (1H, dd, J=8.0, 4.0 Hz), 9.50 (1H, d, J=4.0 Hz).

MS(ESI) [M+H]$^+$: 530.

Example 39

Synthesis of 1-(2-methoxy-5-(trifluoromethoxy)phenyl)-3-(trans-4-((2-(pyridin-3-yl)pyrimidin-4-yl)oxy)cyclohexyl)urea

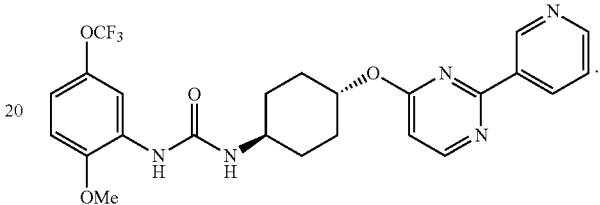

The title compound (0.017 g) (hereinafter referred to as the compound of Example 39) was obtained using 2,2,2-trichloroethyl (2-methoxy-5-(trifluoromethoxy)phenyl)carbamate (0.020 g, 0.052 mmol) and trans-4-((2-(pyridin-3-yl)pyrimidin-4-yl)oxy)cyclohexanamine dihydrochloride (0.014 g, 0.052 mmol) by a method similar to that for the synthesis of 1-(2-methoxy-5-(pentafluorosulfanyl)phenyl)-3-(trans-4-((2-morpholinopyrimidin-4-yl)oxy)cyclohexyl)urea (Example 4).

$^1$H-NMR (400 MHz, DMSO-d$_6$) δ (ppm): 1.40-1.50 (2H, m), 1.55-1.65 (2H, m), 1.99-2.00 (2H, m), 2.17-2.20 (2H, m), 3.56-3.61 (1H, m), 3.88 (3H, s), 5.25-5.31 (1H, m), 6.84 (1H, d, J=8.0 Hz), 6.91 (1H, d, J=8.0 Hz), 7.03 (1H, d, J=8.0 Hz), 7.06 (1H, d, J=8.0 Hz), 7.57 (1H, q, J=4.0 Hz), 8.15 (1H, s), 8.21 (1H, d, J=4.0 Hz), 8.60-8.70 (2H, m), 8.73 (1H, dd, J=8.0, 4.0 Hz), 9.50 (1H, d, J=4.0 Hz).

MS(ESI) [M+H]$^+$: 504.

Example 40

Synthesis of 1-(2-methoxy-5-(trifluoromethyl)phenyl)-3-(trans-4-((4-(pyridin-3-yl)pyrimidin-2-yl)oxy)cyclohexyl)urea

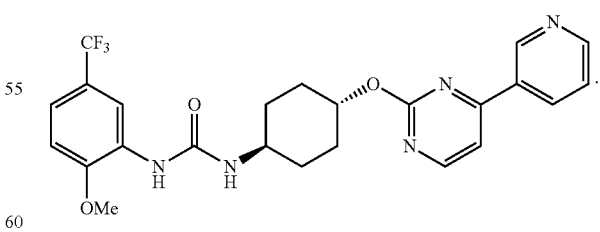

The title compound (0.018 g) (hereinafter referred to as the compound of Example 40) was obtained using 2,2,2-trichloroethyl (2-methoxy-5-(trifluoromethyl)phenyl)carbamate (0.020 g, 0.055 mmol) and trans-4-((4-(pyridin-3-yl)pyrimidin-2-yl)oxy)cyclohexanamine dihydrochloride (0.015 g, 0.055 mmol) by a method similar to that for the synthesis of 1-(2-methoxy-5-(pentafluorosulfanyl)phenyl)-3-(trans-4-((2-morpholinopyrimidin-4-yl)oxy)cyclohexyl) urea (Example 4).

$^1$H-NMR (400 MHz, DMSO-$d_6$) δ (ppm): 1.35-1.45 (2H, m), 1.55-1.65 (2H, m), 1.99-2.00 (2H, m), 2.17-2.20 (2H, m), 3.56-3.61 (1H, m), 3.93 (3H, s), 5.05-5.12 (1H, m), 7.05 (1H, d, J=8.0 Hz), 7.14 (1H, d, J=8.0 Hz), 7.23 (1H, d, J=8.0 Hz), 7.60 (1H, q, J=4.0 Hz), 7.80 (1H, d, J=4.0 Hz), 8.17 (1H, s), 8.50-8.55 (2H, m), 8.72 (1H, d, J=8.0 Hz), 8.75 (1H, d, J=8.0, 4.0 Hz), 9.35 (1H, d, J=4.0 Hz).

MS(ESI) [M+H]$^+$: 488.

Example 41

Synthesis of 1-(2-(oxetan-3-yloxy)-5-(trifluoromethyl)phenyl)-3-(trans-4-((4-(pyridin-3-yl)pyrimidin-2-yl)oxy)cyclohexyl)urea

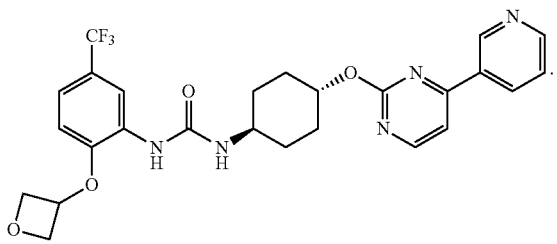 [SMILES: O=C(Nc1cc(C(F)(F)F)ccc1OC1COC1)N[C@H]1CC[C@H](Oc2nccc(-c3cccnc3)n2)CC1]

The title compound (0.016 g) (hereinafter referred to as the compound of Example 41) was obtained using 2,2,2-trichloroethyl (2-(oxetan-3-yloxy)-5-(trifluoromethyl)phenyl)carbamate (0.020 g, 0.049 mmol) and trans-4-((4-(pyridin-3-yl)pyrimidin-2-yl)oxy)cyclohexanamine dihydrochloride (0.013 g, 0.049 mmol) by a method similar to that for the synthesis of 1-(2-methoxy-5-(pentafluorosulfanyl)phenyl)-3-(trans-4-((2-morpholinopyrimidin-4-yl)oxy)cyclohexyl)urea (Example 4).

$^1$H-NMR (400 MHz, DMSO-$d_6$) δ (ppm): 1.40-1.50 (2H, m), 1.55-1.65 (2H, m), 1.99-2.00 (2H, m), 2.17-2.20 (2H, m), 3.56-3.61 (1H, m), 4.65-4.70 (2H, m), 5.00 (2H, t, J=8.0 Hz), 5.10-5.15 (1H, m), 5.40-5.45 (1H, m), 6.77 (1H, d, J=8.0 Hz), 7.09 (1H, d, J=8.0 Hz), 7.17 (1H, d, J=8.0 Hz), 7.57 (1H, q, J=4.0 Hz), 7.80 (1H, d, J=8.0 Hz), 8.14 (1H, s), 8.32 (1H, s), 8.51 (1H, dt, J=8.0, 4.0 Hz), 8.60 (1H, d, J=4.0 Hz), 8.71 (1H, d, J=8.0 Hz), 8.75 (1H, dd, J=8.0, 4.0 Hz), 9.35 (1H, d, J=4.0 Hz).

MS(ESI) [M+H]$^+$: 530.

Example 42

Synthesis of 1-(2-(azetidin-3-yloxy)-5-(trifluoromethoxy)phenyl)-3-(trans-4-((6-(methylamine-o)pyrimidin-4-yl)oxy)cyclohexyl)urea

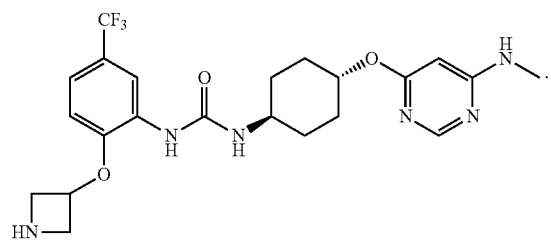 [SMILES: CNc1cc(O[C@H]2CC[C@H](NC(=O)Nc3cc(C(F)(F)F)ccc3OC3CNC3)CC2)ncn1]

tert-Butyl 3-(2-(((2,2,2-trichloroethyl)carbonyl)amino)-4-(trifluoromethyl)phenoxy)azetidine-1-carboxylate (0.050 g, 0.098 mmol) and 6-((trans-4-aminocyclohexyl)oxy)-N-methylpyrimidin-4-amine dihydrochloride (0.022 g, 0.098 mmol) were used by a method similar to that for the synthesis of 1-(2-methoxy-5-(pentafluorosulfanyl)phenyl)-3-(trans-4-((2-morpholinopyrimidin-4-yl)oxy)cyclohexyl) urea (Example 4) to synthesize tert-butyl 3-(2-(3-(trans-4-((6-(methylamino)pyrimidin-4-yl)oxy)cyclohexyl)ureido)-4-(trifluoromethyl)phenoxy)azetidine-1-carboxylate, and the obtained product was used by a method similar to that for the synthesis of trans-4-((2-morpholinopyrimidin-4-yl)oxy) cyclohexanamine (Reference Example 51) to obtain the title compound (0.021 g) (hereinafter referred to as the compound of Example 42).

$^1$H-NMR (400 MHz, DMSO-$d_6$) δ (ppm): 1.29-1.37 (2H, m), 1.44-1.55 (2H, m), 1.96-2.10 (4H, m), 2.4 (3H, s), 3.50-3.57 (2H, m), 3.63 (2H, t, J=8.0 Hz), 3.86 (2H, t, J=8.0 Hz), 4.95 (1H, bs), 5.11 (1H, t, J=8.0 Hz), 5.65 (1H, s), 6.81 (1H, d, J=8.0 Hz), 7.05 (1H, d, J=8.0 Hz), 7.10-7.20 (2H, d, J=8.0 Hz), 8.07 (1H, s), 8.14 (1H, s), 8.58 (1H, s).

MS(ESI) [M+H]$^+$: 481.

Example 43

Synthesis of 1-(trans-4-((6-(methylamino)pyrimidin-4-yl)oxy)cyclohexyl)-3-(2-(piperidin-4-yloxy)-5-(trifluoromethoxy)phenyl)urea

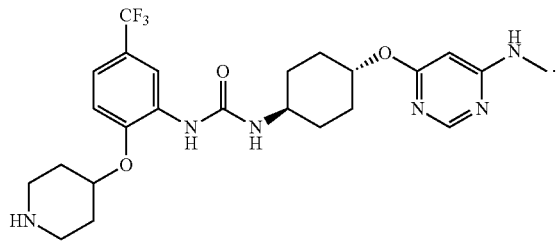 [SMILES: CNc1cc(O[C@H]2CC[C@H](NC(=O)Nc3cc(C(F)(F)F)ccc3OC3CCNCC3)CC2)ncn1]

tert-Butyl 4-(2-(((2,2,2-trichloroethoxy)carbonyl)amino)-4-(trifluoromethyl)phenoxy)piperidine-1-carboxylate (0.050 g, 0.093 mmol) and 6-((trans-4-aminocyclohexyl)oxy)-N-methylpyrimidin-4-amine dihydrochloride (0.020 g, 0.093 mmol) were used by a method similar to that for the synthesis of 1-(2-methoxy-5-(pentafluorosulfanyl)phenyl)-3-(trans-4-((2-morpholinopyrimidin-4-yl)oxy)cyclohexyl) urea (Example 4) to synthesize tert-butyl 44243-(trans-4-((6-(methylamino)pyrimidin-4-yl)oxy)cyclohexyl)ureido)-4-(trifluoromethyl)phenoxy)piperidine-1-carboxylate, and the obtained product was used by a method similar to that for the synthesis of trans-4-((2-morpholinopyrimidin-4-yl)oxy) cyclohexanamine (Reference Example 51) to obtain the title compound (0.012 g) (hereinafter referred to as the compound of Example 43).

$^1$H-NMR (400 MHz, DMSO-$d_6$) δ (ppm): 1.34-1.45 (2H, m), 1.51-1.59 (2H, m), 1.96-2.10 (4H, m), 2.87 (3H, s), 3.50-3.57 (2H, m), 3.06 (2H, bs), 3.86 (2H, t, J=8.0 Hz), 4.82 (1H, bs), 6.06 (1H, s), 7.10-7.20 (2H, d, J=8.0 Hz), 8.21 (1H, s), 8.30 (1H, s), 8.41 (1H, s), 8.55 (1H, s).

MS(ESI) [M+H]$^+$: 509.

Example 44

Synthesis of 1-(trans-4-((2-morpholinopyrimidin-4-yl)oxy)cyclohexyl)-3-(2-(oxetan-3-yloxy)-5-(trifluoromethoxy)phenyl)urea

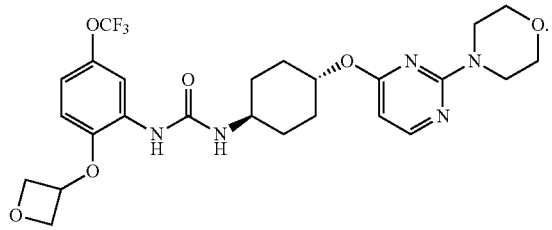 [SMILES: O=C(Nc1cc(OC(F)(F)F)ccc1OC1COC1)N[C@H]1CC[C@H](Oc2ccnc(N3CCOCC3)n2)CC1]

The title compound (0.020 g) (hereinafter referred to as the compound of Example 44) was obtained using 2,2,2-trichloroethyl (2-(oxetan-3-yloxy)-5-(trifluoromethoxy)phenyl)carbamate (0.020 g, 0.047 mmol) by a method similar to that for the synthesis of 1-(2-methoxy-5-(pentafluorosulfanyl)phenyl)-3-(trans-4-((2-morpholinopyrimidin-4-yl)oxy)cyclohexyl)urea (Example 4).

$^1$H-NMR (400 MHz, DMSO-$d_6$) δ (ppm): 1.30-1.40 (2H, m), 1.45-1.55 (2H, m), 1.96-2.10 (4H, m), 3.54-3.52 (4H, m), 3.66 (8H, s), 4.62-4.65 (2H, m), 4.96 (3H, t, J=8.0 Hz), 5.31-5.40 (1H, m), 6.06 (1H, d, J=8.0 Hz), 6.66 (1H, d, J=8.0 Hz), 6.78 (1H, dd, J=8.0, 4.0 Hz), 7.05 (1H, d, J=8.0 Hz), 8.06 (1H, s), 8.10 (1H, d, J=8.0 Hz), 8.24 (1H, d, J=4.0 Hz). MS(ESI) [M+H]$^+$: 554.

Example 45

Synthesis of 1-(3-(hydroxymethyl)-2-methoxy-5-(trifluoromethyl)phenyl)-3-(trans-4-((2-(pyridin-3-yl)pyrimidin-4-yl)oxy)cyclohexyl)urea

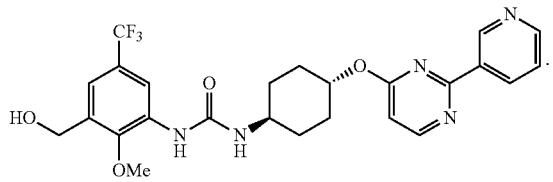 [SMILES: COc1c(CO)cc(C(F)(F)F)cc1NC(=O)N[C@H]1CC[C@H](Oc2ccnc(-c3cccnc3)n2)CC1]

The title compound (0.014 g) (hereinafter referred to as the compound of Example 45) was obtained using 2,2,2-trichloroethyl (3-(hydroxymethyl)-2-methoxy-5-(trifluoromethyl)phenyl)carbamate (0.050 g, 0.050 mmol) and trans-4-((2-(pyridin-3-yl)pyrimidin-4-yl)oxy)cyclohexanamine dihydrochloride (0.013 g, 0.050 mmol) by a method similar to that for the synthesis of 1-(2-methoxy-5-(pentafluorosulfanyl)phenyl)-3-(trans-4-((2-morpholinopyrimidin-4-yl)oxy)cyclohexyl)urea (Example 4).

$^1$H-NMR (400 MHz, DMSO-$d_6$) δ (ppm): 1.39-1.51 (2H, m), 1.58-1.67 (2H, m), 1.99-2.02 (2H, m), 2.17-2.20 (2H, m), 3.53-3.62 (1H, m), 3.77 (3H, s), 4.59 (2H, d, J=8.0 Hz), 5.25-5.31 (1H, m), 5.37 (1H, t, J=8.0 Hz), 6.90 (1H, d, J=8.0 Hz), 7.07 (1H, d, J=8.0 Hz), 7.30 (1H, d, J=4.0 Hz), 7.57 (1H, q, J=4.0 Hz), 8.28 (1H, s), 8.53 (1H, d, J=4.0 Hz), 8.60-8.67 (2H, m), 8.73 (1H, dd, J=8.0, 4.0 Hz), 9.50 (1H, d, J=4.0 Hz).

Example 46

Synthesis of 1-(2-ethoxy-5-(trifluoromethyl)phenyl)-3-(trans-4-((2-morpholinopyrimidin-4-yl)oxy)cyclohexyl)urea

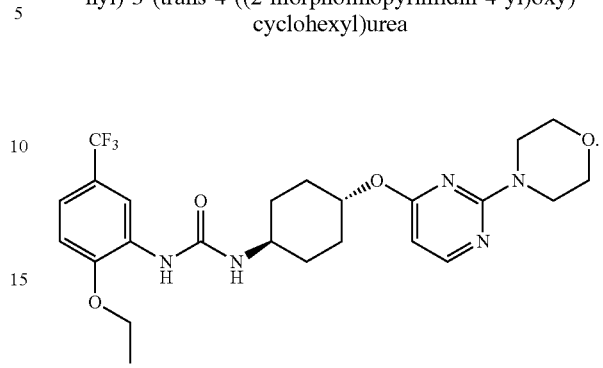

The title compound (0.026 g) (hereinafter referred to as the compound of Example 46) was obtained using 2,2,2-trichloroethyl (2-ethoxy-5-(trifluoromethyl)phenyl)carbamate (0.040 g, 0.11 mmol) by a method similar to that for the synthesis of 1-(2-methoxy-5-(pentafluorosulfanyl)phenyl)-3-(trans-4-((2-morpholinopyrimidin-4-yl)oxy)cyclohexyl)urea (Example 4).

$^1$H-NMR (400 MHz, DMSO-$d_6$) δ (ppm): 1.30-1.53 (4H, m), 1.42 (3H, t, J=8.0 Hz), 1.95-2.08 (4H, m), 3.50-3.53 (1H, m), 3.66 (s, 8H), 4.18 (2H, q, J=8.0 Hz), 4.94-4.99 (1H, m), 6.06 (1H, d, J=4.0 Hz), 7.11 (2H, d, J=4.0 Hz), 7.20 (1H, dd, J=8.0, 4.0 Hz), 7.96 (1H, s), 8.10 (1H, d, J=8.0 Hz), 8.53 (1H, d, J=4.0 Hz).

Example 47

Synthesis of 1-(2-(oxetan-3-yloxy)-5-(trifluoromethyl)phenyl)-3-(trans-4-((2-(pyridin-4-yl)pyrimidin-4-yl)oxy)cyclohexyl)urea

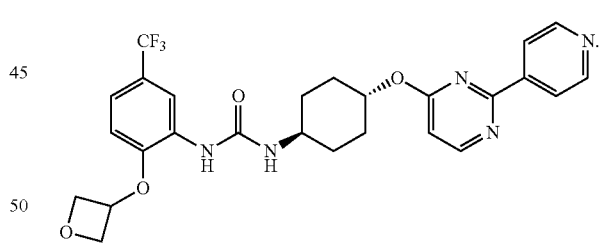

The title compound (0.010 g) (hereinafter referred to as the compound of Example 47) was obtained using 2,2,2-trichloroethyl (2-(oxetan-3-yloxy)-5-(trifluoromethyl)phenyl)carbamate (0.020 g, 0.049 mmol) and trans-4-((4-(pyridin-3-yl)pyrimidin-4-yl)oxy)cyclohexanamine dihydrochloride (0.013 g, 0.049 mmol) by a method similar to that for the synthesis of 1-(2-methoxy-5-(pentafluorosulfanyl)phenyl)-3-(trans-4-(2-morpholinopyrimidin-4-yl)oxy)cyclohexyl)urea (Example 4).

$^1$H-NMR (400 MHz, DMSO-$d_6$) δ (ppm): 1.40-1.66 (4H, m), 1.99-2.05 (2H, m), 2.19-2.21 (2H, m), 3.58-3.62 (1H, m), 4.65-4.70 (2H, m), 5.00 (2H, t, J=8.0 Hz), 5.26-5.32 (1H, m), 5.40-5.46 (1H, m), 6.76 (1H, d, J=8.0 Hz), 6.97 (1H, d, J=8.0 Hz), 7.11 (1H, d, J=8.0 Hz), 7.17 (1H, dd, J=8.0, 4.0 Hz), 8.15 (1H, s), 8.24 (2H, dd, J=8.0, 4.0 Hz), 8.59 (1H, d, J=4.0 Hz), 8.69 (1H, d, J=8.0 Hz), 8.78 (2H, dd, J=8.0, 4.0 Hz).

Example 48

Synthesis of 1-(2-methoxy-5-(trifluoromethoxy)phenyl)-3-(trans-4-((2-morpholinopyridin-4-yl)oxy)cyclohexyl)urea

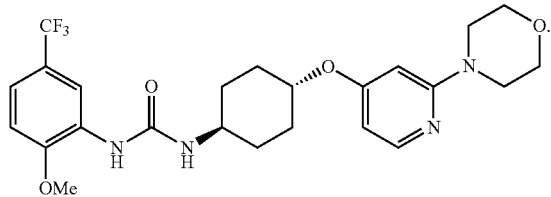 [SMILES: COc1ccc(C(F)(F)F)cc1NC(=O)N[C@H]1CC[C@H](Oc2ccnc(N3CCOCC3)c2)CC1]

The title compound (0.010 g) (hereinafter referred to as the compound of Example 48) was obtained using 2,2,2-trichloroethyl (2-methoxy-5-(trifluoromethoxy)phenyl)carbamate (0.021 g, 0.054 mmol) and trans-4-((2-morpholinopyridin-4-yl)oxy)cyclohexanamine dihydrochloride (0.010 g, 0.036 mmol) by a method similar to that for the synthesis of 1-(2-methoxy-5-(pentafluorosulfanyl)phenyl)-3-(trans-4-((2-morpholinopyrimidin-4-yl)oxy)cyclohexyl)urea (Example 4).

$^1$H-NMR (400 MHz, CD$_3$OD) δ (ppm): 1.37-1.50 (2H, m), 1.50-1.60 (2H, m), 2.00-2.20 (4H, m), 3.40 (4H, t, J=8.0 Hz), 3.60-3.65 (1H, m), 3.78 (1H, t, J=8.0 Hz), 3.90 (3H, s), 4.40-4.50 (1H, m), 6.27 (1H, d, J=4.0 Hz), 6.39 (1H, dd, J=8.0, 4.0 Hz), 6.80 (1H, dd, J=8.0, 4.0 Hz), 6.96 (1H, d, J=8.0 Hz), 7.91 (1H, d, J=4.0 Hz), 8.10 (1H, s).

Example 49

Synthesis of 1-(2-methoxy-5-(trifluoromethoxy)phenyl)-3-(trans-4-(pyridin-4-yloxy)cyclohexyl)urea

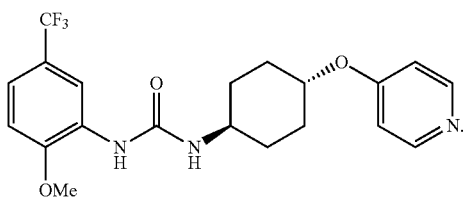 [SMILES: COc1ccc(C(F)(F)F)cc1NC(=O)N[C@H]1CC[C@H](Oc2ccncc2)CC1]

The title compound (0.041 g) (hereinafter referred to as the compound of Example 49) was obtained using 2,2,2-trichloroethyl (2-methoxy-5-(trifluoromethoxy)phenyl)carbamate (0.075 g, 0.20 mmol) and trans-4-(pyridin-4-yloxy)cyclohexanamine dihydrochloride (0.025 g, 0.13 mmol) by a method similar to that for the synthesis of 1-(2-methoxy-5-(pentafluorosulfanyl)phenyl)-3-(trans-4-((2-morpholinopyrimidin-4-yl)oxy)cyclohexyl)urea (Example 4).

$^1$H-NMR (400 MHz, CD$_3$OD) δ (ppm): 1.40-1.50 (2H, m), 1.60-1.70 (2H, m), 2.00-2.20 (4H, m), 3.60-3.65 (1H, m), 3.90 (3H, s), 4.40-4.60 (1H, m), 6.80 (1H, dd, J=9.0, 4.0 Hz), 6.91-7.00 (3H, m), 8.09 (1H, dd, J=8.0, 4.0 Hz), 8.30 (1H, d, J=4.0 Hz).

Example 50

Synthesis of 1-(3-(hydroxymethyl)-2-methoxy-5-(trifluoromethoxy)phenyl)-3-(trans-4-((2-morpholinopyrimidin-4-yl)oxy)cyclohexyl)urea

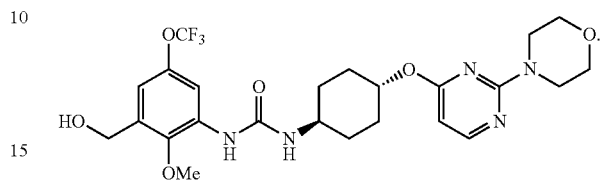

The title compound (0.022 g) (hereinafter referred to as the compound of Example 50) was obtained using 2,2,2-trichloroethyl (3-(hydroxymethyl)-2-methoxy-5-(trifluoromethoxy)phenyl)carbamate (0.046 g, 0.11 mmol) by a method similar to that for the synthesis of 1-(2-methoxy-5-(pentafluorosulfanyl)phenyl)-3-(trans-4-((2-morpholinopyrimidin-4-yl)oxy)cyclohexyl)urea (Example 4).

$^1$H-NMR (400 MHz, CDCl$_3$) δ (ppm): 1.25-1.41 (2H, m), 1.62-1.65 (2H, m), 1.92 (1H, brs), 2.16-2.19 (4H, m), 3.74-3.76 (9H, m), 3.80 (3H, s), 4.61 (1H, d, J=8.3 Hz), 4.73 (2H, d, J=4.9 Hz), 4.96 (1H, brs), 5.98 (1H, d, J=5.6 Hz), 6.74 (1H, s), 6.93 (1H, d, J=2.4 Hz), 8.01 (1H, d, J=2.2 Hz), 8.06 (1H, d, J=5.6 Hz).

MS(ESI) [M+H]$^+$: 542.

Example 51

Synthesis of 1-(3-(hydroxymethyl)-5-(trifluoromethyl)phenyl)-3-(trans-4-((2-morpholinopyrimidin-4-yl)oxy)cyclohexyl)urea

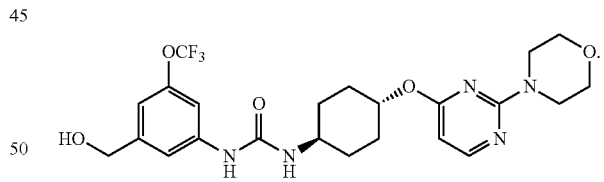

The title compound (0.039 g) (hereinafter referred to as the compound of Example 51) was obtained using 2,2,2-trichloroethyl (3-(hydroxymethyl)-5-(trifluoromethoxy)phenyl)carbamate (0.030 g, 0.082 mmol) by a method similar to that for the synthesis of 1-(2-methoxy-5-(pentafluorosulfanyl)phenyl)-3-(trans-4-((2-morpholinopyrimidin-4-yl)oxy)cyclohexyl)urea (Example 4).

$^1$H-NMR (400 MHz, CD$_3$OD) δ (ppm): 1.25-1.41 (2H, m), 1.62-1.65 (2H, m), 1.92 (1H, s), 1.20-1.30 (2H, m), 1.40-1.50 (2H, m), 2.00-2.20 (4H, m), 3.40-3.50 (1H, m), 3.55-3.65 (1H, m), 4.61 (2H, s), 4.64 (2H, s), 7.23 (1H, s), 7.43 (2H, d, J=8.0 Hz), 7.47 (1H, s), 7.73 (1H, s), 8.47 (1H, d, J=8.0, 4.0 Hz).

Example 52

Synthesis of 1-(3-(morpholinomethyl)-5-(trifluoromethyl)phenyl)-3-(trans-4-((2-morpholinopyrimidin-4-yl)oxy)cyclohexyl)urea

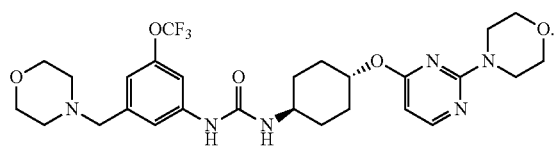 [SMILES: O=C(Nc1cc(CN2CCOCC2)cc(OC(F)(F)F)c1)N[C@H]1CC[C@H](Oc2ccnc(N3CCOCC3)n2)CC1]

To a solution of 1-(3-(hydroxymethyl)-5-(trifluoromethyl)phenyl)-3-(trans-4-((2-morpholinopyrimidin-4-yl)oxy)cyclohexyl)urea (0.032 g, 0.065 mmol) and diisopropylethylamine (0.017 g, 0.136 mmol) in DMF, methanesulfonyl chloride (0.011 g, 0.097 mmol) was added and stirred for one hour under cooling on ice. Morpholine (0.017 g, 0.2 mmol) was added thereto, and the obtained solution was stirred overnight at room temperature. A saturated aqueous solution of ammonium chloride was added to the reaction solution to stop the reaction, and the obtained solution was subsequently extracted with ethyl acetate, and the organic layer was washed with a saturated aqueous solution of sodium chloride. The obtained organic layer was dried over anhydrous sodium sulfate and then concentrated under vacuum, and the obtained crude product was purified by amino-silica gel column chromatography (eluent; chloroform:methanol=99:1→96:4) to obtain the title compound (0.024 g) (hereinafter referred to as the compound of Example 52).

$^1$H-NMR (400 MHz, DMSO-d$_6$) δ (ppm): 1.36-1.51 (4H, m), 1.91-2.06 (4H, m), 2.36 (s, 4H), 3.48 (s, 2H), 3.58 (4H, t, J=4.0 Hz), 3.66 (s, 8H), 6.07 (1H, d, J=4.0 Hz), 6.20 (1H, d, J=8.0 Hz), 7.14 (1H, s), 7.44 (1H, s), 7.87 (1H, s), 8.09 (1H, d, J=8.0 Hz), 8.80 (s, 1H).

Example 53

Synthesis of 1-(4-(hydroxymethyl)-3-(trifluoromethyl)phenyl)-3-(trans-4-((2-morpholinopyrimidin-4-yl)oxy)cyclohexyl)urea

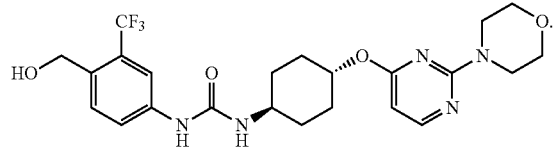 [SMILES: O=C(Nc1ccc(CO)c(C(F)(F)F)c1)N[C@H]1CC[C@H](Oc2ccnc(N3CCOCC3)n2)CC1]

The title compound (0.021 g) (hereinafter referred to as the compound of Example 53) was obtained using 2,2,2-trichloroethyl (4-(hydroxymethyl)-3-(trifluoromethoxy)phenyl)carbamate (0.030 g, 0.082 mmol) by a method similar to that for the synthesis of 1-(2-methoxy-5-(pentafluorosulfanyl)phenyl)-3-(trans-4-((2-morpholinopyrimidin-4-yl)oxy)cyclohexyl)urea (Example 4).

$^1$H-NMR (400 MHz, DMSO-d$_6$) δ (ppm): 1.31-1.53 (4H, m), 1.92-2.08 (4H, m), 3.65 (s, 8H), 4.56 (2H, d, J=8.0 Hz), 5.31 (1H, t, J=8.0 Hz), 6.05 (1H, d, J=4.0 Hz), 6.16 (1H, d, J=4.0 Hz), 7.48 (1H, d, J=8.0 Hz), 7.57 (1H, d, J=8.0 Hz), 7.91 (1H, s), 8.01 (1H, d, J=8.0 Hz), 8.67 (1H, s).

Example 54

Synthesis of 1-(2-methoxy-5-(trifluoromethoxy)phenyl)-3-(trans-4-((4-(methylamino)pyrimidin-2-yl)oxy)cyclohexyl)urea

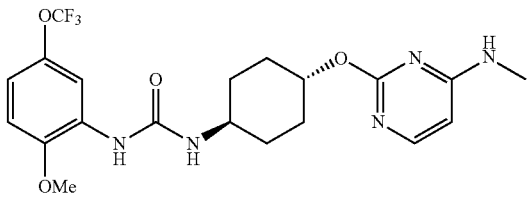

The title compound (0.023 g) (hereinafter referred to as the compound of Example 54) was obtained using 2,2,2-trichloroethyl (2-methoxy-5-(trifluoromethoxy)phenyl)carbamate (0.038 g, 0.099 mmol) and 2-((trans-4-aminocyclohexyl)oxy)-N-methylpyrimidin-4-amine dihydrochloride (0.017 g, 0.066 mmol) by a method similar to that for the synthesis of 1-(2-methoxy-5-(pentafluorosulfanyl)phenyl)-3-(trans-4-((2-morpholinopyrimidin-4-yl)oxy)cyclohexyl)urea (Example 4).

$^1$H-NMR (400 MHz, CDCl$_3$) δ (ppm): 1.23-1.38 (2H, m), 1.65-1.70 (2H, m), 2.17 (4H, t, J=14.8 Hz), 2.94 (3H, d, J=5.1 Hz), 3.49 (1H, d, J=3.7 Hz), 3.73-3.74 (1H, m), 3.87 (3H, s), 4.49 (1H, d, J=7.6 Hz), 4.89 (1H, brs), 5.98 (1H, d, J=5.6 Hz), 6.78-6.80 (2H, m), 6.82 (1H, s), 7.96 (1H, s), 8.15 (1H, s).

MS(ESI) [M+H]$^+$: 456.

Example 55

Synthesis of 1-(2-methoxy-5-(trifluoromethoxy)phenyl)-3-(trans-4-((2-morpholinopyrimidin-4-yl)oxy)cyclohexyl)urea

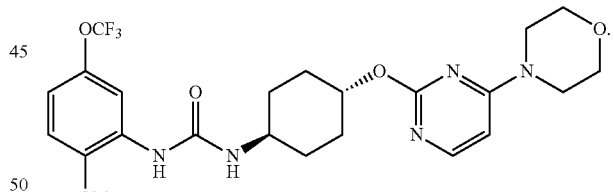

The title compound (0.027 g) (hereinafter referred to as the compound of Example 55) was obtained using 2,2,2-trichloroethyl (2-methoxy-5-(trifluoromethoxy)phenyl)carbamate (0.038 g, 0.099 mmol) and trans-4-((4-morpholinopyrimidin-2-yl)oxy)cyclohexanamine dihydrochloride (0.021 g, 0.066 mmol) by a method similar to that for the synthesis of 1-(2-methoxy-5-(pentafluorosulfanyl)phenyl)-3-(trans-4-((2-morpholinopyrimidin-4-yl)oxy)cyclohexyl)urea (Example 4).

$^1$H-NMR (400 MHz, CDCl$_3$) δ (ppm): 1.28-1.35 (2H, m), 1.67-1.72 (2H, m), 2.15-2.18 (4H, m), 3.60-3.61 (4H, m), 3.75-3.76 (5H, m), 4.62 (1H, d, J=7.6 Hz), 4.88-4.90 (1H, m), 6.14 (1H, d, J=6.1 Hz), 6.77-6.80 (2H, m), 6.88 (1H, s), 8.02 (1H, d, J=6.1 Hz), 8.14 (1H, d, J=0.7 Hz).

MS(ESI) [M+H]$^+$: 512.

Example 56

Synthesis of 1-(2-(oxetan-3-yloxy)-5-(trifluoromethyl)phenyl)-3-(trans-4-(pyridin-4-ylmethoxy)cyclohexyl)urea

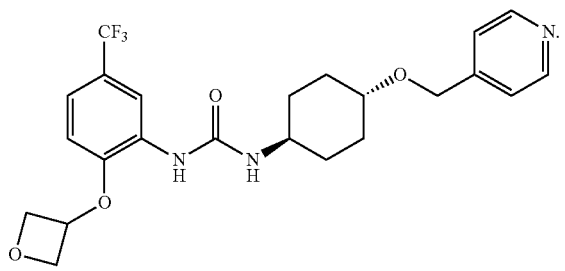 [SMILES: O=C(Nc1cc(C(F)(F)F)ccc1OC1COC1)N[C@H]1CC[C@H](OCc2ccncc2)CC1]

The title compound (0.013 g) (hereinafter referred to as the compound of Example 56) was obtained using 2,2,2-trichloroethyl (2-(oxetan-3-yloxy)-5-(trifluoromethyl)phenyl)carbamate (0.040 g, 0.098 mmol) and trans-4-(pyridin-4-ylmethoxy)cyclohexanamine dihydrochloride (0.020 g, 0.098 mmol) by a method similar to that for the synthesis of 1-(2-methoxy-5-(pentafluorosulfanyl)phenyl)-3-(trans-4-((2-morpholinopyrimidin-4-yl)oxy)cyclohexyl)urea (Example 4).

$^1$H-NMR (400 MHz, CD$_3$OD) δ (ppm): 1.25-1.38 (2H, m), 1.40-1.53 (2H, m), 2.00-2.15 (4H, m), 3.41-3.49 (1H, m), 3.57-3.64 (1H, m), 4.61 (2H, s), 4.75-4.82 (2H, m), 5.03-5.07 (2H, t, J=8.0 Hz), 5.37-5.42 (1H, m), 6.70 (1H, d, J=8.0 Hz), 7.16 (1H, dd, J=8.0, 4.0 Hz), 7.42 (1H, d, J=8.0 Hz), 8.46-8.50 (3H, m).

Example 57

Synthesis of 1-(2-morpholino-5-(trifluoromethyl)phenyl)-3-(trans-4-(pyrimidin-2-yloxy)cyclohexyl)urea

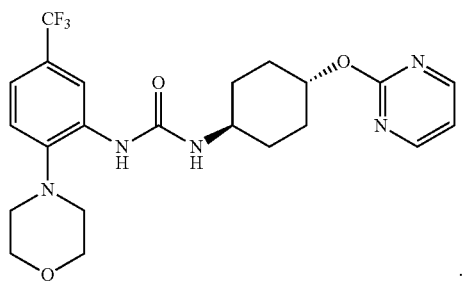 [SMILES: O=C(Nc1cc(C(F)(F)F)ccc1N1CCOCC1)N[C@H]1CC[C@H](Oc2ncccn2)CC1]

The title compound (0.021 g) (hereinafter referred to as the compound of Example 57) was obtained using 2,2,2-trichloroethyl (2-morpholino-5-(trifluoromethyl)phenyl)carbamate (0.042 g, 0.10 mmol) and trans-4-(pyrimidin-2-yloxy)cyclohexanamine (0.019 g, 0.10 mmol) by a method similar to that for the synthesis of 1-(2-methoxy-5-(pentafluorosulfanyl)phenyl)-3-(trans-4-((2-morpholinopyrimidin-4-yl)oxy)cyclohexyl)urea (Example 4).

$^1$H-NMR (400 MHz, DMSO-d$_6$) δ (ppm): 1.29-1.41 (2H, m), 1.51-1.60 (2H, m), 1.96-2.14 (4H, m), 2.80-2.83 (4H, m), 3.50-3.60 (1H, m), 3.79-3.87 (4H, m), 4.91-4.99 (1H, m), 7.11 (1H, t, J=8.0 Hz), 7.23-7.25 (1H, m), 7.30-7.32 (2H, m), 7.90 (1H, s), 8.51 (1H, d, J=4.0 Hz), 8.59 (1H, s), 8.61 (1H, s).

Example 58

Synthesis of 1-(2-chloro-5-(trifluoromethyl)phenyl)-3-(trans-4-(pyrimidin-2-yloxy)cyclohexyl)urea

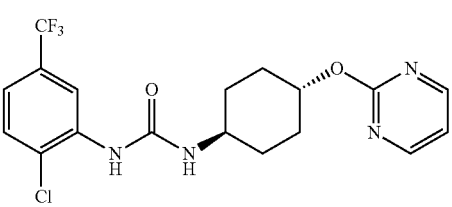

The title compound (0.02 g) (hereinafter referred to as the compound of Example 58) was obtained using 2,2,2-trichloroethyl (2-chloro-5-(trifluoromethyl)phenyl)carbamate (0.030 g, 0.081 mmol) and trans-4-(pyrimidin-2-yloxy)cyclohexanamine (0.016 g, 0.081 mmol) by a method similar to that for the synthesis of 1-(2-methoxy-5-(pentafluorosulfanyl)phenyl)-3-(trans-4-((2-morpholinopyrimidin-4-yl)oxy)cyclohexyl)urea (Example 4).

$^1$H-NMR (400 MHz, CD$_3$OD) δ (ppm): 1.32-1.41 (2H, m), 1.52-1.62 (2H, m), 1.97-2.12 (4H, m), 3.50-3.60 (1H, m), 4.91-4.99 (1H, m), 7.11 (1H, t, J=8.0 Hz), 7.24-7.29 (2H, m), 7.65 (1H, d, J=8.0 Hz), 8.30 (1H, s), 8.60 (2H, d, J=4.0 Hz), 8.67 (1H, d, J=4.0 Hz).

Example 59

Synthesis of 1-(2-methoxy-5-(trifluoromethoxy)phenyl)-3-(trans-4-((6-morpholinopyrimidin-4-yl)oxy)cyclohexyl)urea

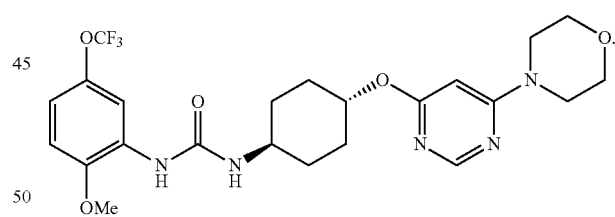

The title compound (0.019 g) (hereinafter referred to as the compound of Example 59) was obtained using 2,2,2-trichloroethyl (2-methoxy-5-(trifluoromethoxy)phenyl)carbamate (0.037 g, 0.095 mmol) and trans-4-((6-morpholinopyrimidin-4-yl)oxy)cyclohexanamine dihydrochloride (0.020 g, 0.064 mmol) by a method similar to that for the synthesis of 1-(2-methoxy-5-(pentafluorosulfanyl)phenyl)-3-(trans-4-((2-morpholinopyrimidin-4-yl)oxy)cyclohexyl)urea (Example 4).

$^1$H-NMR (400 MHz, CDCl$_3$) δ (ppm): 1.34-1.37 (2H, m), 1.55-1.61 (2H, m), 2.13-2.16 (4H, m), 3.54-3.55 (4H, m), 3.76-3.77 (5H, m), 3.87 (3H, s), 4.47 (1H, d, J=7.1 Hz), 5.02 (1H, brs), 5.78 (1H, s), 6.79-6.81 (3H, m), 8.15 (1H, s), 8.30 (1H, s).

MS(ESI) [M+H]$^+$: 512.

Example 60

Synthesis of 1-(2-methoxy-5-(trifluoromethoxy)phenyl)-3-(trans-4-((6-(methylamino)pyrimidin-2-yl)oxy)cyclohexyl)urea

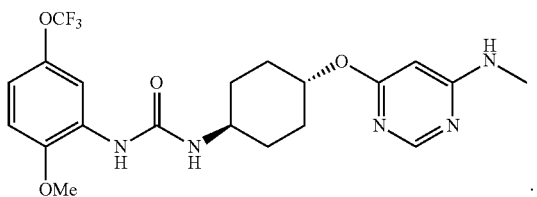

The title compound (0.035 g) (hereinafter referred to as the compound of Example 60) was obtained using 2,2,2-trichloroethyl (2-methoxy-5-(trifluoromethoxy)phenyl)carbamate (0.067 g, 0.17 mmol) and 2-((trans-6-aminocyclohexyl)oxy)-N-methylpyrimidin-4-amine dihydrochloride (0.030 g, 0.12 mmol) by a method similar to that for the synthesis of 1-(2-methoxy-5-(pentafluorosulfanyl)phenyl)-3-(trans-4-((2-morpholinopyrimidin-4-yl)oxy)cyclohexyl)urea (Example 4).

$^1$H-NMR (400 MHz, CDCl$_3$) δ (ppm): 1.36-1.38 (2H, m), 1.55-1.58 (2H, m), 2.13-2.17 (4H, m), 2.87 (3H, d, J=5.1 Hz), 3.76 (1H, brs), 3.87 (3H, s), 4.47 (1H, s), 4.85 (1H, brs), 5.01 (1H, s), 5.62 (1H, s), 6.79-6.81 (3H, m), 8.15 (1H, s), 8.21 (1H, s).

MS(ESI) [M+H]$^+$: 456.

Example 61

Synthesis of 1-(trans-4-((2-((2-hydroxyethyl)amino)pyrimidin-4-yl)oxy)cyclohexyl)-3-(3-(hydroxymethyl)-2-methoxy-5-(trifluoromethyl)phenyl)urea

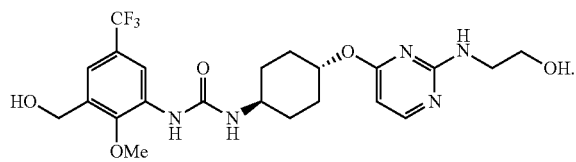 [SMILES: COc1c(CO)cc(C(F)(F)F)cc1NC(=O)N[C@H]1CC[C@H](Oc2ccnc(NCCO)n2)CC1]

The title compound (0.0079 g) (hereinafter referred to as the compound of Example 61) was obtained using 2,2,2-trichloroethyl (3-(hydroxymethyl)-2-methoxy-5-(trifluoromethyl)phenyl)carbamate (0.030 g, 0.076 mmol) and 2-((4-((trans-4-aminocyclohexyl)oxy)pyrimidin-2-yl)amino)ethanol dihydrochloride (0.020 g, 0.069 mmol) by a method similar to that for the synthesis of 1-(2-methoxy-5-(pentafluorosulfanyl)phenyl)-3-(trans-4-((2-morpholinopyrimidin-4-yl)oxy)cyclohexyl)urea (Example 4).

$^1$H-NMR (400 MHz, CD$_3$OD) δ (ppm): 1.38-1.44 (2H, m), 1.57-1.63 (2H, m), 2.09-2.15 (4H, m), 3.47 (2H, t, J=5.9 Hz), 3.62-3.71 (3H, m), 3.80 (3H, s), 4.70 (2H, s), 5.03-5.08 (1H, m), 5.99 (1H, d, J=5.9 Hz), 7.36 (1H, d, J=1.5 Hz), 7.91 (1H, d, J=5.6 Hz), 8.41 (1H, d, J=2.2 Hz).

MS(ESI) [M+H]$^+$: 500.

Example 62

Synthesis of 1-(trans-4-((2-((2-hydroxyethyl)amino)pyrimidin-4-yl)oxy)cyclohexyl)-3-(2-methoxy-5-(trifluoromethoxy)phenyl)urea

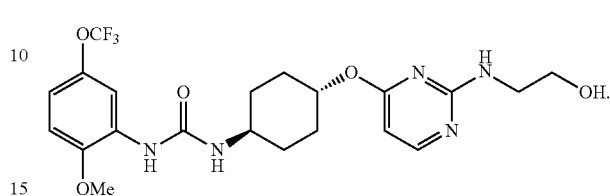

The title compound (0.013 g) (hereinafter referred to as the compound of Example 62) was obtained using 2,2,2-trichloroethyl (2-methoxy-5-(trifluoromethoxy)phenyl)carbamate (0.029 g, 0.076 mmol) and 2-((4-((trans-4-aminocyclohexyl)oxy)pyrimidin-2-yl)amino)ethanol dihydrochloride (0.020 g, 0.069 mmol) by a method similar to that for the synthesis of 1-(2-methoxy-5-(pentafluorosulfanyl)phenyl)-3-(trans-4-((2-morpholinopyrimidin-4-yl)oxy)cyclohexyl)urea (Example 4).

$^1$H-NMR (400 MHz, CDCl$_3$) δ (ppm): 1.30-1.35 (2H, m), 1.59-1.62 (2H, m), 2.13-2.15 (4H, m), 3.55-3.57 (2H, m), 3.74-3.76 (1H, m), 3.82-3.83 (2H, m), 3.87 (3H, s), 4.52-4.54 (1H, m), 4.91-4.94 (1H, m), 5.34 (1H, s), 6.01 (1H, d, J=5.9 Hz), 6.78-6.82 (2H, m), 6.83 (1H, s), 7.97 (1H, d, J=5.9 Hz), 8.14 (1H, s).

MS(ESI) [M+H]$^+$: 486.

Example 63

Synthesis of 1-(trans-4-((2-((2-hydroxyethyl)amino)pyrimidin-4-yl)oxy)cyclohexyl)-3-(2-(oxetan-3-yloxy)-5-(trifluoromethyl)phenyl)urea

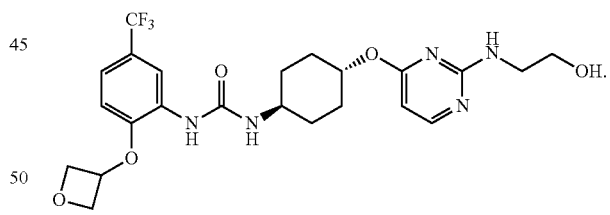

The title compound (0.018 g) (hereinafter referred to as the compound of Example 63) was obtained using 2,2,2-trichloroethyl (2-(oxetan-3-yloxy)-5-(trifluoromethyl)phenyl)carbamate (0.031 g, 0.076 mmol) and 2-((4-((trans-4-aminocyclohexyl)oxy)pyrimidin-2-yl)amino)ethanol dihydrochloride (0.020 g, 0.069 mmol) by a method similar to that for the synthesis of 1-(2-methoxy-5-(pentafluorosulfanyl)phenyl)-3-(trans-4-((2-morpholinopyrimidin-4-yl)oxy)cyclohexyl)urea (Example 4).

$^1$H-NMR (400 MHz, CDCl$_3$) δ (ppm): 1.32-1.55 (4H, m), 2.12 (4H, d, J=8.5 Hz), 3.57 (2H, dd, J=10.0, 5.4 Hz), 3.71-3.75 (1H, m), 3.84 (2H, t, J=4.8 Hz), 4.78 (2H, dd, J=7.6, 4.9 Hz), 4.90-4.94 (1H, m), 5.03 (2H, t, J=6.7 Hz), 5.28 (1H, dd, J=10.6, 4.8 Hz), 5.45-5.49 (1H, m), 6.01 (1H, d, J=5.9 Hz), 6.43 (1H, d, J=8.5 Hz), 7.15 (2H, d, J=8.5 Hz), 7.97 (1H, d, J=5.9 Hz), 8.58 (1H, s).
MS(ESI) [M+H]⁺: 512.

Example 64

Synthesis of 1-(trans-4-((2-(methylamino)pyrimidin-4-yl)oxy)cyclohexyl)-3-(2-(oxetan-3-yloxy)-5-(trifluoromethyl)phenyl)urea

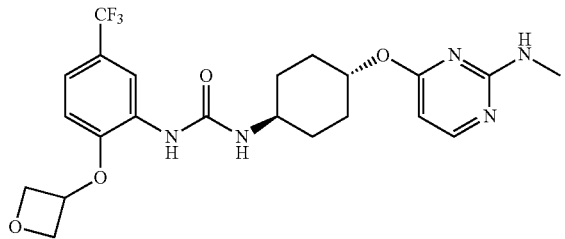 [SMILES: CNc1nccc(O[C@H]2CC[C@H](NC(=O)Nc3cc(C(F)(F)F)ccc3OC3COC3)CC2)n1]

The title compound (0.028 g) (hereinafter referred to as the compound of Example 64) was obtained using 2,2,2-trichloroethyl (2-(oxetan-3-yloxy)-5-(trifluoromethyl)phenyl)carbamate (0.038 g, 0.077 mmol) and 4-((trans-4-aminocyclohexyl)oxy)-N-methylpyrimidin-2-amine dihydrochloride (0.017 g, 0.066 mmol) by a method similar to that for the synthesis of 1-(2-methoxy-5-(pentafluorosulfanyl)phenyl)-3-(trans-4-((2-morpholinopyrimidin-4-yl)oxy)cyclohexyl)urea (Example 4).
¹H-NMR (400 MHz, CD₃OD) δ (ppm): 1.41-1.44 (2H, m), 1.58-1.60 (2H, m), 2.10-2.17 (4H, m), 2.88 (3H, s), 3.61-3.70 (1H, m), 4.74-4.77 (2H, m), 5.02-5.06 (3H, m), 5.38-5.42 (1H, m), 5.97 (1H, d, J=6.1 Hz), 6.68 (1H, d, J=8.0 Hz), 7.17 (1H, d, J=9.8 Hz), 7.91 (1H, d, J=5.4 Hz), 8.49 (1H, s).
MS(ESI) [M+H]⁺: 482.

Example 65

Synthesis of 1-(3-(hydroxymethyl)-2-methoxy-5-(trifluoromethyl)phenyl)-3-(trans-4-((2-(methylamino)pyrimidin-4-yl)oxy)cyclohexyl)urea

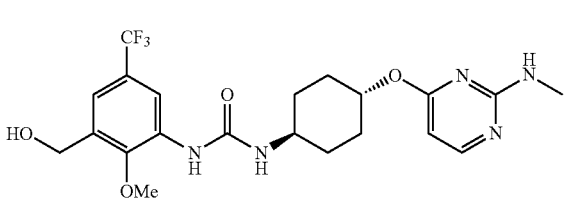

The title compound (0.029 g) (hereinafter referred to as the compound of Example 65) was obtained using 2,2,2-trichloroethyl (3-(hydroxymethyl)-2-methoxy-5-(trifluoromethyl)phenyl)carbamate (0.031 g, 0.077 mmol) and 4-((trans-4-aminocyclohexyl)oxy)-N-methylpyrimidin-2-amine dihydrochloride (0.017 g, 0.066 mmol) by a method similar to that for the synthesis of 1-(2-methoxy-5-(pentafluorosulfanyl)phenyl)-3-(trans-4-((2-morpholinopyrimidin-4-yl)oxy)cyclohexyl)urea (Example 4).
¹H-NMR (400 MHz, CD₃OD) δ (ppm): 1.41 (2H, t, J=11.6 Hz), 1.59 (2H, t, J=10.9 Hz), 2.09-2.16 (4H, m), 2.88 (3H, s), 3.61-3.65 (1H, m), 3.80 (3H, s), 4.70 (2H, s), 5.07 (1H, d, J=4.4 Hz), 5.97 (1H, d, J=5.9 Hz), 7.36 (1H, s), 7.91 (1H, d, J=5.9 Hz), 8.41 (1H, d, J=1.7 Hz).

Example 66

Synthesis of 1-(2-(oxetan-3-yloxy)-5-(trifluoromethyl)phenyl)-3-(trans-4-(pyrimidin-4-yloxy)cyclohexyl)urea

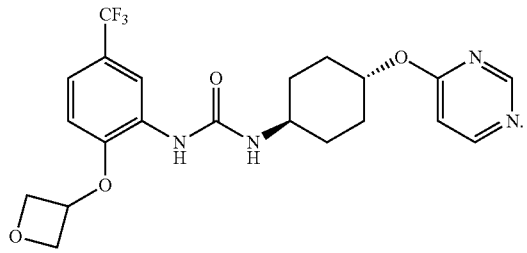 [SMILES: O=C(Nc1cc(C(F)(F)F)ccc1OC1COC1)N[C@H]1CC[C@H](Oc2ccncn2)CC1]

The title compound (0.029 g) (hereinafter referred to as the compound of Example 66) was obtained using 2,2,2-trichloroethyl (2-(oxetan-3-yloxy)-5-(trifluoromethyl)phenyl)carbamate and trans-4-(pyrimidin-4-yloxy)cyclohexanamine by a method similar to that for the synthesis of 1-(2-methoxy-5-(pentafluorosulfanyl)phenyl)-3-(trans-4-((2-morpholinopyrimidin-4-yl)oxy)cyclohexyl)urea (Example 4).
¹H-NMR (400 MHz, CD₃OD) δ (ppm): 1.29-1.38 (2H, m), 1.52-1.69 (2H, m), 2.01-2.20 (4H, m), 3.60-3.68 (1H, m), 4.77-4.80 (2H, m), 5.01-5.08 (2H, m), 5.10-5.21 (1H, m), 5.38-5.43 (1H, m), 6.67-6.73 (1H, m), 6.84 (1H, d, J=8.0 Hz), 7.16-7.25 (1H, m), 8.41 (1H, d, J=8.0 Hz), 8.49 (1H, d, J=4.0 Hz), 8.70 (1H, s).

Example 67

Synthesis of 1-(3-(hydroxymethyl)-2-methoxy-5-(trifluoromethoxy)phenyl)-3-(trans-4-(pyridin-3-ylmethoxy)cyclohexyl)urea

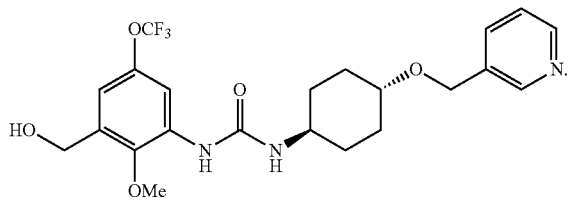 [SMILES: COc1c(CO)cc(OC(F)(F)F)cc1NC(=O)N[C@H]1CC[C@H](OCc2cccnc2)CC1]

The title compound (0.029 g) (hereinafter referred to as the compound of Example 67) was obtained using 2,2,2-trichloroethyl (3-(hydroxymethyl)-2-methoxy-5-(trifluoromethoxy)phenyl)carbamate (0.033 g, 0.079 mmol) and trans-4-(pyridin-3-ylmethoxy)cyclohexanamine dihydrochloride (0.020 g, 0.070 mmol) by a method similar to that for the synthesis of 1-(2-methoxy-5-(pentafluorosulfanyl)phenyl)-3-(trans-4-((2-morpholinopyrimidin-4-yl)oxy)cyclohexyl)urea (Example 4).
¹H-NMR (400 MHz, CDCl₃) δ (ppm): 1.20-1.28 (2H, m), 1.48-1.52 (2H, m), 2.00-2.02 (1H, m), 2.10-2.12 (4H, m), 3.35 (1H, brs), 3.69 (1H, brs), 3.78 (3H, s), 4.57 (2H, s), 4.60

(1H, d, J=8.0 Hz), 4.72 (2H, d, J=6.1 Hz), 6.74 (1H, s), 6.92 (1H, d, J=1.7 Hz), 7.28-7.30 (2H, m), 7.69 (1H, d, J=7.3 Hz), 8.03 (1H, d, J=2.4 Hz), 8.54 (1H, dd, J=4.9, 1.7 Hz), 8.56 (1H, d, J=1.5 Hz).

Example 68

Synthesis of 1-(2-methoxy-5-(trifluoromethoxy)phenyl)-3-(trans-4-(pyridin-3-ylmethoxy)cyclohexyl)urea

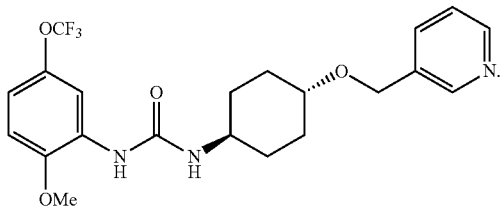 [SMILES: COc1ccc(OC(F)(F)F)cc1NC(=O)N[C@H]1CC[C@H](OCc2cccnc2)CC1]

The title compound (0.022 g) (hereinafter referred to as the compound of Example 68) was obtained using 2,2,2-trichloroethyl (2-methoxy-5-(trifluoromethoxy)phenyl)carbamate (0.030 g, 0.079 mmol) and trans-4-(pyridin-3-ylmethoxy)cyclohexanamine dihydrochloride (0.020 g, 0.079 mmol) by a method similar to that for the synthesis of 1-(2-methoxy-5-(pentafluorosulfanyl)phenyl)-3-(trans-4-((2-morpholinopyrimidin-4-yl)oxy)cyclohexyl)urea (Example 4).

$^1$H-NMR (400 MHz, CDCl$_3$) δ (ppm): 1.19-1.22 (2H, m), 1.47-1.50 (2H, m), 2.11 (4H, s), 3.36-3.38 (1H, m), 3.68-3.71 (1H, m), 3.86 (3H, s), 4.44 (1H, brs), 4.57 (2H, s), 6.78-6.80 (3H, m), 7.26-7.31 (1H, m), 7.70 (1H, d, J=7.8 Hz), 8.14 (1H, s), 8.54 (1H, dd, J=4.9, 1.5 Hz), 8.57 (1H, d, J=2.4 Hz).

Example 69

Synthesis of 1-(2-methoxy-5-(trifluoromethyl)phenyl)-3-(trans-4-(pyridin-3-ylmethoxy)cyclohexyl)urea

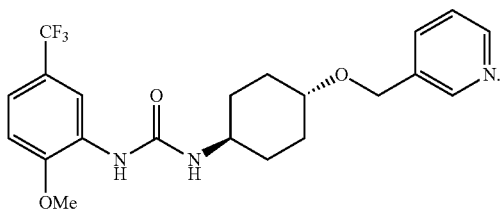 [SMILES: COc1ccc(C(F)(F)F)cc1NC(=O)N[C@H]1CC[C@H](OCc2cccnc2)CC1]

The title compound (0.021 g) (hereinafter referred to as the compound of Example 69) was obtained using 2,2,2-trichloroethyl (2-methoxy-5-(trifluoromethyl)phenyl)carbamate (0.029 g, 0.079 mmol) and trans-4-(pyridin-3-ylmethoxy)cyclohexanamine dihydrochloride (0.020 g, 0.079 mmol) by a method similar to that for the synthesis of 1-(2-methoxy-5-(pentafluorosulfanyl)phenyl)-3-(trans-4-((2-morpholinopyrimidin-4-yl)oxy)cyclohexyl)urea (Example 4).

$^1$H-NMR (400 MHz, CDCl$_3$) δ (ppm): 1.21-1.24 (2H, m), 1.47-1.50 (2H, m), 2.11-2.13 (4H, m), 3.36 (1H, brs), 3.71 (1H, brs), 3.91 (3H, s), 4.45 (1H, d, J=7.3 Hz), 4.57 (2H, s), 6.81 (1H, s), 6.88 (1H, d, J=8.8 Hz), 7.22-7.24 (1H, m), 7.27-7.31 (1H, m), 7.70 (1H, d, J=8.0 Hz), 8.49 (1H, s), 8.54 (1H, d, J=4.6 Hz), 8.58 (1H, s).

Example 70

Synthesis of 1-(3-(hydroxymethyl)-2-methoxy-5-(trifluoromethoxy)phenyl)-3-(trans-4-((6-(methylamino)pyrimidin-4-yl)oxy)cyclohexyl)urea

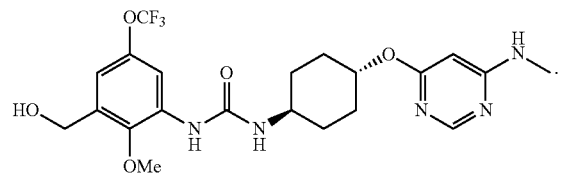 [SMILES: CNc1cc(O[C@H]2CC[C@H](NC(=O)Nc3cc(OC(F)(F)F)cc(CO)c3OC)CC2)ncn1]

The title compound (0.0083 g) (hereinafter referred to as the compound of Example 70) was obtained using 2,2,2-trichloroethyl (3-(hydroxymethyl)-2-methoxy-5-(trifluoromethoxy)phenyl)carbamate (0.026 g, 0.064 mmol) and 6-((trans-4-aminocyclohexyl)oxy)-N-methylpyrimidin-4-amine dihydrochloride (0.015 g, 0.058 mmol) by a method similar to that for the synthesis of 1-(2-methoxy-5-(pentafluorosulfanyl)phenyl)-3-(trans-4-((2-morpholinopyrimidin-4-yl)oxy)cyclohexyl)urea (Example 4).

$^1$H-NMR (400 MHz, CD$_3$OD) δ (ppm): 1.38-1.43 (2H, m), 1.56-1.62 (2H, m), 2.08-2.14 (4H, m), 2.84 (3H, s), 3.62-3.65 (1H, m), 3.75 (3H, s), 4.66 (2H, s), 4.86-4.89 (1H, m), 5.71 (1H, s), 6.95 (1H, s), 8.05 (1H, s), 8.08 (1H, s).

Example 71

Synthesis of 1-(3-(hydroxymethyl)-2-methoxy-5-(trifluoromethyl)phenyl)-3-(trans-4-((6-(methylamino)pyrimidin-4-yl)oxy)cyclohexyl)urea

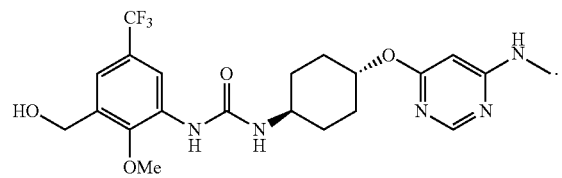 [SMILES: CNc1cc(O[C@H]2CC[C@H](NC(=O)Nc3cc(C(F)(F)F)cc(CO)c3OC)CC2)ncn1]

The title compound (0.0076 g) (hereinafter referred to as the compound of Example 71) was obtained using 2,2,2-trichloroethyl (3-(hydroxymethyl)-2-methoxy-5-(trifluoromethyl)phenyl)carbamate (0.025 g, 0.064 mmol) and 6-((trans-4-aminocyclohexyl)oxy)-N-methylpyrimidin-4-amine dihydrochloride (0.015 g, 0.058 mmol) by a method similar to that for the synthesis of 1-(2-methoxy-5-(pentafluorosulfanyl)phenyl)-3-(trans-4-((2-morpholinopyrimidin-4-yl)oxy)cyclohexyl)urea (Example 4).

$^1$H-NMR (400 MHz, CD$_3$OD) δ (ppm): 1.38-1.44 (3H, m), 1.57-1.62 (2H, m), 2.08-2.14 (4H, m), 2.84 (3H, s), 3.63-3.65 (1H, m), 3.80 (3H, s), 4.70 (2H, s), 4.84-4.86 (1H, m), 5.71 (1H, s), 7.36 (1H, s), 8.08 (1H, s), 8.41 (1H, d, J=1.7 Hz).

MS(ESI) [M+H]$^+$: 470.

Example 72

Synthesis of 1-(2-methoxy-5-(trifluoromethoxy)phenyl)-3-(trans-4-((pyridin-3-ylmethoxy)methyl)cyclohexyl)urea

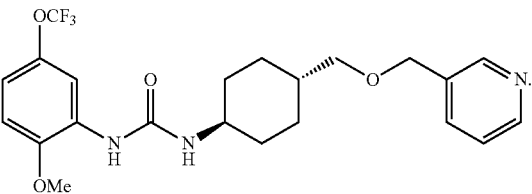 [SMILES: COc1ccc(OC(F)(F)F)cc1NC(=O)N[C@H]1CC[C@H](COCc2cccnc2)CC1]

The title compound (0.018 g) (hereinafter referred to as the compound of Example 72) was obtained using 2,2,2-trichloroethyl (2-methoxy-5-(trifluoromethoxy)phenyl)carbamate (0.029 g, 0.075 mmol) and trans-4-((pyridin-3-ylmethoxy)methyl)cyclohexanamine dihydrochloride (0.018 g, 0.068 mmol) by a method similar to that for the synthesis of 1-(2-methoxy-5-(pentafluorosulfanyl)phenyl)-3-(trans-4-((2-morpholinopyrimidin-4-yl)oxy)cyclohexyl)urea (Example 4).

$^1$H-NMR (400 MHz, CDCl$_3$) δ (ppm): 1.11-1.16 (4H, m), 1.55-1.57 (1H, m), 1.87-1.90 (2H, m), 2.08-2.10 (2H, m), 3.32 (2H, d, J=6.3 Hz), 3.63 (1H, brs), 3.86 (3H, s), 4.44 (1H, d, J=7.6 Hz), 4.51 (2H, s), 6.77-6.79 (3H, m), 7.27-7.30 (1H, m), 7.67 (1H, d, J=8.0 Hz), 8.14 (1H, s), 8.54 (1H, dd, J=4.8, 1.6 Hz), 8.57 (1H, d, J=1.5 Hz).

MS(ESI) [M+H]$^+$: 454.

Example 73

Synthesis of 1-(2-methoxy-5-(trifluoromethyl)phenyl)-3-(trans-4-((pyridin-3-ylmethoxy)methyl)cyclohexyl)urea

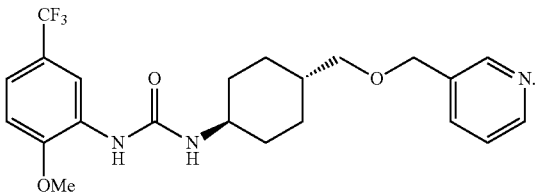 [SMILES: COc1ccc(C(F)(F)F)cc1NC(=O)N[C@H]1CC[C@H](COCc2cccnc2)CC1]

The title compound (0.014 g) (hereinafter referred to as the compound of Example 73) was obtained using 2,2,2-trichloroethyl (2-methoxy-5-(trifluoromethyl)phenyl)carbamate (0.028 g, 0.075 mmol) and trans-4-((pyridin-3-ylmethoxy)methyl)cyclohexanamine dihydrochloride (0.018 g, 0.068 mmol) by a method similar to that for the synthesis of 1-(2-methoxy-5-(pentafluorosulfanyl)phenyl)-3-(trans-4-((2-morpholinopyrimidin-4-yl)oxy)cyclohexyl)urea (Example 4).

$^1$H-NMR (400 MHz, CDCl$_3$) δ (ppm): 1.10-1.26 (4H, m), 1.55-1.57 (1H, m), 1.88-1.90 (2H, m), 2.05-2.10 (2H, m), 3.32 (2H, d, J=6.3 Hz), 3.62 (1H, brs), 3.91 (3H, s), 4.44 (1H, d, J=7.6 Hz), 4.51 (2H, s), 6.79 (1H, s), 6.88 (1H, d, J=8.5 Hz), 7.29-7.30 (2H, m), 7.67 (1H, d, J=7.8 Hz), 8.49 (1H, d, J=2.0 Hz), 8.54 (1H, dd, J=4.9, 1.7 Hz), 8.57 (1H, d, J=2.0 Hz).

Example 74

Synthesis of 1-(2-methoxy-5-(trifluoromethoxy)phenyl)-3-(trans-4-((pyridin-4-ylmethoxy)methyl)cyclohexyl)urea

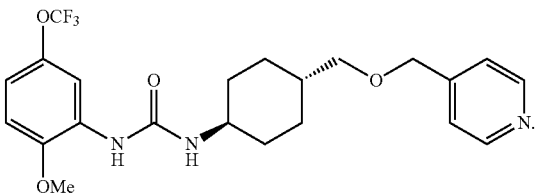 [SMILES: COc1ccc(OC(F)(F)F)cc1NC(=O)N[C@H]1CC[C@H](COCc2ccncc2)CC1]

The title compound (0.017 g) (hereinafter referred to as the compound of Example 74) was obtained using 2,2,2-trichloroethyl (2-methoxy-5-(trifluoromethoxy)phenyl)carbamate (0.029 g, 0.075 mmol) and trans-4-((pyridin-4-ylmethoxy)methyl)cyclohexanamine dihydrochloride (0.018 g, 0.068 mmol) by a method similar to that for the synthesis of 1-(2-methoxy-5-(pentafluorosulfanyl)phenyl)-3-(trans-4-((2-morpholinopyrimidin-4-yl)oxy)cyclohexyl)urea (Example 4).

$^1$H-NMR (400 MHz, CDCl$_3$) δ (ppm): 1.15-1.17 (2H, m), 1.55-1.57 (1H, m), 1.90-1.93 (2H, m), 2.10-2.12 (2H, m), 3.33 (2H, d, J=6.3 Hz), 3.65 (1H, brs), 3.87 (3H, s), 4.44 (1H, d, J=7.3 Hz), 4.51 (2H, s), 6.78-6.80 (3H, m), 7.25-7.26 (2H, m), 8.15 (1H, s), 8.57 (2H, d, J=5.9 Hz).

MS(ESI) [M+H]$^+$: 454.

Example 75

Synthesis of 1-(2-methoxy-5-(trifluoromethyl)phenyl)-3-(trans-4-((pyridin-4-ylmethoxy)methyl)cyclohexyl)urea

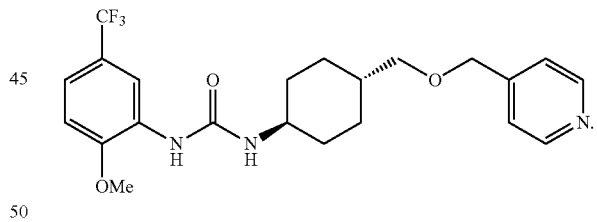

The title compound (0.013 g) (hereinafter referred to as the compound of Example 75) was obtained using 2,2,2-trichloroethyl (2-methoxy-5-(trifluoromethyl)phenyl)carbamate (0.029 g, 0.075 mmol) and trans-4-((pyridin-4-ylmethoxy)methyl)cyclohexanamine dihydrochloride (0.018 g, 0.068 mmol) by a method similar to that for the synthesis of 1-(2-methoxy-5-(pentafluorosulfanyl)phenyl)-3-(trans-4-((2-morpholinopyrimidin-4-yl)oxy)cyclohexyl)urea (Example 4).

$^1$H-NMR (400 MHz, CDCl$_3$) δ (ppm): 1.10-1.23 (4H, m), 1.55-1.57 (1H, m), 1.89-1.92 (2H, m), 2.10-2.13 (2H, m), 3.33 (2H, d, J=6.3 Hz), 3.65 (1H, brs), 3.91 (3H, s), 4.49-4.51 (3H, m), 6.81 (1H, s), 6.88 (1H, d, J=8.5 Hz), 7.22-7.24 (2H, m), 8.50 (1H, d, J=2.0 Hz), 8.57 (2H, t, J=2.9 Hz).

MS(ESI) [M+H]$^+$: 454.

Example 76

Synthesis of 1-(2-(oxetan-3-yloxy)-5-(trifluoromethyl)phenyl)-3-(trans-4-(pyridin-3-ylmethoxy)cyclohexyl)urea

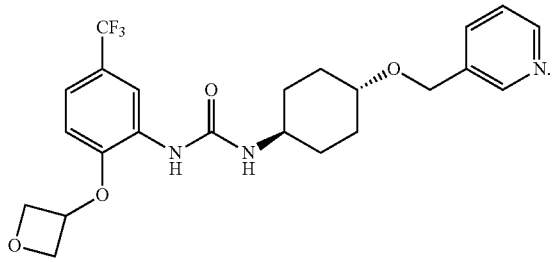 [SMILES: O=C(Nc1cc(C(F)(F)F)ccc1OC1COC1)N[C@H]1CC[C@H](OCc2cccnc2)CC1]

The title compound (0.011 g) (hereinafter referred to as the compound of Example 76) was obtained using 2,2,2-trichloroethyl (2-(oxetan-3-yloxy)-5-(trifluoromethyl)phenyl)carbamate (0.028 g, 0.069 mmol) and trans-4-(pyridin-3-ylmethoxy)cyclohexanamine dihydrochloride (0.018 g, 0.063 mmol) by a method similar to that for the synthesis of 1-(2-methoxy-5-(pentafluorosulfanyl)phenyl)-3-(trans-4-((2-morpholinopyrimidin-4-yl)oxy)cyclohexyl)urea (Example 4).

$^1$H-NMR (400 MHz, CDCl$_3$) δ (ppm): 1.19-1.28 (2H, m), 1.46-1.52 (2H, m), 2.11-2.14 (4H, m), 3.34-3.37 (1H, m), 3.69-3.71 (1H, m), 4.57 (2H, s), 4.73-4.78 (3H, m), 5.01 (2H, t, J=6.7 Hz), 5.25-5.28 (1H, m), 6.42 (1H, d, J=8.5 Hz), 6.89-6.91 (1H, m), 7.15-7.16 (1H, m), 7.29-7.31 (1H, m), 7.69-7.71 (1H, m), 8.53-8.58 (3H, m).

Example 77

Synthesis of 5-((trans-4-(3-(2-methoxy-5-(trifluoromethoxy)phenyl)ureido)cyclohexyl)methoxy)nicotinamide

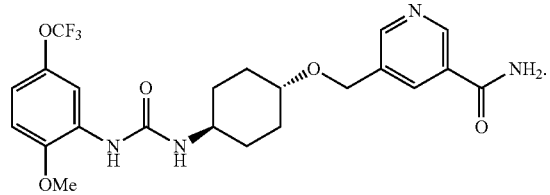 [SMILES: COc1ccc(OC(F)(F)F)cc1NC(=O)N[C@H]1CC[C@H](OCc2cncc(C(N)=O)c2)CC1]

The title compound (0.013 g) (hereinafter referred to as the compound of Example 77) was obtained using 2,2,2-trichloroethyl (2-methoxy-5-(trifluoromethoxy)phenyl)carbamate (0.023 g, 0.060 mmol) and 5-((trans-4-aminocyclohexyl)methoxy)nicotinamide dihydrochloride (0.016 g, 0.050 mmol) by a method similar to that for the synthesis of 1-(2-methoxy-5-(pentafluorosulfanyl)phenyl)-3-(trans-4-((2-morpholinopyrimidin-4-yl)oxy)cyclohexyl)urea (Example 4).

$^1$H-NMR (400 MHz, CD$_3$OD) δ (ppm): 1.24-1.30 (4H, m), 1.81-1.85 (1H, m), 1.93-1.98 (2H, m), 2.07-2.10 (2H, m), 3.52-3.55 (1H, m), 3.90 (3H, s), 3.96 (2H, d, J=6.1 Hz), 6.78-6.81 (1H, m), 6.96 (1H, d, J=9.0 Hz), 7.82 (1H, t, J=2.3 Hz), 8.09-8.09 (1H, m), 8.37 (1H, d, J=2.9 Hz), 8.60 (1H, d, J=1.7 Hz).

Example 78

Synthesis of 3-((trans-4-(3-(2-methoxy-5-(trifluoromethoxy)phenyl)ureido)cyclohexyl)methoxy)benzamide

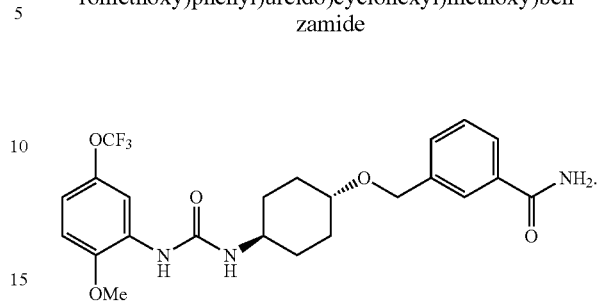

The title compound (0.016 g) (hereinafter referred to as the compound of Example 78) was obtained using 2,2,2-trichloroethyl (2-methoxy-5-(trifluoromethoxy)phenyl)carbamate (0.023 g, 0.060 mmol) and 3-((trans-4-aminocyclohexyl)methoxy)benzamide hydrochloride (0.016 g, 0.050 mmol) by a method similar to that for the synthesis of 1-(2-methoxy-5-(pentafluorosulfanyl)phenyl)-3-(trans-4-((2-morpholinopyrimidin-4-yl)oxy)cyclohexyl)urea (Example 4).

$^1$H-NMR (400 MHz, CD$_3$OD) δ (ppm): 1.20-1.32 (4H, m), 1.79-1.89 (1H, m), 2.00-2.04 (4H, m), 3.53 (1H, brs), 3.86 (2H, d, J=6.3 Hz), 3.90 (2H, brs), 6.80 (1H, dd, J=8.8, 2.0 Hz), 6.96 (1H, d, J=9.0 Hz), 7.08-7.10 (1H, m), 7.35 (1H, t, J=8.2 Hz), 7.41-7.43 (2H, m), 8.09 (1H, d, J=2.9 Hz).

MS(ESI) [M+H]$^+$: 482.

Example 79

Synthesis of 1-(3-(hydroxymethyl)-2-methoxy-5-(trifluoromethoxy)phenyl)-3-(trans-4-((2-(pyridin-3-yl)pyrimidin-4-yl)oxy)cyclohexyl)urea

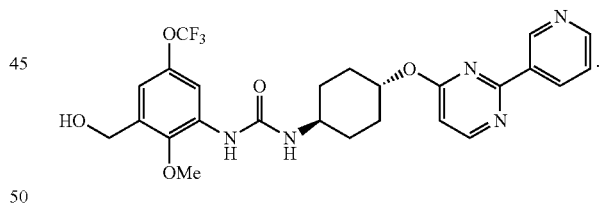

The title compound (0.015 g) (hereinafter referred to as the compound of Example 79) was obtained using 2,2,2-trichloroethyl (3-(hydroxymethyl)-2-methoxy-5-(trifluoromethoxy)phenyl)carbamate (0.020 g, 0.048 mmol) and trans-4-((2-(pyridin-3-yl)pyrimidin-4-yl)oxy)cyclohexanamine dihydrochloride (0.013 g, 0.048 mmol) by a method similar to that for the synthesis of 1-(2-methoxy-5-(pentafluorosulfanyl)phenyl)-3-(trans-4-((2-morpholinopyrimidin-4-yl)oxy)cyclohexyl)urea (Example 4).

$^1$H-NMR (400 MHz, DMSO-d$_6$) δ (ppm): 1.41-1.51 (2H, m), 1.57-1.67 (2H, m), 1.99-2.02 (2H, m), 2.17-2.20 (2H, m), 3.53-3.62 (1H, m), 3.69 (3H, s), 4.57 (2H, d, J=8.0 Hz), 5.24-5.38 (1H, m), 5.33 (1H, t, J=8.0 Hz), 6.90-6.96 (2H, m), 7.06 (1H, d, J=8.0 Hz), 7.57 (1H, q, J=4.0 Hz), 8.16 (1H, d, J=4.0 Hz), 8.24 (1H, s), 8.60-8.67 (2H, m), 8.73 (1H, dd, J=8.0, 4.0 Hz), 9.50 (1H, d, J=4.0 Hz).

Example 80

Synthesis of 1-(3-(hydroxymethyl)-2-methoxy-5-(trifluoromethoxy)phenyl)-3-(trans-4-((2-(methylamino)pyrimidin-4-yl)oxy)cyclohexyl)urea

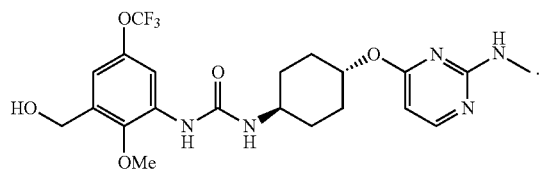 [SMILES: CNc1nccc(O[C@H]2CC[C@H](NC(=O)Nc3cc(OC(F)(F)F)cc(CO)c3OC)CC2)n1]

The title compound (0.019 g) (hereinafter referred to as the compound of Example 80) was obtained using 2,2,2-trichloroethyl (3-(hydroxymethyl)-2-methoxy-5-(trifluoromethoxy)phenyl)carbamate (0.020 g, 0.048 mmol) and 4-((trans-4-aminocyclohexyl)oxy)-N-methylpyrimidin-2-amine dihydrochloride (0.014 g, 0.048 mmol) by a method similar to that for the synthesis of 1-(2-methoxy-5-(pentafluorosulfanyl)phenyl)-3-(trans-4-((2-morpholinopyrimidin-4-yl)oxy)cyclohexyl)urea (Example 4).

$^1$H-NMR (400 MHz, CD$_3$OD) δ (ppm): 1.38-1.61 (4H, m), 2.08-2.16 (4H, m), 2.88 (3H, s), 3.63 (1H, brs), 3.75 (3H, s), 4.66 (2H, s), 5.07 (1H, brs), 5.97 (1H, d, J=5.9 Hz), 6.94 (1H, s), 7.91 (1H, d, J=5.9 Hz), 8.04 (1H, d, J=2.9 Hz).

Example 81

Evaluation of DDR1 Inhibition Activity:

The DDR1 inhibition activity in the compounds of Examples 1 to 80 was evaluated with HTRF® KinEASE-TK kit (Cisbio Bioassays).

Each test substance was dissolved in dimethyl sulfoxide and then used for the evaluation as described below. Moreover, each of test substances and reagents was diluted in the kinase buffer (Cisbio Bioassays) prepared by adding thereto MgCl$_2$, MnCl$_2$, DTT, and the Supplemental Enzyme buffer (Cisbio Bioassays) to concentrations of 5 mmol/L, 0.5 mmol/L, 0.25 mmol/L, and 50 nmol/L, respectively, and then used. Each test substance (in DMSO in a final concentration of 1%), the intracellular domain of DDR1 (in a final concentration of 5 ng/μL) (Carna Biosciences, Inc.), the phosphate donor ATP (in final concentration of 25 μm/L) (Sigma), and the substrate TK Substrate-biotin (in a final concentration of 1000 nmol/L) (Cisbio Bioassays) were added to a 384-well black plate (Corning) and allowed to react at room temperature for one hour. After completion of the reaction, the TK Antibody-Cryptate (Cisbio Bioassays) and the Streptavidin-XL665 (Cisbio Bioassays) were added thereto and allowed to react at room temperature for one hour. In addition, the plate was provided with a well to which a test substance was not added, and with a well to which a test substance and the intracellular domain of DDR1 were added.

The fluorescence intensity in each well was measured using a multi-label counter (Envision, PerkinElmer; excitation wavelength: 320 nm, measurement wavelength: 665 nm and 620 nm) to calculate a ratio (the fluorescence intensity at 665 nm/the fluorescence intensity at 620 nm). The inhibition rate (%) of a test substance at each concentration was calculated based on the formula below:

Inhibition rate (%)=([the ratio obtained from the well containing no test substance]−[the ratio from a well containing a test substance])/([the ratio obtained from the well containing no test substance]−[the ratio obtained from the well containing no intracellular domain of DDR1 and no test substance])×100.

The calculated inhibition rates were fitted to a sigmoidal dose-response curve by regression analysis using the Prism 5.04 (GraphPad Software, Inc.) to calculate the IC$_{50}$ value of the test substance.

The IC$_{50}$ value of each test substance is shown in Table 2. As seen from the results in Tables 2-1, 2-2 and 2-3, the urea derivatives (I) or the pharmaceutically acceptable salts thereof were indicated to have high DDR1 inhibition activity.

TABLE 2-1

| Test Substance | IC$_{50}$ (nmol/L) |
| --- | --- |
| Compound of Example 1 | 476 |
| Compound of Example 2 | 229 |
| Compound of Example 3 | 141 |
| Compound of Example 4 | 427 |
| Compound of Example 5 | 65.9 |
| Compound of Example 6 | 62.2 |
| Compound of Example 7 | 111 |
| Compound of Example 8 | 46.3 |
| Compound of Example 9 | 349 |
| Compound of Example 10 | 167 |
| Compound of Example 11 | 384 |
| Compound of Example 12 | 96.7 |
| Compound of Example 13 | 57.6 |
| Compound of Example 14 | 76.7 |
| Compound of Example 15 | 72.4 |
| Compound of Example 16 | 963 |
| Compound of Example 17 | 189 |
| Compound of Example 18 | 162 |
| Compound of Example 19 | 46.2 |
| Compound of Example 20 | 114 |
| Compound of Example 21 | 39.3 |
| Compound of Example 22 | 234 |
| Compound of Example 23 | 402 |
| Compound of Example 24 | 124 |
| Compound of Example 25 | 421 |
| Compound of Example 26 | 82.7 |
| Compound of Example 27 | 258 |
| Compound of Example 28 | 103 |
| Compound of Example 29 | 133 |
| Compound of Example 30 | 50.4 |
| Compound of Example 31 | 76.7 |
| Compound of Example 32 | 10 |
| Compound of Example 33 | 28 |
| Compound of Example 34 | 51 |
| Compound of Example 35 | 88.6 |
| Compound of Example 36 | 140 |
| Compound of Example 37 | 149 |

TABLE 2-2

| Test Substance | IC$_{50}$ (nmol/L) |
| --- | --- |
| Compound of Example 38 | 61 |
| Compound of Example 39 | 236 |
| Compound of Example 40 | 98 |
| Compound of Example 41 | 45.6 |
| Compound of Example 42 | 27.2 |
| Compound of Example 43 | 31.3 |
| Compound of Example 44 | 128 |
| Compound of Example 45 | 33.8 |
| Compound of Example 46 | 531 |

TABLE 2-2-continued

| Test Substance | IC$_{50}$ (nmol/L) |
|---|---|
| Compound of Example 47 | 56.6 |
| Compound of Example 48 | 171 |
| Compound of Example 49 | 204 |
| Compound of Example 50 | 35.1 |
| Compound of Example 51 | 142 |
| Compound of Example 52 | 661 |
| Compound of Example 53 | 254 |
| Compound of Example 54 | 95.1 |
| Compound of Example 55 | 90.2 |
| Compound of Example 56 | 55.8 |
| Compound of Example 57 | 653 |
| Compound of Example 58 | 528 |
| Compound of Example 59 | 335 |
| Compound of Example 60 | 59.8 |
| Compound of Example 61 | 57.9 |
| Compound of Example 62 | 138 |
| Compound of Example 63 | 46.7 |
| Compound of Example 64 | 54.5 |
| Compound of Example 65 | 42.1 |
| Compound of Example 66 | 98.4 |
| Compound of Example 67 | 9.69 |
| Compound of Example 68 | 16.6 |
| Compound of Example 69 | 17.2 |
| Compound of Example 70 | 13.4 |
| Compound of Example 71 | 10.8 |
| Compound of Example 72 | 82.2 |
| Compound of Example 73 | 57.7 |

TABLE 2-3

| Test Substance | IC$_{50}$ (nmol/L) |
|---|---|
| Compound of Example 74 | 25.2 |
| Compound of Example 75 | 20 |
| Compound of Example 76 | 14.1 |
| Compound of Example 77 | 6.65 |
| Compound of Example 78 | 80.1 |
| Compound of Example 79 | 22.8 |
| Compound of Example 80 | 24.9 |

INDUSTRIAL APPLICABILITY

Urea derivatives (I) and pharmaceutically acceptable salts thereof have high DDR1 inhibition activity and therefore can be used as DDR1 inhibitors.

The invention claimed is:

1. A urea compound represented by Formula (I):

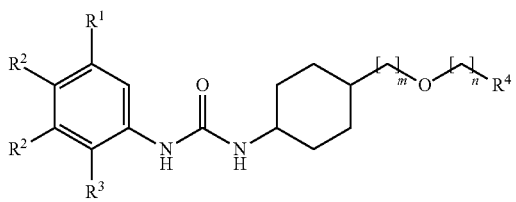

(I)

wherein,
$R^1$ is trifluoromethyl, trifluoromethoxy, or pentafluorosulfanyl;
each $R^2$ is independently a hydrogen atom or methyl which is optionally substituted by one hydroxyl or one saturated heterocyclyl having four to six ring-forming atoms;
$R^3$ is a hydrogen atom, halogen atom, $C_1$-$C_3$ alkyl, saturated heterocyclyl having four to six ring-forming atoms and optionally having an oxo group, or $R^5$O—;
$R^4$ is phenyl, pyridyl, pyridazinyl, or pyrimidinyl, which phenyl, pyridyl, pyridazinyl, or pyrimidinyl is optionally substituted by one $R^6$;
m and n are independently 0 or 1;
$R^5$ is $C_1$-$C_3$ alkyl or saturated heterocyclyl having four to six ring-forming atoms (provided that if a nitrogen atom is included in the ring-forming atoms of $R^5$, said nitrogen atom is optionally substituted by acetyl);
$R^6$ is carbamoyl, phenyl, heteroaryl having five or six ring-forming atoms, saturated heterocyclyl having four to six ring-forming atoms, or ($R^7$)$R^8$N—; and
each of $R^7$ and $R^8$ is independently a hydrogen atom, or $C_1$-$C_3$ alkyl which is optionally substituted by hydroxyl (excluding when m and n are 0; and $R^4$ is phenyl or pyridyl, which phenyl or pyridyl is substituted by carbamoyl) or a pharmaceutically acceptable salt thereof.

2. The urea compound according to claim 1, or a pharmaceutically acceptable salt thereof, wherein
each $R^2$ is independently a hydrogen atom or hydroxymethyl;
$R^3$ is a hydrogen atom, morpholinyl, 3-oxopiperazinyl, or $R^5$O—;
$R^4$ is pyridyl or pyrimidinyl, which pyridyl or pyrimidinyl is optionally substituted by one $R^6$;
$R^5$ is $C_1$-$C_3$ alkyl, 3-oxetanyl, or 3-azetidinyl, 3-pyrrolidinyl, or 4-piperidinyl, which 3-azetidinyl, 3-pyrrolidinyl, or 4-piperidinyl optionally has a nitrogen atom substituted by acetyl; and
$R^6$ is carbamoyl, pyridyl, morpholinyl, or ($R^7$)$R^8$N—.

3. The urea compound according to claim 2, or a pharmaceutically acceptable salt thereof, wherein
$R^4$ is a group represented by one formula selected from Formulae (IIa) to (IIc), and
m and n are 0:

(IIa)

(IIb)

(IIc)

wherein $R^9$ is carbamoyl, pyridyl, morpholinyl, or ($R^7$)$R^8$N—; and the wavy line represents the point to which Formula (I) is linked.

4. The urea compound according to claim 2, or a pharmaceutically acceptable salt thereof, wherein
$R^4$ is a group represented by Formula (IId) or (IIe); and one of m and n is 0 and the other is 1:

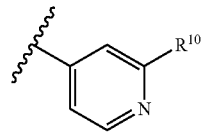
(IId)

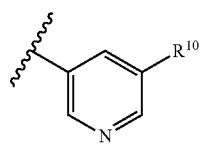
(IIe)

wherein $R^{10}$ is a hydrogen atom or carbamoyl; and the wavy line represents the point to which Formula (I) is linked.

5. A method of inhibiting Discoidin Domain Receptor 1, comprising administering an effective amount of the urea compound according to claim 1 or a pharmaceutically acceptable salt thereof.

6. A method of inhibiting Discoidin Domain Receptor 1, comprising administering an effective amount of the urea compound according to claim 2 or a pharmaceutically acceptable salt thereof.

7. A method of inhibiting Discoidin Domain Receptor 1, comprising administering an effective amount of the urea compound according to claim 3 or a pharmaceutically acceptable salt thereof.

8. A method of inhibiting Discoidin Domain Receptor 1, comprising administering an effective amount of the urea compound according to claim 4 or a pharmaceutically acceptable salt thereof.

* * * * *